US012780905B2

(12) United States Patent
Becker et al.

(10) Patent No.: US 12,780,905 B2
(45) Date of Patent: Nov. 3, 2026

(54) NEUTRALIZING ANTIBODIES AGAINST SARS-RELATED CORONAVIRUS

(71) Applicants: UNIVERSITY OF COLOGNE, Cologne (DE); PHILIPPS-UNIVERSITÄT MARBURG, Marburg (DE)

(72) Inventors: Stephan Becker, Marburg (DE); Henning Grüll, Cologne (DE); Florian Klein, Cologne (DE); Christoph Kreer, Cologne (DE); Matthias Zehner, Bonn (DE)

(73) Assignees: UNIVERSITY OF COLOGNE, Cologne (DE); PHILIPPS-UNIVERSITÄT MARBURG, Marburg (DE)

( * ) Notice: Subject to any disclaimer, the term of this patent is extended or adjusted under 35 U.S.C. 154(b) by 380 days.

(21) Appl. No.: 17/333,795

(22) Filed: May 28, 2021

(65) Prior Publication Data

US 2021/0371503 A1 Dec. 2, 2021

(30) Foreign Application Priority Data

May 29, 2020 (EP) .................................... 20177354
Jun. 25, 2020 (EP) .................................... 20182325
Dec. 11, 2020 (EP) .................................... 20213562

(51) Int. Cl.
*C07K 16/10* (2026.01)
*A61K 39/00* (2006.01)
*A61P 31/14* (2006.01)
*C07K 16/104* (2026.01)

(52) U.S. Cl.
CPC ............ *C07K 16/104* (2026.01); *A61P 31/14* (2018.01); *A61K 2039/505* (2013.01); *A61K 2039/545* (2013.01); *C07K 2317/565* (2013.01); *C07K 2317/76* (2013.01)

(58) Field of Classification Search
CPC ...................... A61K 2039/505; C07K 16/1002
See application file for complete search history.

(56) References Cited

PUBLICATIONS

Zhang et al. (Curr. Opin. Virol. Oct. 2021; 50: 173-82).*
Löfblom et al. (FEBS Lett. Jun. 18, 2010; 584 (12): 2670-80).*
Tian et al. (Emerg. Microbes Infect. Feb. 17, 2020; 9 (1):382-5).*
Seydoux et al. (Version 1. bioRxiv. Preprint. May 12, 2020; pp. 1-37).*
Zhang et al. (Curr. Opin. Virol. Oct. 2021; 50: 173-82) (Year: 2021).*
Löfblom et al. (FEBS Lett. Jun. 18, 2010; 584 (12): 2670-80) (Year: 2010).*
Tian et al. (Emerg. Microbes Infect. Feb. 17, 2020; 9 (1):382-5) (Year: 2020).*
Seydoux et al. (Version 1. bioRxiv. Preprint. May 12, 2020; pp. 1-37) (Year: 2020).*
Shi et al. Nature. 584: 120-124: Published Online: May 26, 2020 (Year: 2020).*
Prescribing Information for Humira (Published: Aug. 2018) (Year: 2018).*
Prescribing Information for Zenapax (Published: Sep. 2010) (Year: 2010).*
Prescribing Information for Rituxan (Published: Feb. 2020) (Year: 2020).*
Mcbride et al. Journal of Experimental Medicine. 155(5): 1480-1490; Published: May 1, 1982 (Year: 1982).*
Taiwanese Office Action for corresponding TW Application No. 110119505, dated Apr. 18, 2025, 10 pages.
Wang, Chunyan et al. "A human monoclonal antibody blocking SARS-CoV-2 infection." Nature communications. vol. 11, 1 2251. May 2020.
Shi, Rui et al. "A human neutralizing antibody targets the receptor-binding site of SARS-CoV-2." Nature. vol. 584, 7819, Epub May 26, 2020, 120-124.
European Office Action for corresponding EP Application No. 21729503.9, dated Aug. 18, 2025, 6 pages.
Berry, Jody D. et al., "Development and characterisation of neutralising monoclonal antibody to the SARS-coronavirus", Journal of Virological Methods, Elsevier, vol. 120, No. 1, 2004, pp. 87-96.
Koch, Till et al., "Safety and immunogenicity of a modified vaccinia virus Ankara vector vaccine candidate for Middle East respiratory syndrome: an open-label, phase 1 trial", The Lancet Infectious Diseases, Elsevier, vol. 20, No. 7, Apr. 2020, pp. 827-838.
Chen, Xiangyu et al., "Human monoclonal antibodies block the binding of SARS-CoV-2 spike protein in angiotensin converting enzyme 2 receptor", Cellular & Molecular Immunology, Chinese Society of Immunology, vol. 17, No. 6, Apr. 2020, pp. 647-649.
Cao, Yunlong et al., "Potent Neutralizing Antibodies against SARS-CoV-2 Identified by High-Throughput Single-Cell Sequencing of Convalescent Patients' B Cells", CellPress, Elsevier, vol. 182, No. 1, May 2020, pp. 73-84.
Ehrhardt, Stefanie A. et al., "Polyclonal and convergent antibody response to Ebola virus vaccine rVSV-ZEBOV", Nature Medicine, Nature Pub. Co., vol. 25, No. 10, Oct. 2019.

(Continued)

*Primary Examiner* — Juliet C Switzer
*Assistant Examiner* — Katherine Ann Holtzman
(74) *Attorney, Agent, or Firm* — Eversheds-Sutherland (US) LLP

(57) ABSTRACT

The present invention relates to antibodies or antigen-binding fragments thereof against SARS-related coronavirus, a pharmaceutical composition comprising such antibodies or antigen-binding fragments thereof, a kit comprising such antibodies or antigen-binding fragments thereof. The present invention also relates to the antibodies or antigen-binding fragments thereof, the pharmaceutical composition, and the kit, for use as a medicament, and in the treatment or prevention of a disease caused by SARS-related coronavirus.

29 Claims, 17 Drawing Sheets

Specification includes a Sequence Listing.

(56) References Cited

PUBLICATIONS

Galson, Jacob D. et al., "Deep Sequencing of B Cell Receptor Repertoires from Covid-19 Patients Reveals Strong Convergent Immune Signatures", Frontiers in Immunology, vol. 11, Dec. 2020, pp. 1-11.

Kreer, Christoph et al., "Longitudinal Isolation of Potent Near-Germline SARS-CoV-2-Neutralizing Antibodies from Covid-19 Patients", CellPress, Elsevier, cell 182, Aug. 2020, pp. 843-854.

* cited by examiner

FIG. 4

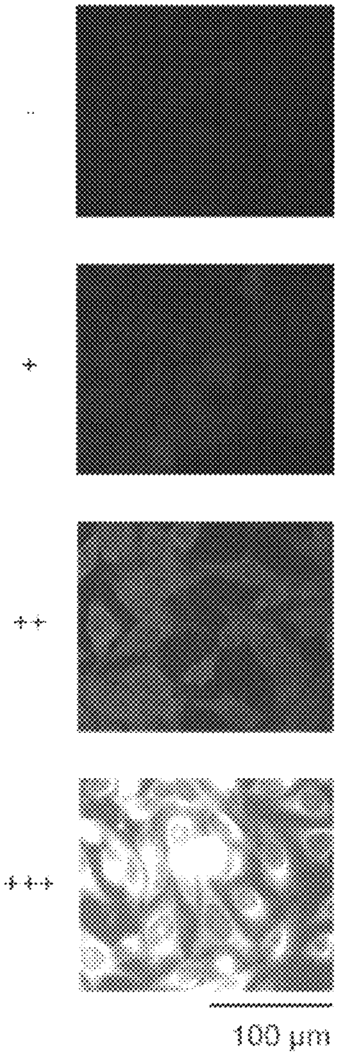

| Antibody | Result | Antibody | Result |
|---|---|---|---|
| CnC2t1p1_B4 | - | MnC1t3p1_F3 | - |
| CnC2t1p1_B10 | - | MnC1t3p1_G9 | ++ |
| CnC2t1p1_D6 | - | | |
| CnC2t1p1_E8 | - | MnC2t1p1_A3 | - |
| CnC2t1p1_E12 | - | MnC2t1p1_A12 | - |
| CnC2t1p1_F5_LC | ++ | MnC2t1p1_C1 | - |
| CnC2t1p1_G6 | - | MnC2t1p1_C5 | - |
| | | MnC2t1p1_D7 | - |
| FnC1t1p1_C11 | - | MnC2t2p1_C11 | - |
| FnC1t1p2_A5 | ++ | MnC2t2p1_G7 | - |
| FnC1t2p1_A12 | + | | |
| FnC1t2p1_D4 | - | MnC4t1p1_A10 | - |
| FnC1t2p1_G5 | - | MnC4t1p1_A11 | - |
| | | MnC4t2p1_B3 | - |
| HbnC2t1p2_D9 | - | MnC4t2p1_C5 | - |
| | | MnC4t2p1_D1 | - |
| HbnC3t1p1_C6 | - | MnC4t2p1_D10 | - |
| HbnC3t1p1_F4 | + | MnC4t2p1_E6 | - |
| HbnC3t1p1_G4 | ++ | MnC4t2p1_F5 | - |
| HbnC3t1p2_B10 | - | | - |
| HbnC3t1p2_C6 | - | MnC4t2p2_A4 | - |
| HbnC4t1p1_D5 | - | MnC5t1p1_C6 | - |
| | | MnC5t2p1_E9 | - |
| | | MnC5t2p1_G1 | - |
| Controls | | 3BNC117 | + |
| NIH45-46 | ++ | 2F5 | +++ |
| NIH45-46$^{G54W}$ | +++ | 4E10 | +++ |

| Antibody | | | | | | | Binding data[1] | | | | Epitope | | | HEp2 autoreactivity | Neutralization |
|---|---|---|---|---|---|---|---|---|---|---|---|---|---|---|---|
| Name | Clone # | Number of clonal members | VH-gene | VH-gene germline identity | VL-gene | VL-gene germline identity | SARS-CoV-2 (spike protein) | | | EBOV ΔTM | RBD[2] | S1[3] | monomeric | | |
| | | | | | | | $EC_{50}$ (µg/ml) | $K_D$ (nM) | Commercial ELISA[*] | $EC_{50}$ | $EC_{50}$ | $EC_{50}$ | $EC_{50}$ | | IC100 (µg/ml) |
| CnC2t1p1_A2 | C2_5 | 4 | IGHV1-46 | 99,7 | IGKV3-20 | 100 | 0.03 | N/A | 0.40 | - | + | ++ | ++ | N/A | n.n. |
| CnC2t1p1_A6 | C2_17 | 2 | IGHV3-30 | 99,3 | IGKV3-11 | 100 | 0.90 | N/A | N/A | - | - | + | ++ | N/A | N/A |
| CnC2t1p1_B10 | C2_8 | 2 | IGHV1-69 | 100 | IGKV3-11 | 100 | 0.32 | N/A | N/A | - | +++ | +++ | +++ | - | 12.50 |
| CnC2t1p1_B4 | C2_2 | 2 | IGHV1-18 | 100 | IGLV2-23 | 100 | 0.03 | N/A | 7.57 | - | +++ | +++ | +++ | - | 0.78 |
| CnC2t1p1_D6 | C2_23 | 2 | IGHV3-49 | 100 | IGKV2-28 | 98 | 0.03 | N/A | 3.28 | - | +++ | +++ | +++ | - | 3.75 |
| CnC2t1p1_E11 | single | - | IGHV3-30 | 100 | IGLV2-14 | 99,3 | 5.20 | N/A | <0.15 | - | - | + | + | N/A | n.n. |
| CnC2t1p1_E12 | C2_23 | 2 | IGHV3-49 | 99,7 | IGKV2-28 | 96 | 0.03 | N/A | 3.03 | - | +++ | +++ | +++ | - | 3.13 |
| CnC2t1p1_E7 | C2_5 | 4 | IGHV1-46 | 100 | IGKV3-20 | 99 | 0.04 | N/A | N/A | - | - | ++ | + | N/A | n.n. |
| CnC2t1p1_E8 | C2_3 | 6 | IGHV1-2 | 91,5 | IGLV2-23 | 95,6 | 0.13 | N/A | 6.89 | - | +++ | +++ | +++ | - | 4.43 |
| CnC2t1p1_F5 | single | - | IGHV3-30 | 99 | IGLV5-45 | 99,7 | 0.05 | N/A | N/A | +++ | + | + | +++ | ++ | N/A |
| CnC2t1p1_G6 | C2_3 | 6 | IGHV1-2 | 90,4 | IGLV2-23 | 94,6 | 0.31 | N/A | 4.72 | - | +++ | +++ | +++ | - | 12.50 |
| CnC2t1p2_E4 | C2_11 | 3 | IGHV3-15 | 100 | IGKV3-20 | 100 | 0.28 | N/A | <0.15 | - | - | + | + | N/A | n.n. |
| CnC2t1p2_F12 | C2_10 | 2 | IGHV3-15 | 100 | IGKV3-20 | 99,3 | 0.06 | N/A | <0.15 | - | - | + | + | N/A | n.n. |
| CnC2t1p2_F4 | C2_15 | 3 | IGHV3-30 | 96,3 | IGKV6-21 | 98,4 | 0.04 | N/A | <0.15 | - | - | + | + | N/A | n.n. |
| CnC2t1p2_G4 | C2_11 | 3 | IGHV3-15 | 100 | IGKV3-20 | 100 | 0.25 | N/A | <0.15 | - | - | + | + | N/A | n.n. |
| FnC1t1p1_B6 | F1_77 | 11 | IGHV3-53 | 94,2 | IGLV2-8 | 98,6 | 0.96 | N/A | <0.15 | - | +++ | ++ | + | N/A | n.n. |
| FnC1t1p1_C11 | F1_76 | 4 | IGHV3-53 | 93,8 | IGLV2-8 | 99,7 | 2.91 | N/A | <0.15 | + | + | + | + | - | n.n. |
| FnC1t1p2_A5 | single | - | IGHV1-8 | 100 | IGKV3-20 | 100 | 1.36 | N/A | <0.15 | + | - | + | + | ++ | 16.00 |
| FnC1t2p1_A12 | F1_89 | 2 | IGHV4-4 | 97,9 | IGLV2-14 | 97,6 | 2.81 | N/A | <0.15 | + | - | + | + | + | n.n. |
| FnC1t2p1_D4 | F1_95 | 2 | IGHV7-4-1 | 96,6 | IGKV1-33 | 99 | 0.02 | 0.20 | 3.03 | - | +++ | +++ | +++ | - | 0.28 |

[1] Intensity above an OD of ≥0.25 (not shown) and $EC_{50}$ below 30 µg/ml was defined as binding

[2] Receptor binding domain

[3] truncated S1 subunit

[*] Euroimmun IgG detection kit

\+ $EC_{50}$ >1 µg/µl

++ 0.1µg/µl < $EC_{50}$ <1 µg/µl

+++ $EC_{50}$ <0.1 µg/µl n.n. not neutralizing

FIG. 5A

| Antibody | | | | | | | Binding data[1] | | | | Epitope | | | HEp2 autoreactivity | Neutralization |
|---|---|---|---|---|---|---|---|---|---|---|---|---|---|---|---|
| Name | Clone # | Number of clonal members | VH-gene | VH-gene germline identity | VL-gene | VL-gene germline identity | SARS-CoV-2 (spike protein) | | | EBOVΔTM | RBD[2] | S1[3] | monomeric | | |
| | | | | | | | $EC_{50}$ (μg/ml) | $K_D$ (nM) | Commercial ELISA* | $EC_{50}$ | $EC_{50}$ | $EC_{50}$ | $EC_{50}$ | | IC100 (μg/ml) |
| FnC1t2p1_G5 | F1_95 | 2 | IGHV7-4-1 | 96,6 | IGKV1-33 | 99 | 0.02 | 0.10 | 9.00 | - | +++ | +++ | +++ | - | 0.33 |
| FnC2t1p1_B1 | F2_12 | 3 | IGHV4-34 | 92,2 | IGLV1-44 | 92,7 | 0.78 | N/A | <0.15 | - | ++ | ++ | + | N/A | n.n. |
| HbnC1t1p3_H8 | H1_6 | 2 | IGHV3-21 | 100 | IGKV1-5 | 100 | 0.08 | N/A | <0.15 | - | - | + | +++ | N/A | n.n. |
| HbnC2t1p2_D9 | H2_20 | 2 | IGHV3-33 | 98,6 | IGKV3-11 | 99 | 0.04 | N/A | N/A | - | ++ | ++ | ++ | - | 0.93 |
| HbnC3t1p1_C6 | H3_3 | 2 | IGHV1-58 | 99,7 | IGKV3-20 | 99,7 | 0.06 | N/A | 9.00 | - | +++ | +++ | +++ | - | 0.04 |
| HbnC3t1p1_F4 | H3_10 | 10 | IGHV3-30 | 93,2 | IGKV1-5 | 96,1 | 0.04 | N/A | 8.78 | - | ++ | +++ | ++ | + | 0.78 |
| HbnC3t1p1_G4 | single | - | IGHV3-66 | 99,7 | IGKV3-20 | 98,3 | 0.02 | N/A | N/A | - | +++ | +++ | +++ | ++ | 0.12 |
| HbnC3t1p2_B10 | single | - | IGHV3-66 | 99 | IGKV3-20 | 97,9 | 0.22 | N/A | 9.00 | - | +++ | +++ | +++ | - | 0.25 |
| HbnC3t1p2_C6 | H3_3 | 2 | IGHV1-58 | 98,3 | IGKV3-20 | 99,7 | 0.04 | N/A | 10.00 | - | +++ | +++ | +++ | - | 0.33 |
| HbnC4t1p1_A1 | H4_5 | 9 | IGHV3-23 | 100 | IGKV1-33 | 100 | 0.12 | N/A | 2.98 | - | +++ | +++ | +++ | N/A | n.n. |
| HbnC4t1p1_A6 | H4_23 | 2 | IGHV3-30-3 | 99 | IGKV4-1 | 98,4 | 3.36 | N/A | <0.15 | - | - | + | + | N/A | N/A |
| HbnC4t1p1_C11 | H4_5 | 9 | IGHV3-23 | 100 | IGKV1-33 | 100 | 0.25 | N/A | 8.54 | - | +++ | +++ | +++ | N/A | n.n. |
| HbnC4t1p1_D5 | H4_27 | 4 | IGHV3-9 | 99,7 | IGKV1-39 | 98,6 | 0.25 | N/A | <0.15 | ++ | ++ | ++ | + | - | 10.51 |
| HbnC4t1p1_G2 | single | - | IGHV3-30 | 98,3 | IGKV1-39 | 99,7 | 0.09 | N/A | <0.15 | - | - | + | + | N/A | N/A |
| HbnC5t1p1_B6 | H5_2 | 6 | IGHV1-46 | 87,6 | IGKV2-24 | 97 | 0.07 | N/A | 9.36 | - | - | +++ | + | N/A | N/A |
| HbnC5t1p1_C11 | H5_4 | 2 | IGHV1-46 | 93,2 | IGKV2-24 | 96,4 | 0.46 | N/A | N/A | - | - | + | + | N/A | N/A |
| HbnC5t1p1_D4 | H5_26 | 2 | IGHV3-53 | 98,6 | IGKV1-9 | 100 | 0.04 | N/A | <0.15 | - | - | + | + | N/A | n.n. |
| MnC1t2p1_A5 | M1_19 | 22 | IGHV3-49 | 89,3 | IGKV4-1 | 96,4 | 0.03 | N/A | <0.15 | - | - | + | +++ | N/A | N/A |
| MnC1t2p1_B11 | M1_19 | 22 | IGHV3-49 | 93,3 | IGKV4-1 | 97,7 | 0.03 | N/A | <0.15 | - | - | + | +++ | N/A | n.n. |
| MnC1t3p1_B7 | M1_19 | 22 | IGHV3-49 | 90,1 | IGKV4-1 | 95,1 | 0.04 | N/A | N/A | N/A | N/A | N/A | N/A | N/A | N/A |

[1] intensity above an OD of ≥0.25 (not shown) and $EC_{50}$ below 30 μg/ml was defined as binding

[2] Receptor binding domain

[3] truncated S1 subunit

* Euroimmun IgG detection kit

+ $EC_{50}$ >1 μg/μl

++ 0.1μg/μl < $EC_{50}$ <1 μg/μl

+++ $EC_{50}$ <0.1 μg/μl n.n. not neutralizing

FIG. 5B

| Antibody | | | | | | | Binding data | | | | Epitope | | | HEp2 autoreactivity | Neutralization |
|---|---|---|---|---|---|---|---|---|---|---|---|---|---|---|---|
| Name | Clone # | Number of clonal members | VH-gene | VH-gene germline identity | VL-gene | VL-gene germline identity | SARS-CoV-2 (spike protein) | | | EBOVΔTM | RBD[2] | S1[3] | monomeric | | |
| | | | | | | | $EC_{50}$ (µg/ml) | $K_D$ (nM) | IgG detection test[*] | $EC_{50}$ | $EC_{50}$ | $EC_{50}$ | $EC_{50}$ | | IC100 (µg/ml) |
| MnC1t3p1_E3 | M1_19 | 22 | IGHV3-49 | 93,9 | IGKV4-1 | 98,7 | 0.03 | N/A | N/A | - | - | - | - | N/A | N/A |
| MnC1t3p1_F3 | single | - | IGHV3-30 | 97,3 | IGLV2-23 | 98,3 | 2.82 | N/A | N/A | + | - | - | - | - | N/A |
| MnC1t3p1_G9 | M1_2 | 3 | IGHV3-23 | 94,5 | IGLV7-46 | 97,6 | 0.03 | N/A | 5.42 | - | +++ | +++ | +++ | ++ | 8.84 |
| MnC2t1p1_A12 | single | - | IGHV1-2 | 99,7 | IGLV2-14 | 99 | 4.03 | N/A | <0.15 | - | - | - | + | - | n.n. |
| MnC2t1p1_A3 | M2_25 | 3 | IGHV3-66 | 99 | IGKV1D-12 | 100 | 0.05 | 0.70 | 6.44 | - | +++ | +++ | +++ | - | 0.78 |
| MnC2t1p1_C1 | single | - | IGHV3-21 | 99,7 | IGKV3-15 | 99 | 0.15 | N/A | <0.15 | ++ | - | ++ | +++ | - | n.n. |
| MnC2t1p1_C12 | single | - | IGHV4-31 | 97,3 | IGKV3-20 | 96,8 | 0.02 | N/A | <0.15 | - | - | - | +++ | N/A | n.n. |
| MnC2t1p1_C5 | M2_25 | 3 | IGHV3-66 | 100 | IGKV1D-12 | 100 | 0.07 | N/A | 5.95 | - | +++ | +++ | +++ | - | 3.72 |
| MnC2t2p1_C11 | single | - | IGHV1-69 | 98,6 | IGKV1-39 | 98,9 | 0.02 | 0.02 | 6.79 | - | +++ | +++ | +++ | - | 0.25 |
| MnC2t2p1_D7 | M2_29 | 3 | IGHV3-7 | 95,9 | IGLV2-8 | 98,3 | 1.41 | N/A | <0.15 | + | - | - | - | N/A | n.n. |
| MnC2t2p1_E1 | single | - | IGHV4-61 | 98,3 | IGKV1-9 | 98,6 | 0.90 | N/A | <0.15 | - | - | - | + | N/A | n.n. |
| MnC2t2p1_E4 | M2_42 | 3 | IGHV4-4 | 95,9 | IGLV2-14 | 95,9 | 0.70 | N/A | <0.15 | - | - | - | ++ | N/A | n.n. |
| MnC2t2p1_G7 | M2_33 | 2 | IGHV3-73 | 91,4 | IGLV2-14 | 93,8 | 4.49 | N/A | <0.15 | + | - | - | - | - | n.n. |
| MnC4t1p1_A10 | M4_27 | 18 | IGHV4-39 | 94,6 | IGKV1-17 | 96,8 | 0.07 | N/A | 4.87 | - | +++ | +++ | +++ | - | 42.04 |
| MnC4t1p1_A11 | M4_22 | 5 | IGHV3-48 | 96,9 | IGKV3-20 | 97,9 | 0.05 | 2000 | 4.52 | - | +++ | +++ | +++ | - | 100.00 |
| MnC4t1p1_A6 | M4_25 | 15 | IGHV3-9 | 95,3 | IGKV1-12 | 97,5 | 0.07 | N/A | 10.24 | - | +++ | +++ | +++ | N/A | n.n. |
| MnC4t1p1_A7 | M4_38 | 7 | IGHV4-61 | 93,6 | IGKV1-39 | 92,6 | 2.81 | N/A | <0.15 | - | - | - | - | N/A | N/A |
| MnC4t2p1_A8 | M4_40 | 3 | IGHV7-4-1 | 96,6 | IGKV3-20 | 96,8 | 1.80 | N/A | 0.24 | - | +++ | ++ | ++ | N/A | n.n. |
| MnC4t2p1_B3 | M4_25 | 15 | IGHV3-9 | 94,6 | IGKV1-12 | 96,8 | 0.06 | 0.09 | N/A | - | +++ | +++ | +++ | - | 0.66 |
| MnC4t2p1_C5 | M4_3 | 7 | IGHV1-2 | 95,9 | IGLV2-8 | 98,6 | 0.79 | N/A | <0.15 | ++ | + | + | + | - | n.n. |

[1] Intensity above an OD of ≥0.25 (not shown) and $EC_{50}$ below 30 µg/ml was defined as binding
[2] Receptor binding domain
[3] truncated S1 subunit
[*] Euroimmun IgG detection kit \+ $EC_{50}$ >1 µg/µl
++ 0.1µg/µl < $EC_{50}$ <1 µg/µl
+++ $EC_{50}$ <0.1 µg/µl
n.n. not neutralizing

FIG. 5C

| Antibody | | | | | | | Binding data | | | | Epitope | | | HEp2 autoreactivity | Neutralization |
|---|---|---|---|---|---|---|---|---|---|---|---|---|---|---|---|
| Name | Clone # | Number of clonal members | VH-gene | VH-gene germline identity | VL-gene | VL-gene germline identity | SARS-CoV-2 (spike protein) | | | EBOVΔTM | RBD[2] | S1[3] | monomeric | | |
| | | | | | | | $EC_{50}$ (µg/ml) | $K_D$ (nM) | IgG detection test[4] | $EC_{50}$ | $EC_{50}$ | $EC_{50}$ | $EC_{50}$ | | $IC_{100}$ (µg/ml) |
| MnC4t2p1_D1 | single | - | IGHV1-69 | 99 | IGKV1-5 | 98,9 | 3.88 | N/A | <0.15 | + | - | - | + | - | n.n. |
| MnC4t2p1_D10 | M4_27 | 18 | IGHV4-39 | 94,6 | IGKV1-17 | 96,8 | 0.18 | 440 | 5.30 | - | +++ | +++ | +++ | - | 21.32 |
| MnC4t2p1_E6 | M4_25 | 15 | IGHV3-9 | 95,3 | IGKV1-12 | 97,5 | 0.03 | N/A | 8.08 | - | +++ | +++ | +++ | - | 50.00 |
| MnC4t2p1_F5 | M4_27 | 18 | IGHV4-39 | 94,6 | IGKV1-17 | 96,8 | 0.07 | N/A | 5.19 | - | +++ | +++ | +++ | - | 100.00 |
| MnC4t2p1_F8 | M4_25 | 15 | IGHV3-9 | 95,3 | IGKV1-12 | 97,5 | 0.03 | N/A | 10.08 | - | +++ | +++ | +++ | N/A | n.n. |
| MnC4t2p1_G3 | M4_40 | 3 | IGHV7-4-1 | 95,2 | IGKV3-20 | 95,8 | 0.03 | N/A | 7.60 | - | +++ | +++ | +++ | N/A | n.n. |
| MnC4t2p2_A4 | M4_39 | 5 | IGHV7-4-1 | 96,6 | IGKV3-20 | 95,8 | 0.02 | 14 | 10.17 | - | +++ | +++ | +++ | - | 21.02 |
| MnC4t2p2_A7 | M4_35 | 2 | IGHV4-59 | 95,6 | IGKV4-1 | 98 | 0.11 | N/A | <0.15 | - | - | - | - | N/A | N/A |
| MnC5t1p1_C12 | single | - | IGHV3-30 | 99,3 | IGKV1-9 | 99,7 | 1.40 | N/A | <0.15 | - | - | - | +++ | N/A | n.n. |
| MnC5t1p1_C4 | M5_30 | 2 | IGHV3-30-3 | 99 | IGKV3-20 | 99,3 | 1.31 | N/A | <0.15 | - | - | - | +++ | N/A | n.n. |
| MnC5t1p1_C6 | single | - | IGHV3-30-3 | 99,7 | IGKV3-20 | 100 | 4.23 | N/A | <0.15 | + | - | - | ++ | - | n.n. |
| MnC5t1p1_C7 | single | - | IGHV3-30-3 | 99 | IGKV1-5 | 99,6 | 4.62 | N/A | <0.15 | - | - | - | - | N/A | n.n. |
| MnC5t2p1_B5 | single | - | IGHV3-30-3 | 97,6 | IGKV3-20 | 99,3 | 3.69 | N/A | <0.15 | - | - | - | +++ | N/A | n.n. |
| MnC5t2p1_C2 | single | - | IGHV3-30-3 | 100 | IGLV4-69 | 100 | 4.17 | N/A | <0.15 | - | - | - | - | N/A | n.n. |
| MnC5t2p1_C5 | single | - | IGHV3-30-3 | 100 | IGKV4-1 | 100 | 3.76 | N/A | <0.15 | - | - | - | - | N/A | n.n. |
| MnC5t2p1_E12 | single | - | IGHV3-30-3 | 97,6 | IGKV6-21 | 99,3 | 3.87 | N/A | <0.15 | - | - | - | +++ | N/A | n.n. |
| MnC5t2p1_E9 | M5_1 | 4 | IGHV1-18 | 85,3 | IGKV3-15 | 97,6 | 3.01 | N/A | <0.15 | + | - | - | +++ | - | n.n. |
| MnC5t2p1_G1 | M5_4 | 2 | IGHV1-58 | 98,6 | IGKV3-20 | 99 | 0.03 | 17 | 10.48 | - | +++ | +++ | +++ | - | 2.63 |
| MnC5t2p1_G6 | M5_1 | 4 | IGHV1-18 | 87,7 | IGKV3-15 | 96,2 | 3.71 | N/A | <0.15 | - | - | - | +++ | N/A | n.n. |

[1] Intensity above an OD of ≥0.25 (not shown) and $EC_{50}$ below 30 µg/ml was defined as binding
[2] Receptor binding domain
[3] truncated S1 subunit
[4] Euroimmun IgG detection kit + $EC_{50}$ >1 µg/µl
++ 0.1µg/µl < $EC_{50}$ <1 µg/µl
+++ $EC_{50}$ <0.1 µg/µl
n.n. not neutralizing

FIG. 5D

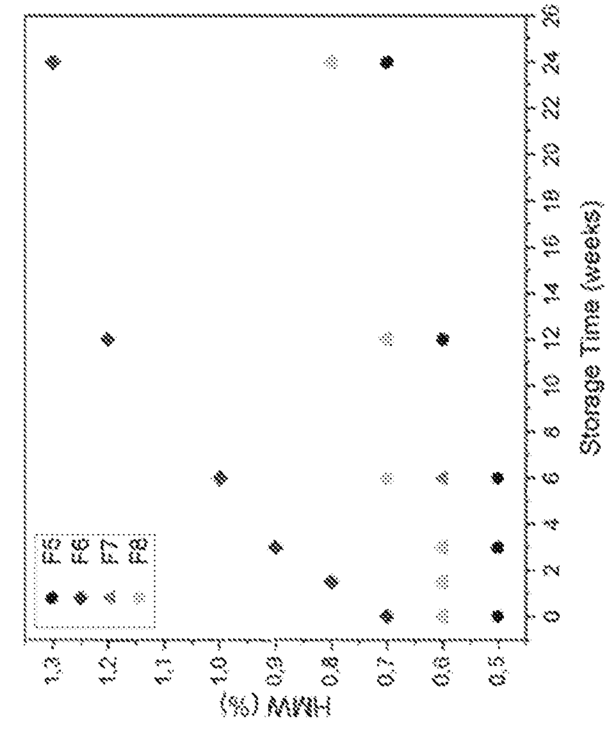
FIG. 11A
REPLACEMENT SHEET
14/17

FIG. 14
| **Parameter** | **REGN10987*** | **REGN10933*** | **DZIF-10c** |
|---|---|---|---|
| Binding Affinity Spike ***RBD*** | 26nM | 10 nM | 2 nM |
| Binding Affinity Spike ***Trimer*** | 12nM | 3nM | 0,65nM |
| MoA / Binding mode | Direct block ACE2 / RBD interaction | Direct block ACE2 / RBD interaction | No direct block ACE2 /RBD |
| DZIF-10c Competition | Yes | No | - |
| RBD Protection via HDX-MS* | Region 1  | Region 2  | Region 1 + 2  |
* REGN10987, REGN10933: J. Hansen *et al.*, *Science* 10.1126/science.abd0827 (2020)

SEQUENCE LISTING

```
<160> NUMBER OF SEQ ID NOS: 230

<210> SEQ ID NO 1
<211> LENGTH: 123
<212> TYPE: PRT
<213> ORGANISM: Homo sapiens
<220> FEATURE:
<223> OTHER INFORMATION: Heavy chain of antibody HbnC3t1p1_C6

<400> SEQUENCE: 1
```

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Pro His Cys Ser Ser Thr Ile Cys Tyr Asp Gly Phe Asp Ile
            100                 105                 110

Trp Gly Gln Gly Thr Met Val Thr Val Ser Ser
        115                 120

<210> SEQ ID NO 2
<211> LENGTH: 108
<212> TYPE: PRT
<213> ORGANISM: Homo sapiens
<220> FEATURE:
<223> OTHER INFORMATION: Light chain of antibody HbnC3t1p1_C6

<400> SEQUENCE: 2

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Val Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 3
<211> LENGTH: 117
<212> TYPE: PRT
<213> ORGANISM: Homo sapiens
<220> FEATURE:
<223> OTHER INFORMATION: Heavy chain of antibody HbnC3t1p1_G4

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Phe Tyr Ala Asp Ser Val Lys
    50                  55                  60

Gly Arg Phe Thr Ile Ser Arg Asp Asn Ser Lys Asn Thr Leu Tyr Leu

```
65                  70                  75                  80

Gln Met Asn Ser Leu Arg Ala Glu Asp Thr Ala Val Tyr Tyr Cys Ala
                85                  90                  95

Arg Asp Phe Gly Asp Phe Phe Phe Asp Tyr Trp Gly Gln Gly Thr Leu
            100                 105                 110

Val Thr Val Ser Ser
        115


<210> SEQ ID NO 4
<211> LENGTH: 107
<212> TYPE: PRT
<213> ORGANISM: Homo sapiens
<220> FEATURE:
<223> OTHER INFORMATION: Light chain of antibody HbnC3t1p1_G4

<400> SEQUENCE: 4

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gln Gly Thr Lys Val Glu Ile Lys
            100                 105


<210> SEQ ID NO 5
<211> LENGTH: 117
<212> TYPE: PRT
<213> ORGANISM: Homo sapiens
<220> FEATURE:
<223> OTHER INFORMATION: Heavy chain of antibody HbnC3t1p2_B10

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Tyr Gly Asp Tyr Phe Phe Asp Tyr Trp Gly Gln Gly Thr Leu
            100                 105                 110

Val Thr Val Ser Ser
        115


<210> SEQ ID NO 6
<211> LENGTH: 107
```

<212> TYPE: PRT
<213> ORGANISM: Homo sapiens
<220> FEATURE:
<223> OTHER INFORMATION: Light chain of antibody HbnC3t1p2_B10

<400> SEQUENCE: 6

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Ser Gly Ala Ser Ser Arg Ala Ala Gly Ile Pro Asp Arg Phe Ser Gly
    50                  55                  60

Ser Gly Ser Gly Thr Asp Phe Thr Leu Thr Ile Asn Arg Leu Glu Pro
65                  70                  75                  80

Glu Asp Phe Ala Val Tyr Tyr Cys Gln Gln Tyr Gly Ser Ser Pro Arg
                85                  90                  95

Thr Phe Gly Gln Gly Thr Lys Leu Glu Ile Lys
            100                 105
```

<210> SEQ ID NO 7
<211> LENGTH: 130
<212> TYPE: PRT
<213> ORGANISM: Homo sapiens
<220> FEATURE:
<223> OTHER INFORMATION: Heavy chain of antibody MnC2t2p1_C11

<400> SEQUENCE: 7

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Arg Tyr
            20                  25                  30

Thr Ile Ile Trp Val Arg Gln Ala Pro Gly Gln Gly Leu Glu Trp Met
        35                  40                  45

Gly Arg Ile Ile Pro Ile Leu Asp Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Gly Gly Leu Asp Tyr Phe Gly Ser Arg Asn Ser Gly Trp
            100                 105                 110

Thr Tyr Thr Trp Phe Asp Pro Trp Gly Gln Gly Thr Leu Val Thr Val
        115                 120                 125

Ser Ser
    130
```

<210> SEQ ID NO 8
<211> LENGTH: 107
<212> TYPE: PRT
<213> ORGANISM: Homo sapiens
<220> FEATURE:
<223> OTHER INFORMATION: Light chain of antibody MnC2t2p1_C11

<400> SEQUENCE: 8

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ser Ser Tyr
```

```
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Leu Tyr
                85                  90                  95

Ser Phe Gly Gln Gly Thr Lys Leu Glu Ile Lys
            100                 105


<210> SEQ ID NO 9
<211> LENGTH: 118
<212> TYPE: PRT
<213> ORGANISM: Homo sapiens
<220> FEATURE:
<223> OTHER INFORMATION: Heavy chain of antibody FnC1t2p1_D4

<400> SEQUENCE: 9

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Leu Arg Phe
            20                  25                  30

Ala Met Asn Trp Leu Arg Gln Ala Pro Gly Gln Gly Leu Glu Trp Met
        35                  40                  45

Gly Trp Ile Asp Thr Asn Thr Gly Thr Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Leu Arg Gly Ala Asn Leu Val Pro Trp Gly Gln Gly Thr
            100                 105                 110

Leu Val Thr Val Ser Ser
        115


<210> SEQ ID NO 10
<211> LENGTH: 107
<212> TYPE: PRT
<213> ORGANISM: Homo sapiens
<220> FEATURE:
<223> OTHER INFORMATION: Light chain of antibody FnC1t2p1_D4

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ser Asn Tyr
            20                  25                  30

Leu Asn Trp Tyr Gln Gln Gln Pro Gly Lys Ala Pro Lys Leu Leu Ile
        35                  40                  45

Tyr Asp Ala Phe Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95
```

```
Thr Phe Gly Gly Gly Thr Lys Val Glu Ile Lys
            100                 105


<210> SEQ ID NO 11
<211> LENGTH: 118
<212> TYPE: PRT
<213> ORGANISM: Homo sapiens
<220> FEATURE:
<223> OTHER INFORMATION: Heavy chain of antibody FnC1t2p1_G5

<400> SEQUENCE: 11

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Leu Arg Phe
            20                  25                  30

Ala Met Asn Trp Leu Arg Gln Ala Pro Gly Gln Gly Leu Glu Trp Met
        35                  40                  45

Gly Trp Ile Asp Thr Asn Thr Gly Thr Pro Thr Tyr Ala Gln Gly Phe
    50                  55                  60

Thr Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Ser Leu Arg Gly Ala Asn Leu Val Pro Trp Gly Gln Gly Thr
            100                 105                 110

Leu Val Thr Val Ser Ser
        115


<210> SEQ ID NO 12
<211> LENGTH: 107
<212> TYPE: PRT
<213> ORGANISM: Homo sapiens
<220> FEATURE:
<223> OTHER INFORMATION: Light chain of antibody FnC1t2p1_G5

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Val Ser Asn Tyr
            20                  25                  30

Leu Asn Trp Tyr Gln Gln Gln Pro Gly Lys Ala Pro Lys Leu Leu Ile
        35                  40                  45

Tyr Asp Ala Phe Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105


<210> SEQ ID NO 13
<211> LENGTH: 123
<212> TYPE: PRT
<213> ORGANISM: Homo sapiens
<220> FEATURE:
<223> OTHER INFORMATION: Heavy chain of antibody HbnC3t1p2_C6

<400> SEQUENCE: 13

Gln Met Gln Leu Val Gln Ser Gly Pro Glu Val Lys Lys Pro Gly Thr
```

```
1               5                   10                  15

Ser Val Lys Val Ser Cys Lys Ala Ser Gly Phe Thr Phe Ser Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Gly Arg Val Thr Ile Thr Arg Asp Met Ser Thr Arg Thr Ala Tyr
65                  70                  75                  80

Met Glu Leu Ser Ser Leu Arg Ser Glu Asp Thr Ala Met Tyr Tyr Cys
                85                  90                  95

Ala Ala Pro Tyr Cys Ser Ser Thr Arg Cys Tyr Asp Ala Phe Asp Ile
            100                 105                 110

Trp Gly Gln Gly Thr Met Val Thr Val Ser Ser
        115                 120


<210> SEQ ID NO 14
<211> LENGTH: 108
<212> TYPE: PRT
<213> ORGANISM: Homo sapiens
<220> FEATURE:
<223> OTHER INFORMATION: Light chain of antibody HbnC3t1p2_C6

<400> SEQUENCE: 14

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Arg Ser Pro
                85                  90                  95

Trp Thr Phe Gly Gln Gly Thr Lys Val Glu Ile Lys
            100                 105


<210> SEQ ID NO 15
<211> LENGTH: 124
<212> TYPE: PRT
<213> ORGANISM: Homo sapiens
<220> FEATURE:
<223> OTHER INFORMATION: Heavy chain of antibody MnC4t2p1_B3

<400> SEQUENCE: 15

Glu Val Gln Leu Val Glu Ser Gly Gly His Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Gly Gly Ile Leu Asp Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu His Met Arg Ser Leu Arg Thr Asp Asp Thr Ala Leu Tyr Tyr Cys
                85                  90                  95

Ala Lys Asp Leu Arg Arg Gln Asp Tyr Tyr Ala Asp Trp Tyr Phe Asp
            100                 105                 110

Leu Trp Gly Arg Gly Thr Leu Val Thr Val Ser Ser
        115                 120


<210> SEQ ID NO 16
<211> LENGTH: 106
<212> TYPE: PRT
<213> ORGANISM: Homo sapiens
<220> FEATURE:
<223> OTHER INFORMATION: Light chain of antibody MnC4t2p1_B3

<400> SEQUENCE: 16

Asp Ile Gln Met Ile Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Leu Ser Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Phe
                85                  90                  95

Thr Phe Gly Pro Gly Thr Ile Val Asp Val
            100                 105


<210> SEQ ID NO 17
<211> LENGTH: 119
<212> TYPE: PRT
<213> ORGANISM: Homo sapiens
<220> FEATURE:
<223> OTHER INFORMATION: Heavy chain of antibody MnC2t1p1_A3

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Arg Gly Leu Glu Trp Val
        35                  40                  45

Ser Val Ile Tyr Ser Gly Gly Ser Thr Phe Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Pro Glu Asp Thr Ala Val Tyr Tyr Cys Ala
                85                  90                  95

Thr Gly Ala Arg Phe Gly Glu Ser Pro Phe Asp Tyr Trp Gly Gln Gly
            100                 105                 110

Thr Leu Val Thr Val Ser Ser
        115


<210> SEQ ID NO 18
<211> LENGTH: 107
<212> TYPE: PRT
<213> ORGANISM: Homo sapiens
```

<220> FEATURE:
<223> OTHER INFORMATION: Light chain of antibody MnC2t1p1_A3

<400> SEQUENCE: 18

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Ser Phe Pro Gly
85 90 95

Thr Phe Gly Gln Gly Thr Lys Val Glu Ile Lys
100 105

<210> SEQ ID NO 19
<211> LENGTH: 119
<212> TYPE: PRT
<213> ORGANISM: Homo sapiens
<220> FEATURE:
<223> OTHER INFORMATION: Heavy chain of antibody CnC2t1p1_B4

<400> SEQUENCE: 19

Gln Val Gln Leu Val Gln Ser Gly Ala Glu Val Lys Lys Pro Gly Ala
1 5 10 15

Ser Val Lys Val Ser Cys Lys Ala Ser Gly Tyr Thr Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Asn Gly Asn Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Gly Glu Leu Leu Gly Trp Phe Asp Pro Trp Gly Gln Gly
100 105 110

Thr Leu Val Thr Val Ser Ser
115

<210> SEQ ID NO 20
<211> LENGTH: 110
<212> TYPE: PRT
<213> ORGANISM: Homo sapiens
<220> FEATURE:
<223> OTHER INFORMATION: Light chain of antibody CnC2t1p1_B4

<400> SEQUENCE: 20

Gln Ser Ala Leu Thr Gln Pro Ala Ser Val Ser Gly Ser Pro Gly Gln
1 5 10 15

Ser Ile Thr Ile Ser Cys Thr Gly Thr Ser Ser Asp Val Gly Ser Tyr
20 25 30

Asn Leu Val Ser Trp Tyr Gln Gln His Pro Gly Lys Ala Pro Lys Leu
35 40 45

Met Ile Tyr Glu Gly Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Trp Val Phe Gly Gly Gly Thr Lys Leu Thr Val Leu
            100                 105                 110

<210> SEQ ID NO 21
<211> LENGTH: 120
<212> TYPE: PRT
<213> ORGANISM: Homo sapiens
<220> FEATURE:
<223> OTHER INFORMATION: Heavy chain of antibody HbnC3t1p1_F4

<400> SEQUENCE: 21

Gln Val Gln Leu Val Glu Ser Gly Gly Gly Val Val Gln Pro Gly Arg
1               5                   10                  15

Ser Leu Arg Leu Ser Cys Ala Ala Thr Gly Phe Thr Phe Arg Arg Tyr
            20                  25                  30

Gly Met His Trp Val Arg Gln Ala Pro Gly Lys Gly Leu Glu Trp Val
        35                  40                  45

Ala Gly Ile Leu Phe Asp Gly Ser Asn Lys Tyr Tyr Val Asp Ser Val
    50                  55                  60

Lys Gly Arg Phe Thr Ile Ser Arg Asp Ser Ser Arg Asn Thr Leu Tyr
65                  70                  75                  80

Leu Gln Leu Asn Ser Leu Arg Arg Glu Asp Thr Ala Val Tyr Tyr Cys
                85                  90                  95

Ala Lys Gly Gly Asp Tyr Glu Trp Glu Leu Leu Glu Ser Trp Gly Gln
            100                 105                 110

Gly Thr Leu Val Thr Val Ser Ser
        115                 120

<210> SEQ ID NO 22
<211> LENGTH: 107
<212> TYPE: PRT
<213> ORGANISM: Homo sapiens
<220> FEATURE:
<223> OTHER INFORMATION: Light chain of antibody HbnC3t1p1_F4

<400> SEQUENCE: 22

Asp Ile Gln Met Thr Gln Ser Pro Ser Thr Val Ser Ala Ser Val Gly
1               5                   10                  15

Asp Arg Val Thr Ile Thr Cys Arg Ala Ser Gln Ser Ile Asp Asn Trp
            20                  25                  30

Leu Ala Trp Tyr Gln Glu Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Arg Gly Ser Gly Thr Glu Phe Thr Leu Thr Ile Ser Ser Leu Gln Pro
65                  70                  75                  80

Gly Asp Phe Ala Thr Tyr Tyr Cys Gln His Tyr His Ser Phe Pro Leu
                85                  90                  95

Thr Phe Gly Gly Gly Thr Lys Val Asp Ile Lys
            100                 105

<210> SEQ ID NO 23

<211> LENGTH: 126
<212> TYPE: PRT
<213> ORGANISM: Homo sapiens
<220> FEATURE:
<223> OTHER INFORMATION: Heavy chain of antibody HbnC2t1p2_D9

<400> SEQUENCE: 23

Gln Val Gln Leu Val Glu Ser Gly Gly Gly Val Val Gln Pro Gly Arg
1 5 10 15

Ser Leu Arg Leu Ser Cys Ala Ala Ser Gly Phe Thr Phe Ser Ser Tyr
20 25 30

Gly Met His Trp Val Arg Gln Ala Pro Gly Lys Gly Leu Glu Trp Val
35 40 45

Ala Val Ile Trp Tyr Asp Gly Arg Asn Lys Tyr Tyr Val Asp Ser Val
50 55 60

Lys Gly Arg Phe Thr Ile Ser Arg Asp Asn Ser Lys Asn Thr Leu Tyr
65 70 75 80

Leu Gln Ile Ser Ser Leu Arg Ala Glu Asp Thr Ala Val Tyr Tyr Cys
85 90 95

Ala Arg Ala Ala Arg Arg Pro Val Val Thr Asp Thr Met Ala Tyr Tyr
100 105 110

Met Asp Val Trp Gly Lys Gly Thr Thr Val Thr Val Ser Ser
115 120 125

<210> SEQ ID NO 24
<211> LENGTH: 110
<212> TYPE: PRT
<213> ORGANISM: Homo sapiens
<220> FEATURE:
<223> OTHER INFORMATION: Light chain of antibody HbnC2t1p2_D9

<400> SEQUENCE: 24

Glu Ile Val Leu Thr Gln Ser Pro Ala Thr Leu Ser Leu Ser Pro Gly
1 5 10 15

Glu Arg Ala Thr Leu Ser Cys Arg Ala Ser Leu Ser Leu Ser Ser Tyr
20 25 30

Leu Ala Trp Tyr Gln Gln Lys Pro Gly Gln Ala Pro Arg Leu Leu Ile
35 40 45

Tyr Asp Ala Ser Asn Arg Ala Thr Gly Ile Pro Ala Arg Phe Ser Gly
50 55 60

Ser Gly Ser Gly Thr Asp Phe Thr Leu Thr Ile Ser Ser Leu Glu Pro
65 70 75 80

Glu Asp Phe Ala Val Tyr Tyr Cys Gln Gln Arg Ser Asn Trp Pro Pro
85 90 95

Thr Trp Thr Phe Gly Gln Gly Thr Lys Ala Glu Ile Lys Arg
100 105 110

<210> SEQ ID NO 25
<211> LENGTH: 123
<212> TYPE: PRT
<213> ORGANISM: Homo sapiens
<220> FEATURE:
<223> OTHER INFORMATION: Heavy chain of antibody MnC5t2p1_G1

<400> SEQUENCE: 25

Gln Met Gln Leu Val Gln Ser Gly Pro Glu Val Lys Lys Pro Gly Thr
1 5 10 15

Ser Val Lys Val Ser Cys Lys Ala Ser Gly Phe Thr Phe Thr Ser Ser
20 25 30

```
Ala Val Gln Trp Val Arg Gln Ala Arg Gly Gln Arg Leu Glu Trp Ile
        35                  40                  45

Gly Trp Ile Val Val Gly Ser Gly Asn Thr Asp Tyr Ala Gln Lys Phe
    50                  55                  60

Gln Glu Arg Val Thr Ile Thr Arg Asp Val Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala Pro Arg Cys Ser Gly Gly Ser Cys Tyr Asp Gly Phe Asp Ile
            100                 105                 110

Trp Gly Gln Gly Thr Met Val Thr Val Ser Ser
        115                 120


<210> SEQ ID NO 26
<211> LENGTH: 108
<212> TYPE: PRT
<213> ORGANISM: Homo sapiens
<220> FEATURE:
<223> OTHER INFORMATION: Light chain of antibody MnC5t2p1_G1

<400> SEQUENCE: 26

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln His Lys Pro Gly Gln Ala Pro Arg Leu Leu
        35                  40                  45

Ile Cys Gly Ala Ser Ser Arg Ala Thr Gly Ile Pro Asp Arg Phe Ser
    50                  55                  60

Gly Ser Gly Ser Gly Thr Gly Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105


<210> SEQ ID NO 27
<211> LENGTH: 126
<212> TYPE: PRT
<213> ORGANISM: Homo sapiens
<220> FEATURE:
<223> OTHER INFORMATION: Heavy chain of antibody CnC2t1p1_E12

<400> SEQUENCE: 27

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Val Tyr Leu Gln Met Asn Ser Leu Lys Thr Glu Asp Thr Ala Val Tyr
                85                  90                  95

Tyr Cys Thr Arg Val Arg Arg Leu Trp Phe Gly Ser Tyr Tyr Tyr Gly
            100                 105                 110
```

```
Met Asp Val Trp Gly Gln Gly Thr Thr Val Thr Val Ser Ser
        115                 120                 125


<210> SEQ ID NO 28
<211> LENGTH: 112
<212> TYPE: PRT
<213> ORGANISM: Homo sapiens
<220> FEATURE:
<223> OTHER INFORMATION: Light chain of antibody CnC2t1p1_E12

<400> SEQUENCE: 28

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gly Thr Phe Gly Pro Gly Thr Lys Val Asp Ile Lys
            100                 105                 110


<210> SEQ ID NO 29
<211> LENGTH: 126
<212> TYPE: PRT
<213> ORGANISM: Homo sapiens
<220> FEATURE:
<223> OTHER INFORMATION: Heavy chain of antibody CnC2t1p1_D6

<400> SEQUENCE: 29

Glu Val Gln Leu Val Glu Ser Gly Gly Gly Leu Val Gln Pro Gly Arg
1               5                   10                  15

Ser Leu Arg Leu Ser Cys Thr Ala Ser Gly Phe Thr Phe Gly Asp Tyr
            20                  25                  30

Ala Met Ser Trp Phe Arg Gln Ala Pro Gly Lys Gly Leu Glu Trp Val
        35                  40                  45

Gly Phe Ile Arg Ser Lys Ala Tyr Gly Gly Thr Thr Glu Tyr Ala Ala
    50                  55                  60

Ser Val Lys Gly Arg Phe Thr Ile Ser Arg Asp Asp Ser Lys Ser Ile
65                  70                  75                  80

Ala Tyr Leu Gln Met Asn Ser Leu Lys Thr Glu Asp Thr Ala Val Tyr
                85                  90                  95

Tyr Cys Thr Arg Val Arg Arg Leu Trp Phe Gly Ser Tyr Tyr Tyr Gly
            100                 105                 110

Met Asp Val Trp Gly Gln Gly Thr Thr Val Thr Val Ser Ser
        115                 120                 125


<210> SEQ ID NO 30
<211> LENGTH: 112
<212> TYPE: PRT
<213> ORGANISM: Homo sapiens
<220> FEATURE:
<223> OTHER INFORMATION: Light chain of antibody CnC2t1p1_D6

<400> SEQUENCE: 30
```

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Gly Thr Phe Gly Pro Gly Thr Lys Val Asp Ile Lys
            100                 105                 110


<210> SEQ ID NO 31
<211> LENGTH: 119
<212> TYPE: PRT
<213> ORGANISM: Homo sapiens
<220> FEATURE:
<223> OTHER INFORMATION: Heavy chain of antibody MnC2t1p1_C5

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Thr Gly Ala Arg Phe Gly Glu Ser Pro Phe Asp Tyr Trp Gly Gln Gly
            100                 105                 110

Thr Leu Val Thr Val Ser Ser
        115


<210> SEQ ID NO 32
<211> LENGTH: 107
<212> TYPE: PRT
<213> ORGANISM: Homo sapiens
<220> FEATURE:
<223> OTHER INFORMATION: Light chain of antibody MnC2t1p1_C5

<400> SEQUENCE: 32

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Ala Asn Ser Phe Pro Gly
                85                  90                  95

Thr Phe Gly Gln Gly Thr Lys Val Glu Ile Lys
            100                 105


<210> SEQ ID NO 33
<211> LENGTH: 120
<212> TYPE: PRT
<213> ORGANISM: Homo sapiens
<220> FEATURE:
<223> OTHER INFORMATION: Heavy chain of antibody CnC2t1p1_E8

<400> SEQUENCE: 33

Gln Val Gln Leu Val Gln Ser Gly Ala Glu Val Lys Asn Pro Gly Ala
1               5                   10                  15

Ser Val Lys Val Ser Cys Lys Ala Ser Gly Tyr Ile Phe Thr Asn Tyr
            20                  25                  30

Tyr Ile His Trp Val Arg Gln Ala Pro Gly Gln Gly Leu Glu Trp Val
        35                  40                  45

Gly Trp Ile His Ser Leu Ser Gly Gly Thr Ser Tyr Ala Gln Lys Phe
    50                  55                  60

Gln Gly Arg Val Thr Leu Thr Arg Asp Ala Ser Ile Arg Thr Ala Tyr
65                  70                  75                  80

Met Glu Leu Ser Arg Leu Gly Ser Asp Asp Thr Ala Leu Tyr Tyr Cys
                85                  90                  95

Ala Arg Ala Ser Val Ser Thr Ile Thr Asp Phe Asp Tyr Trp Gly Gln
            100                 105                 110

Gly Thr Leu Val Ala Val Ser Ser
        115                 120


<210> SEQ ID NO 34
<211> LENGTH: 110
<212> TYPE: PRT
<213> ORGANISM: Homo sapiens
<220> FEATURE:
<223> OTHER INFORMATION: Light chain of antibody CnC2t1p1_E8

<400> SEQUENCE: 34

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Gly Asp Val Gly Ser Tyr
            20                  25                  30

Asn Leu Val Ser Trp Tyr Gln Gln His Pro Gly Lys Ala Pro Lys Leu
        35                  40                  45

Val Ile Tyr Glu Ala Thr Lys Arg Pro Ser Gly Val Ser Asn Arg Phe
    50                  55                  60

Phe Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Val
                85                  90                  95

Arg Thr Val Val Phe Gly Gly Gly Thr Lys Leu Thr Val Leu
            100                 105                 110


<210> SEQ ID NO 35
<211> LENGTH: 120
<212> TYPE: PRT
<213> ORGANISM: Homo sapiens
<220> FEATURE:
<223> OTHER INFORMATION: Heavy chain of antibody MnC1t3p1_G9
```

<400> SEQUENCE: 35

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Arg Asn Tyr
20 25 30

Ala Met Thr Trp Val Arg Gln Ala Pro Gly Lys Gly Leu Glu Trp Val
35 40 45

Ser Gly Ile Ser Asp Ser Gly Asp Arg Thr Tyr Asn Ala Asp Ser Val
50 55 60

Lys Gly Arg Phe Ser Ile Ser Arg Asp Asn Ser Lys Asn Thr Leu His
65 70 75 80

Leu Gln Met Asn Ser Leu Arg Ala Glu Asp Thr Ala Val Tyr Tyr Cys
85 90 95

Ala Leu Ala Ser Gly Ser Tyr Phe Gly Gly Ala Asn Tyr Trp Gly Gln
100 105 110

Gly Thr Leu Val Thr Val Ser Ser
115 120

<210> SEQ ID NO 36
<211> LENGTH: 109
<212> TYPE: PRT
<213> ORGANISM: Homo sapiens
<220> FEATURE:
<223> OTHER INFORMATION: Light chain of antibody MnC1t3p1_G9

<400> SEQUENCE: 36

Gln Ala Val Val Thr Gln Glu Pro Ser Leu Thr Val Ser Pro Gly Gly
1 5 10 15

Thr Val Thr Leu Thr Cys Gly Ser Ser Thr Gly Pro Val Thr Ser Asp
20 25 30

His Tyr Pro Tyr Trp Phe Gln Gln Lys Pro Gly Gln Ala Pro Thr Thr
35 40 45

Leu Ile Tyr Asp Thr Asn Asn Lys His Ser Trp Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Leu Leu Ser Tyr Thr Gly
85 90 95

Ala Arg Val Phe Gly Gly Gly Thr Lys Leu Thr Val Leu
100 105

<210> SEQ ID NO 37
<211> LENGTH: 125
<212> TYPE: PRT
<213> ORGANISM: Homo sapiens
<220> FEATURE:
<223> OTHER INFORMATION: Heavy chain of antibody HbnC4t1p1_D5

<400> SEQUENCE: 37

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

```
Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Gly Leu Tyr Tyr Cys
                85                  90                  95

Ala Lys Asp Ile Asn Tyr Asp Ser Gly Gly Tyr His Lys Asn Tyr Phe
            100                 105                 110

Asp Tyr Trp Gly Gln Gly Thr Leu Val Thr Val Ser Ser
        115                 120                 125


<210> SEQ ID NO 38
<211> LENGTH: 107
<212> TYPE: PRT
<213> ORGANISM: Homo sapiens
<220> FEATURE:
<223> OTHER INFORMATION: Light chain of antibody HbnC4t1p1_D5

<400> SEQUENCE: 38

Asp Ile Gln Met Thr Gln Ser Pro Ser Ser Leu Ser Ala Ser Val Gly
1               5                   10                  15

Asp Arg Ala Thr Ile Thr Cys Arg Ala Ser Gln Ser Ile Ser Ser Tyr
            20                  25                  30

Leu Asn Trp Tyr Gln Glu Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Leu
                85                  90                  95

Thr Phe Gly Gly Gly Thr Lys Val Glu Ile Lys
            100                 105


<210> SEQ ID NO 39
<211> LENGTH: 122
<212> TYPE: PRT
<213> ORGANISM: Homo sapiens
<220> FEATURE:
<223> OTHER INFORMATION: Heavy chain of antibody CnC2t1p1_B10

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Ser Gly Tyr Asp Ser Ser Gly Tyr Trp Gly Asp Tyr Trp
            100                 105                 110

Gly Gln Gly Thr Leu Val Thr Val Ser Ser
        115                 120
```

```
<210> SEQ ID NO 40
<211> LENGTH: 109
<212> TYPE: PRT
<213> ORGANISM: Homo sapiens
<220> FEATURE:
<223> OTHER INFORMATION: Light chain of antibody CnC2t1p1_B10

<400> SEQUENCE: 40

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Ala Leu Thr Phe Gly Gly Gly Thr Lys Val Glu Ile Lys
            100                 105


<210> SEQ ID NO 41
<211> LENGTH: 120
<212> TYPE: PRT
<213> ORGANISM: Homo sapiens
<220> FEATURE:
<223> OTHER INFORMATION: Heavy chain of antibody CnC2t1p1_G6

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asn Tyr
            20                  25                  30

Tyr Ile His Trp Val Arg Gln Ala Pro Gly Gln Gly Leu Glu Trp Val
        35                  40                  45

Gly Trp Ile His Ser Leu Ser Gly Gly Thr Ser Tyr Ala Gln Lys Phe
    50                  55                  60

Gln Gly Arg Val Thr Leu Thr Arg Asp Ala Pro Ile Arg Thr Ala Tyr
65                  70                  75                  80

Met Glu Leu Ser Gly Leu Gly Ser Asp Asp Thr Ala Val Tyr Tyr Cys
                85                  90                  95

Ala Arg Ala Ser Val Ala Thr Ile Thr Asp Phe Asp Tyr Trp Gly Gln
            100                 105                 110

Gly Thr Leu Val Ala Val Ser Ser
        115                 120


<210> SEQ ID NO 42
<211> LENGTH: 110
<212> TYPE: PRT
<213> ORGANISM: Homo sapiens
<220> FEATURE:
<223> OTHER INFORMATION: Light chain of antibody CnC2t1p1_G6

<400> SEQUENCE: 42

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Gly Asp Ile Gly Ser Tyr
            20                  25                  30
```

```
Asn Leu Val Ser Trp Tyr Gln Gln Tyr Pro Gly Lys Ala Pro Lys Leu
        35                  40                  45

Ile Ile Tyr Glu Ala Ser Lys Arg Pro Ser Gly Val Ser Asn Arg Phe
    50                  55                  60

Phe Ala Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Val
                85                  90                  95

Arg Thr Val Val Phe Gly Gly Gly Thr Lys Leu Thr Val Leu
            100                 105                 110


<210> SEQ ID NO 43
<211> LENGTH: 139
<212> TYPE: PRT
<213> ORGANISM: Homo sapiens
<220> FEATURE:
<223> OTHER INFORMATION: Heavy chain of antibody FnC1t1p2_A5

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asn Thr Gly Tyr Ala Gln Lys Phe
    50                  55                  60

Gln Gly Arg Val Thr Met Thr Arg Asn Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Thr Thr Asp Cys Ser Ser Thr Ser Cys Trp Ser Leu Asp
            100                 105                 110

Phe Trp Ser Gly Tyr Tyr Thr Gly Gly Arg Glu Lys Ile Phe Asp Tyr
        115                 120                 125

Trp Gly Gln Gly Thr Leu Val Thr Val Ser Ser
    130                 135


<210> SEQ ID NO 44
<211> LENGTH: 108
<212> TYPE: PRT
<213> ORGANISM: Homo sapiens
<220> FEATURE:
<223> OTHER INFORMATION: Light chain of antibody FnC1t1p2_A5

<400> SEQUENCE: 44

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
```

```
                85                  90                  95

Gly Thr Phe Gly Gln Gly Thr Lys Val Glu Ile Lys
            100                 105
```

<210> SEQ ID NO 45
<211> LENGTH: 128
<212> TYPE: PRT
<213> ORGANISM: Homo sapiens
<220> FEATURE:
<223> OTHER INFORMATION: Heavy chain of antibody MnC4t2p1_D10

<400> SEQUENCE: 45

```
Gln Leu Gln Val Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Asn
            20                  25                  30

His Tyr Phe Trp Gly Trp Ile Arg Gln Pro Pro Gly Lys Gly Leu Ala
        35                  40                  45

Trp Ile Gly Ser Met His Tyr Ser Gly Ser Thr Tyr Tyr Asn Pro Ser
    50                  55                  60

Leu Lys Ser Arg Val Thr Ile Ser Val Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Gly Val Asn Tyr Tyr Asp Arg Asn Gly Tyr Tyr Arg Asn
            100                 105                 110

Asp Gly Phe Asp Ile Arg Gly Gln Gly Thr Met Val Thr Val Ser Ser
        115                 120                 125
```

<210> SEQ ID NO 46
<211> LENGTH: 107
<212> TYPE: PRT
<213> ORGANISM: Homo sapiens
<220> FEATURE:
<223> OTHER INFORMATION: Light chain of antibody MnC4t2p1_D10

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Glu Gln Lys Pro Gly Lys Ala Pro Lys Arg Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Phe
                85                  90                  95

Thr Phe Gly Pro Gly Thr Arg Val Asp Ile Lys
            100                 105
```

<210> SEQ ID NO 47
<211> LENGTH: 118
<212> TYPE: PRT
<213> ORGANISM: Homo sapiens
<220> FEATURE:
<223> OTHER INFORMATION: Heavy chain of antibody MnC4t2p2_A4

<400> SEQUENCE: 47

```
Gln Val Gln Leu Val Gln Ser Gly Ser Glu Leu Lys Lys Pro Gly Ala
1               5                   10                  15

Ser Val Lys Ile Ser Cys Lys Ala Ser Gly Tyr Ile Phe Ile Asn Tyr
            20                  25                  30

Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Asp Phe
    50                  55                  60

Thr Gly Arg Phe Val Phe Ser Leu Asp Thr Ser Leu Ser Thr Ala Tyr
65                  70                  75                  80

Leu Gln Ile Ser Ser Leu Glu Ala Glu Asp Thr Ala Val Tyr Tyr Cys
                85                  90                  95

Ala Lys Ile Gly Ser Arg Asn Ser Leu Gly Val Trp Gly Gln Gly Thr
            100                 105                 110

Leu Val Thr Val Ser Ala
        115


<210> SEQ ID NO 48
<211> LENGTH: 108
<212> TYPE: PRT
<213> ORGANISM: Homo sapiens
<220> FEATURE:
<223> OTHER INFORMATION: Light chain of antibody MnC4t2p2_A4

<400> SEQUENCE: 48

Glu Ile Val Leu Thr Gln Ser Pro Gly Thr Leu Ser Leu Ser Pro Gly
1               5                   10                  15

Glu Arg Ala Thr Leu Ser Cys Arg Ala Ser His Ser Val Asp Arg Ser
            20                  25                  30

Tyr Leu Ala Trp Tyr Gln Gln Lys Pro Gly Leu Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Leu Tyr Tyr Cys Gln His Phe Gly Thr Ser Ser
                85                  90                  95

Val Thr Phe Gly Arg Gly Thr Arg Leu Glu Ile Lys
            100                 105


<210> SEQ ID NO 49
<211> LENGTH: 128
<212> TYPE: PRT
<213> ORGANISM: Homo sapiens
<220> FEATURE:
<223> OTHER INFORMATION: Heavy chain of antibody MnC4t1p1_A10

<400> SEQUENCE: 49

Gln Leu Gln Val Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Asn
            20                  25                  30

His Tyr Phe Trp Gly Trp Ile Arg Gln Pro Pro Gly Lys Gly Leu Ala
        35                  40                  45

Trp Ile Gly Ser Met His Tyr Ser Gly Ser Thr Tyr Tyr Asn Pro Ser
    50                  55                  60

Leu Lys Ser Arg Val Thr Ile Ser Val Asp Thr Ser Lys Asn Gln Leu
```

```
65                  70                  75                  80

Ser Leu Lys Leu Ser Ser Val Thr Ala Ala Asp Thr Ala Val Tyr Tyr
                85                  90                  95

Cys Ala Arg Gly Val Asn Tyr Tyr Asp Arg Asn Gly Tyr Tyr Arg Asn
            100                 105                 110

Asp Gly Phe Asp Ile Arg Gly Gln Gly Thr Met Val Thr Val Ser Ser
        115                 120                 125


<210> SEQ ID NO 50
<211> LENGTH: 107
<212> TYPE: PRT
<213> ORGANISM: Homo sapiens
<220> FEATURE:
<223> OTHER INFORMATION: Light chain of antibody MnC4t1p1_A10

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Glu Gln Lys Pro Gly Lys Ala Pro Lys Arg Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Phe
                85                  90                  95

Thr Phe Gly Pro Gly Thr Arg Val Asp Ile Lys
            100                 105


<210> SEQ ID NO 51
<211> LENGTH: 124
<212> TYPE: PRT
<213> ORGANISM: Homo sapiens
<220> FEATURE:
<223> OTHER INFORMATION: Heavy chain of antibody MnC4t2p1_E6

<400> SEQUENCE: 51

Glu Val Gln Leu Val Glu Ser Gly Gly His Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Gly Gly Ile Leu Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Arg Ser Leu Arg Thr Asp Asp Thr Ala Leu Tyr Tyr Cys
                85                  90                  95

Ala Lys Asp Leu Arg Arg Gln Asp Tyr Tyr Ala Asp Trp Tyr Phe Asp
            100                 105                 110

Leu Trp Gly Arg Gly Thr Leu Val Thr Val Ser Ser
        115                 120


<210> SEQ ID NO 52
<211> LENGTH: 106
```

<212> TYPE: PRT
<213> ORGANISM: Homo sapiens
<220> FEATURE:
<223> OTHER INFORMATION: Light chain of antibody MnC4t2p1_E6

<400> SEQUENCE: 52

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Leu Ser Ala Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Asn Ser Phe Pro Phe
                85                  90                  95

Thr Phe Gly Pro Gly Thr Lys Val Asp Val
            100                 105
```

<210> SEQ ID NO 53
<211> LENGTH: 122
<212> TYPE: PRT
<213> ORGANISM: Homo sapiens
<220> FEATURE:
<223> OTHER INFORMATION: Heavy chain of antibody MnC4t1p1_A11

<400> SEQUENCE: 53

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Asn Thr Arg Tyr Tyr Thr Asp Ser Val
    50                  55                  60

Met Gly Arg Phe Thr Ile Ser Arg Asp Asn Ala Lys Asn Ser Leu Phe
65                  70                  75                  80

Leu Gln Met Asn Ser Leu Arg Ala Glu Asp Thr Ala Val Tyr Tyr Cys
                85                  90                  95

Ala Ser Ser Lys Gly Phe Cys Ser Gly Gly Ser Cys Ser Asp Tyr Trp
            100                 105                 110

Gly Gln Gly Thr Leu Val Thr Val Ser Ser
        115                 120
```

<210> SEQ ID NO 54
<211> LENGTH: 108
<212> TYPE: PRT
<213> ORGANISM: Homo sapiens
<220> FEATURE:
<223> OTHER INFORMATION: Light chain of antibody MnC4t1p1_A11

<400> SEQUENCE: 54

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
```

```
        35                  40                  45

Ile Tyr Gly Val Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Val Val Tyr Tyr Cys His Gln Tyr Gly Ser Ser Pro
                85                  90                  95

Trp Thr Phe Gly Gln Gly Thr Lys Val Glu Ile Lys
            100                 105


<210> SEQ ID NO 55
<211> LENGTH: 128
<212> TYPE: PRT
<213> ORGANISM: Homo sapiens
<220> FEATURE:
<223> OTHER INFORMATION: Heavy chain of antibody MnC4t2p1_F5

<400> SEQUENCE: 55

Gln Leu Gln Val Gln Glu Ser Gly Pro Gly Leu Val Lys Pro Ser Glu
1               5                   10                  15

Thr Leu Ser Leu Thr Cys Thr Val Ser Gly Ala Ser Ile Ser Ser Asn
            20                  25                  30

His Tyr Phe Trp Gly Trp Ile Arg Gln Pro Pro Gly Lys Gly Leu Ala
        35                  40                  45

Trp Ile Gly Ser Met His Tyr Ser Gly Ser Thr Tyr Tyr Asn Pro Ser
    50                  55                  60

Leu Lys Ser Arg Val Thr Ile Ser Val Asp Thr Ser Lys Asn Gln Leu
65                  70                  75                  80

Ser Leu Lys Leu Ser Ser Val Thr Ala Ala Asp Thr Ala Val Tyr Tyr
                85                  90                  95

Cys Ala Arg Gly Val Asn Tyr Tyr Asp Arg Asn Gly Tyr Tyr Arg Asn
            100                 105                 110

Asp Gly Phe Asp Ile Arg Gly Gln Gly Thr Met Val Thr Val Ser Ser
        115                 120                 125


<210> SEQ ID NO 56
<211> LENGTH: 107
<212> TYPE: PRT
<213> ORGANISM: Homo sapiens
<220> FEATURE:
<223> OTHER INFORMATION: Light chain of antibody MnC4t2p1_F5

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Glu Gln Lys Pro Gly Lys Ala Pro Lys Arg Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Phe
                85                  90                  95

Thr Phe Gly Pro Gly Thr Arg Val Asp Ile Lys
            100                 105
```

```
<210> SEQ ID NO 57
<211> LENGTH: 1288
<212> TYPE: PRT
<213> ORGANISM: Artificial Sequence
<220> FEATURE:
<223> OTHER INFORMATION: Ectodomain of the spike (S) homotrimer of
      SARS-CoV-2 in the prefusion-stabilized-variant of the virus
      isolate Wuhan-Hu-1 as described in Wrapp et al., Science (2022)
      doi: 10.1126/science.abb2507

<400> SEQUENCE: 57

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320

Gln Pro Thr Glu Ser Ile Val Arg Phe Pro Asn Ile Thr Asn Leu Cys
                325                 330                 335

Pro Phe Gly Glu Val Phe Asn Ala Thr Arg Phe Ala Ser Val Tyr Ala
            340                 345                 350
```

```
Trp Asn Arg Lys Arg Ile Ser Asn Cys Val Ala Asp Tyr Ser Val Leu
        355                 360                 365

Tyr Asn Ser Ala Ser Phe Ser Thr Phe Lys Cys Tyr Gly Val Ser Pro
    370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
        435                 440                 445

Tyr Asn Tyr Leu Tyr Arg Leu Phe Arg Lys Ser Asn Leu Lys Pro Phe
    450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
    530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Asp Thr Thr Asp Ala Val
                565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
    610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
                645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Gly Ser Ala Ser Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
            740                 745                 750

Leu Leu Gln Tyr Gly Ser Phe Cys Thr Gln Leu Asn Arg Ala Leu Thr
        755                 760                 765

Gly Ile Ala Val Glu Gln Asp Lys Asn Thr Gln Glu Val Phe Ala Gln
```

```
    770                 775                 780

Val Lys Gln Ile Tyr Lys Thr Pro Pro Ile Lys Asp Phe Gly Gly Phe
785                 790                 795                 800

Asn Phe Ser Gln Ile Leu Pro Asp Pro Ser Lys Pro Ser Lys Arg Ser
                805                 810                 815

Phe Ile Glu Asp Leu Leu Phe Asn Lys Val Thr Leu Ala Asp Ala Gly
            820                 825                 830

Phe Ile Lys Gln Tyr Gly Asp Cys Leu Gly Asp Ile Ala Ala Arg Asp
        835                 840                 845

Leu Ile Cys Ala Gln Lys Phe Asn Gly Leu Thr Val Leu Pro Pro Leu
    850                 855                 860

Leu Thr Asp Glu Met Ile Ala Gln Tyr Thr Ser Ala Leu Leu Ala Gly
865                 870                 875                 880

Thr Ile Thr Ser Gly Trp Thr Phe Gly Ala Gly Ala Ala Leu Gln Ile
                885                 890                 895

Pro Phe Ala Met Gln Met Ala Tyr Arg Phe Asn Gly Ile Gly Val Thr
            900                 905                 910

Gln Asn Val Leu Tyr Glu Asn Gln Lys Leu Ile Ala Asn Gln Phe Asn
        915                 920                 925

Ser Ala Ile Gly Lys Ile Gln Asp Ser Leu Ser Ser Thr Ala Ser Ala
    930                 935                 940

Leu Gly Lys Leu Gln Asp Val Val Asn Gln Asn Ala Gln Ala Leu Asn
945                 950                 955                 960

Thr Leu Val Lys Gln Leu Ser Ser Asn Phe Gly Ala Ile Ser Ser Val
                965                 970                 975

Leu Asn Asp Ile Leu Ser Arg Leu Asp Pro Pro Glu Ala Glu Val Gln
            980                 985                 990

Ile Asp Arg Leu Ile Thr Gly Arg Leu Gln Ser Leu Gln Thr Tyr Val
        995                 1000                1005

Thr Gln Gln Leu Ile Arg Ala Ala Glu Ile Arg Ala Ser Ala Asn Leu
    1010                1015                1020

Ala Ala Thr Lys Met Ser Glu Cys Val Leu Gly Gln Ser Lys Arg Val
1025                1030                1035                1040

Asp Phe Cys Gly Lys Gly Tyr His Leu Met Ser Phe Pro Gln Ser Ala
                1045                1050                1055

Pro His Gly Val Val Phe Leu His Val Thr Tyr Val Pro Ala Gln Glu
            1060                1065                1070

Lys Asn Phe Thr Thr Ala Pro Ala Ile Cys His Asp Gly Lys Ala His
        1075                1080                1085

Phe Pro Arg Glu Gly Val Phe Val Ser Asn Gly Thr His Trp Phe Val
    1090                1095                1100

Thr Gln Arg Asn Phe Tyr Glu Pro Gln Ile Ile Thr Thr Asp Asn Thr
1105                1110                1115                1120

Phe Val Ser Gly Asn Cys Asp Val Val Ile Gly Ile Val Asn Asn Thr
                1125                1130                1135

Val Tyr Asp Pro Leu Gln Pro Glu Leu Asp Ser Phe Lys Glu Glu Leu
            1140                1145                1150

Asp Lys Tyr Phe Lys Asn His Thr Ser Pro Asp Val Asp Leu Gly Asp
        1155                1160                1165

Ile Ser Gly Ile Asn Ala Ser Val Val Asn Ile Gln Lys Glu Ile Asp
    1170                1175                1180

Arg Leu Asn Glu Val Ala Lys Asn Leu Asn Glu Ser Leu Ile Asp Leu
1185                1190                1195                1200
```

```
Gln Glu Leu Gly Lys Tyr Glu Gln Gly Ser Gly Tyr Ile Pro Glu Ala
                1205                1210                1215

Pro Arg Asp Gly Gln Ala Tyr Val Arg Lys Asp Gly Glu Trp Val Leu
            1220                1225                1230

Leu Ser Thr Phe Leu Gly Arg Ser Leu Glu Val Leu Phe Gln Gly Pro
        1235                1240                1245

Gly His His His His His His His His Ser Ala Trp Ser His Pro Gln
    1250                1255                1260

Phe Glu Lys Gly Gly Gly Ser Gly Gly Gly Gly Ser Gly Gly Ser Ala
1265                1270                1275                1280

Trp Ser His Pro Gln Phe Glu Lys
                1285


<210> SEQ ID NO 58
<211> LENGTH: 223
<212> TYPE: PRT
<213> ORGANISM: Severe acute respiratory syndrome-related coronavirus 2
<220> FEATURE:
<223> OTHER INFORMATION: Receptor-binding domain (RBD) of the spike (S)
      protein of SARS-CoV-2 of the virus isolate Wuhan-Hu-1 as described
      in Wrapp et al., Science (2022) doi: 10.1126/science.abb2507

<400> SEQUENCE: 58

Arg Val Gln Pro Thr Glu Ser Ile Val Arg Phe Pro Asn Ile Thr Asn
1               5                   10                  15

Leu Cys Pro Phe Gly Glu Val Phe Asn Ala Thr Arg Phe Ala Ser Val
            20                  25                  30

Tyr Ala Trp Asn Arg Lys Arg Ile Ser Asn Cys Val Ala Asp Tyr Ser
        35                  40                  45

Val Leu Tyr Asn Ser Ala Ser Phe Ser Thr Phe Lys Cys Tyr Gly Val
    50                  55                  60

Ser Pro Thr Lys Leu Asn Asp Leu Cys Phe Thr Asn Val Tyr Ala Asp
65                  70                  75                  80

Ser Phe Val Ile Arg Gly Asp Glu Val Arg Gln Ile Ala Pro Gly Gln
                85                  90                  95

Thr Gly Lys Ile Ala Asp Tyr Asn Tyr Lys Leu Pro Asp Asp Phe Thr
            100                 105                 110

Gly Cys Val Ile Ala Trp Asn Ser Asn Asn Leu Asp Ser Lys Val Gly
        115                 120                 125

Gly Asn Tyr Asn Tyr Leu Tyr Arg Leu Phe Arg Lys Ser Asn Leu Lys
    130                 135                 140

Pro Phe Glu Arg Asp Ile Ser Thr Glu Ile Tyr Gln Ala Gly Ser Thr
145                 150                 155                 160

Pro Cys Asn Gly Val Glu Gly Phe Asn Cys Tyr Phe Pro Leu Gln Ser
                165                 170                 175

Tyr Gly Phe Gln Pro Thr Asn Gly Val Gly Tyr Gln Pro Tyr Arg Val
            180                 185                 190

Val Val Leu Ser Phe Glu Leu Leu His Ala Pro Ala Thr Val Cys Gly
        195                 200                 205

Pro Lys Lys Ser Thr Asn Leu Val Lys Asn Lys Cys Val Asn Phe
    210                 215                 220


<210> SEQ ID NO 59
<211> LENGTH: 8
<212> TYPE: PRT
<213> ORGANISM: Homo sapiens
<220> FEATURE:
```

<223> OTHER INFORMATION: CDR-H1 of HbnC3t1p1_C6

<400> SEQUENCE: 59

Gly Phe Thr Phe Thr Ser Ser Ala
1 5

<210> SEQ ID NO 60
<211> LENGTH: 8
<212> TYPE: PRT
<213> ORGANISM: Homo sapiens
<220> FEATURE:
<223> OTHER INFORMATION: CDR-H2 of HbnC3t1p1_C6

<400> SEQUENCE: 60

Ile Val Val Gly Ser Gly Asn Thr
1 5

<210> SEQ ID NO 61
<211> LENGTH: 16
<212> TYPE: PRT
<213> ORGANISM: Homo sapiens
<220> FEATURE:
<223> OTHER INFORMATION: CDR-H3 of HbnC3t1p1_C6

<400> SEQUENCE: 61

Ala Ala Pro His Cys Ser Ser Thr Ile Cys Tyr Asp Gly Phe Asp Ile
1 5 10 15

<210> SEQ ID NO 62
<211> LENGTH: 7
<212> TYPE: PRT
<213> ORGANISM: Homo sapiens
<220> FEATURE:
<223> OTHER INFORMATION: CDR-L1 of HbnC3t1p1_C6

<400> SEQUENCE: 62

Gln Ser Val Ser Ser Ser Tyr
1 5

<210> SEQ ID NO 63
<211> LENGTH: 3
<212> TYPE: PRT
<213> ORGANISM: Homo sapiens
<220> FEATURE:
<223> OTHER INFORMATION: CDR-L2 of HbnC3t1p1_C6

<400> SEQUENCE: 63

Gly Ala Ser
1

<210> SEQ ID NO 64
<211> LENGTH: 9
<212> TYPE: PRT
<213> ORGANISM: Homo sapiens
<220> FEATURE:
<223> OTHER INFORMATION: CDR-L3 of HbnC3t1p1_C6

<400> SEQUENCE: 64

Gln Gln Tyr Gly Ser Ser Pro Trp Thr
1 5

<210> SEQ ID NO 65
<211> LENGTH: 8
<212> TYPE: PRT
<213> ORGANISM: Homo sapiens
<220> FEATURE:
<223> OTHER INFORMATION: CDR-H1 of HbnC3t1p1_G4

<400> SEQUENCE: 65

Gly Phe Thr Val Ser Ser Asn Tyr
1 5

<210> SEQ ID NO 66
<211> LENGTH: 7
<212> TYPE: PRT
<213> ORGANISM: Homo sapiens
<220> FEATURE:
<223> OTHER INFORMATION: CDR-H2 of HbnC3t1p1_G4

<400> SEQUENCE: 66

Ile Tyr Ser Gly Gly Ser Thr
1 5

<210> SEQ ID NO 67
<211> LENGTH: 11
<212> TYPE: PRT
<213> ORGANISM: Homo sapiens
<220> FEATURE:
<223> OTHER INFORMATION: CDR-H3 of HbnC3t1p1_G4

<400> SEQUENCE: 67

Ala Arg Asp Phe Gly Asp Phe Phe Phe Asp Tyr
1 5 10

<210> SEQ ID NO 68
<211> LENGTH: 6
<212> TYPE: PRT
<213> ORGANISM: Homo sapiens
<220> FEATURE:
<223> OTHER INFORMATION: CDR-L1 of HbnC3t1p1_G4

<400> SEQUENCE: 68

Gln Ser Val Ser Ser Tyr
1 5

<210> SEQ ID NO 69
<211> LENGTH: 3
<212> TYPE: PRT
<213> ORGANISM: Homo sapiens
<220> FEATURE:
<223> OTHER INFORMATION: CDR-L2 of HbnC3t1p1_G4

<400> SEQUENCE: 69

Gly Val Ser
1

<210> SEQ ID NO 70
<211> LENGTH: 9
<212> TYPE: PRT
<213> ORGANISM: Homo sapiens
<220> FEATURE:
<223> OTHER INFORMATION: CDR-L3 of HbnC3t1p1_G4

<400> SEQUENCE: 70

Gln Gln Tyr Gly Ser Ser Pro Arg Thr
1 5

<210> SEQ ID NO 71
<211> LENGTH: 8
<212> TYPE: PRT
<213> ORGANISM: Homo sapiens
<220> FEATURE:
<223> OTHER INFORMATION: CDR-H1 of HbnC3t1p2_B10

<400> SEQUENCE: 71

Gly Phe Ile Val Ser Ser Asn Tyr
1 5

<210> SEQ ID NO 72
<211> LENGTH: 7
<212> TYPE: PRT
<213> ORGANISM: Homo sapiens
<220> FEATURE:
<223> OTHER INFORMATION: CDR-H2 of HbnC3t1p2_B10

<400> SEQUENCE: 72

Ile Tyr Ser Gly Gly Ser Thr
1 5

<210> SEQ ID NO 73
<211> LENGTH: 11
<212> TYPE: PRT
<213> ORGANISM: Homo sapiens
<220> FEATURE:
<223> OTHER INFORMATION: CDR-H3 of HbnC3t1p2_B10

<400> SEQUENCE: 73

Ala Arg Asp Tyr Gly Asp Tyr Phe Phe Asp Tyr
1 5 10

<210> SEQ ID NO 74
<211> LENGTH: 6
<212> TYPE: PRT
<213> ORGANISM: Homo sapiens
<220> FEATURE:
<223> OTHER INFORMATION: CDR-L1 of HbnC3t1p2_B10

<400> SEQUENCE: 74

Gln Ser Val Ser Ser Tyr
1 5

<210> SEQ ID NO 75
<211> LENGTH: 3
<212> TYPE: PRT
<213> ORGANISM: Homo sapiens
<220> FEATURE:
<223> OTHER INFORMATION: CDR-L2 of HbnC3t1p2_B10

<400> SEQUENCE: 75

Gly Ala Ser
1

<210> SEQ ID NO 76
<211> LENGTH: 9
<212> TYPE: PRT
<213> ORGANISM: Homo sapiens
<220> FEATURE:
<223> OTHER INFORMATION: CDR-L3 of HbnC3t1p2_B10

<400> SEQUENCE: 76

Gln Gln Tyr Gly Ser Ser Pro Arg Thr
1 5

<210> SEQ ID NO 77
<211> LENGTH: 8
<212> TYPE: PRT
<213> ORGANISM: Homo sapiens
<220> FEATURE:
<223> OTHER INFORMATION: CDR-H1 of MnC2t2p1_C11

<400> SEQUENCE: 77

```
Gly Gly Thr Phe Ser Arg Tyr Thr
1               5


<210> SEQ ID NO 78
<211> LENGTH: 8
<212> TYPE: PRT
<213> ORGANISM: Homo sapiens
<220> FEATURE:
<223> OTHER INFORMATION: CDR-H2 of MnC2t2p1_C11

<400> SEQUENCE: 78

Ile Ile Pro Ile Leu Asp Ile Ala
1               5


<210> SEQ ID NO 79
<211> LENGTH: 23
<212> TYPE: PRT
<213> ORGANISM: Homo sapiens
<220> FEATURE:
<223> OTHER INFORMATION: CDR-H3 of MnC2t2p1_C11

<400> SEQUENCE: 79

Ala Arg Glu Gly Gly Leu Asp Tyr Phe Gly Ser Arg Asn Ser Gly Trp
1               5                   10                  15

Thr Tyr Thr Trp Phe Asp Pro
            20


<210> SEQ ID NO 80
<211> LENGTH: 6
<212> TYPE: PRT
<213> ORGANISM: Homo sapiens
<220> FEATURE:
<223> OTHER INFORMATION: CDR-L1 of MnC2t2p1_C11

<400> SEQUENCE: 80

Gln Asn Ile Ser Ser Tyr
1               5


<210> SEQ ID NO 81
<211> LENGTH: 3
<212> TYPE: PRT
<213> ORGANISM: Homo sapiens
<220> FEATURE:
<223> OTHER INFORMATION: CDR-L2 of MnC2t2p1_C11

<400> SEQUENCE: 81

Ala Ala Ser
1


<210> SEQ ID NO 82
<211> LENGTH: 9
<212> TYPE: PRT
<213> ORGANISM: Homo sapiens
<220> FEATURE:
<223> OTHER INFORMATION: CDR-L3 of MnC2t2p1_C11

<400> SEQUENCE: 82

Gln Gln Ser Tyr Ser Thr Leu Tyr Ser
1               5


<210> SEQ ID NO 83
<211> LENGTH: 8
<212> TYPE: PRT
<213> ORGANISM: Homo sapiens
<220> FEATURE:
<223> OTHER INFORMATION: CDR-H1 of FnC1t2p1_D4
```

<400> SEQUENCE: 83

Gly Tyr Thr Phe Leu Arg Phe Ala
1 5

<210> SEQ ID NO 84
<211> LENGTH: 8
<212> TYPE: PRT
<213> ORGANISM: Homo sapiens
<220> FEATURE:
<223> OTHER INFORMATION: CDR-H2 of FnC1t2p1_D4

<400> SEQUENCE: 84

Ile Asp Thr Asn Thr Gly Thr Pro
1 5

<210> SEQ ID NO 85
<211> LENGTH: 11
<212> TYPE: PRT
<213> ORGANISM: Homo sapiens
<220> FEATURE:
<223> OTHER INFORMATION: CDR-H3 of FnC1t2p1_D4

<400> SEQUENCE: 85

Ala Arg Ser Leu Arg Gly Ala Asn Leu Val Pro
1 5 10

<210> SEQ ID NO 86
<211> LENGTH: 6
<212> TYPE: PRT
<213> ORGANISM: Homo sapiens
<220> FEATURE:
<223> OTHER INFORMATION: CDR-L1 of FnC1t2p1_D4

<400> SEQUENCE: 86

Gln Asp Val Ser Asn Tyr
1 5

<210> SEQ ID NO 87
<211> LENGTH: 3
<212> TYPE: PRT
<213> ORGANISM: Homo sapiens
<220> FEATURE:
<223> OTHER INFORMATION: CDR-L2 of FnC1t2p1_D4

<400> SEQUENCE: 87

Asp Ala Phe
1

<210> SEQ ID NO 88
<211> LENGTH: 9
<212> TYPE: PRT
<213> ORGANISM: Homo sapiens
<220> FEATURE:
<223> OTHER INFORMATION: CDR-L3 of FnC1t2p1_D4

<400> SEQUENCE: 88

Gln Gln Tyr Asp Asn Leu Pro Leu Thr
1 5

<210> SEQ ID NO 89
<211> LENGTH: 8
<212> TYPE: PRT
<213> ORGANISM: Homo sapiens
<220> FEATURE:
<223> OTHER INFORMATION: CDR-H1 of FnC1t2p1_G5

<400> SEQUENCE: 89

Gly Tyr Thr Phe Leu Arg Phe Ala
1 5

<210> SEQ ID NO 90
<211> LENGTH: 8
<212> TYPE: PRT
<213> ORGANISM: Homo sapiens
<220> FEATURE:
<223> OTHER INFORMATION: CDR-H2 of FnC1t2p1_G5

<400> SEQUENCE: 90

Ile Asp Thr Asn Thr Gly Thr Pro
1 5

<210> SEQ ID NO 91
<211> LENGTH: 11
<212> TYPE: PRT
<213> ORGANISM: Homo sapiens
<220> FEATURE:
<223> OTHER INFORMATION: CDR-H3 of FnC1t2p1_G5

<400> SEQUENCE: 91

Ala Arg Ser Leu Arg Gly Ala Asn Leu Val Pro
1 5 10

<210> SEQ ID NO 92
<211> LENGTH: 6
<212> TYPE: PRT
<213> ORGANISM: Homo sapiens
<220> FEATURE:
<223> OTHER INFORMATION: CDR-L1 of FnC1t2p1_G5

<400> SEQUENCE: 92

Gln Asp Val Ser Asn Tyr
1 5

<210> SEQ ID NO 93
<211> LENGTH: 3
<212> TYPE: PRT
<213> ORGANISM: Homo sapiens
<220> FEATURE:
<223> OTHER INFORMATION: CDR-L2 of FnC1t2p1_G5

<400> SEQUENCE: 93

Asp Ala Phe
1

<210> SEQ ID NO 94
<211> LENGTH: 9
<212> TYPE: PRT
<213> ORGANISM: Homo sapiens
<220> FEATURE:
<223> OTHER INFORMATION: CDR-L3 of FnC1t2p1_G5

<400> SEQUENCE: 94

Gln Gln Tyr Asp Asn Leu Pro Leu Thr
1 5

<210> SEQ ID NO 95
<211> LENGTH: 8
<212> TYPE: PRT
<213> ORGANISM: Homo sapiens
<220> FEATURE:
<223> OTHER INFORMATION: CDR-H1 of HbnC3t1p2_C6

<400> SEQUENCE: 95

Gly Phe Thr Phe Ser Ser Ser Ala
1 5

<210> SEQ ID NO 96
<211> LENGTH: 8
<212> TYPE: PRT
<213> ORGANISM: Homo sapiens
<220> FEATURE:
<223> OTHER INFORMATION: CDR-H2 of HbnC3t1p2_C6

<400> SEQUENCE: 96

Ile Val Val Gly Ser Gly Asn Thr
1 5

<210> SEQ ID NO 97
<211> LENGTH: 16
<212> TYPE: PRT
<213> ORGANISM: Homo sapiens
<220> FEATURE:
<223> OTHER INFORMATION: CDR-H3 of HbnC3t1p2_C6

<400> SEQUENCE: 97

Ala Ala Pro Tyr Cys Ser Ser Thr Arg Cys Tyr Asp Ala Phe Asp Ile
1 5 10 15

<210> SEQ ID NO 98
<211> LENGTH: 7
<212> TYPE: PRT
<213> ORGANISM: Homo sapiens
<220> FEATURE:
<223> OTHER INFORMATION: CDR-L1 of HbnC3t1p2_C6

<400> SEQUENCE: 98

Gln Ser Val Ser Ser Ser Tyr
1 5

<210> SEQ ID NO 99
<211> LENGTH: 3
<212> TYPE: PRT
<213> ORGANISM: Homo sapiens
<220> FEATURE:
<223> OTHER INFORMATION: CDR-L2 of HbnC3t1p2_C6

<400> SEQUENCE: 99

Gly Ala Ser
1

<210> SEQ ID NO 100
<211> LENGTH: 9
<212> TYPE: PRT
<213> ORGANISM: Homo sapiens
<220> FEATURE:
<223> OTHER INFORMATION: CDR-L3 of HbnC3t1p2_C6

<400> SEQUENCE: 100

Gln Gln Tyr Gly Arg Ser Pro Trp Thr
1 5

<210> SEQ ID NO 101
<211> LENGTH: 8
<212> TYPE: PRT
<213> ORGANISM: Homo sapiens
<220> FEATURE:
<223> OTHER INFORMATION: CDR-H1 of MnC4t2p1_B3

<400> SEQUENCE: 101

Gly Phe Thr Phe Asp Asp Tyr Ala
1 5

<210> SEQ ID NO 102
<211> LENGTH: 8
<212> TYPE: PRT
<213> ORGANISM: Homo sapiens
<220> FEATURE:
<223> OTHER INFORMATION: CDR-H2 of MnC4t2p1_B3

<400> SEQUENCE: 102

Ile Ser Trp Asn Gly Gly Ile Leu
1 5

<210> SEQ ID NO 103
<211> LENGTH: 17
<212> TYPE: PRT
<213> ORGANISM: Homo sapiens
<220> FEATURE:
<223> OTHER INFORMATION: CDR-H3 of MnC4t2p1_B3

<400> SEQUENCE: 103

Ala Lys Asp Leu Arg Arg Gln Asp Tyr Tyr Ala Asp Trp Tyr Phe Asp
1 5 10 15

Leu

<210> SEQ ID NO 104
<211> LENGTH: 6
<212> TYPE: PRT
<213> ORGANISM: Homo sapiens
<220> FEATURE:
<223> OTHER INFORMATION: CDR-L1 of MnC4t2p1_B3

<400> SEQUENCE: 104

Gln Gly Ile Ser Ser Trp
1 5

<210> SEQ ID NO 105
<211> LENGTH: 3
<212> TYPE: PRT
<213> ORGANISM: Homo sapiens
<220> FEATURE:
<223> OTHER INFORMATION: CDR-L2 of MnC4t2p1_B3

<400> SEQUENCE: 105

Ala Ala Ser
1

<210> SEQ ID NO 106
<211> LENGTH: 9
<212> TYPE: PRT
<213> ORGANISM: Homo sapiens
<220> FEATURE:
<223> OTHER INFORMATION: CDR-L3 of MnC4t2p1_B3

<400> SEQUENCE: 106

Gln Gln Gly Asn Ser Phe Pro Phe Thr
1 5

<210> SEQ ID NO 107
<211> LENGTH: 8
<212> TYPE: PRT
<213> ORGANISM: Homo sapiens
<220> FEATURE:
<223> OTHER INFORMATION: CDR-H1 of MnC2t1p1_A3

<400> SEQUENCE: 107

Gly Phe Thr Val Ser Ser Asn Tyr
1 5

<210> SEQ ID NO 108
<211> LENGTH: 7
<212> TYPE: PRT
<213> ORGANISM: Homo sapiens
<220> FEATURE:
<223> OTHER INFORMATION: CDR-H2 of MnC2t1p1_A3

<400> SEQUENCE: 108

Ile Tyr Ser Gly Gly Ser Thr
1 5

<210> SEQ ID NO 109
<211> LENGTH: 13
<212> TYPE: PRT
<213> ORGANISM: Homo sapiens
<220> FEATURE:
<223> OTHER INFORMATION: CDR-H3 of MnC2t1p1_A3

<400> SEQUENCE: 109

Ala Thr Gly Ala Arg Phe Gly Glu Ser Pro Phe Asp Tyr
1 5 10

<210> SEQ ID NO 110
<211> LENGTH: 6
<212> TYPE: PRT
<213> ORGANISM: Homo sapiens
<220> FEATURE:
<223> OTHER INFORMATION: CDR-L1 of MnC2t1p1_A3

<400> SEQUENCE: 110

Gln Gly Ile Ser Ser Trp
1 5

<210> SEQ ID NO 111
<211> LENGTH: 3
<212> TYPE: PRT
<213> ORGANISM: Homo sapiens
<220> FEATURE:
<223> OTHER INFORMATION: CDR-L2 of MnC2t1p1_A3

<400> SEQUENCE: 111

Ala Ala Ser
1

<210> SEQ ID NO 112
<211> LENGTH: 9
<212> TYPE: PRT
<213> ORGANISM: Homo sapiens
<220> FEATURE:
<223> OTHER INFORMATION: CDR-L3 of MnC2t1p1_A3

<400> SEQUENCE: 112

Gln Gln Ala Asn Ser Phe Pro Gly Thr
1 5

<210> SEQ ID NO 113
<211> LENGTH: 8
<212> TYPE: PRT
<213> ORGANISM: Homo sapiens
<220> FEATURE:
<223> OTHER INFORMATION: CDR-H1 of CnC2t1p1_B4

<400> SEQUENCE: 113

Gly Tyr Thr Phe Thr Ser Tyr Gly
1 5

<210> SEQ ID NO 114
<211> LENGTH: 8
<212> TYPE: PRT
<213> ORGANISM: Homo sapiens
<220> FEATURE:
<223> OTHER INFORMATION: CDR-H2 of CnC2t1p1_B4

<400> SEQUENCE: 114

Ile Ser Ala Tyr Asn Gly Asn Thr
1 5

<210> SEQ ID NO 115
<211> LENGTH: 12
<212> TYPE: PRT
<213> ORGANISM: Homo sapiens
<220> FEATURE:
<223> OTHER INFORMATION: CDR-H3 of CnC2t1p1_B4

<400> SEQUENCE: 115

Ala Arg Asp Gly Glu Leu Leu Gly Trp Phe Asp Pro
1 5 10

<210> SEQ ID NO 116
<211> LENGTH: 9
<212> TYPE: PRT
<213> ORGANISM: Homo sapiens
<220> FEATURE:
<223> OTHER INFORMATION: CDR-L1 of CnC2t1p1_B4

<400> SEQUENCE: 116

Ser Ser Asp Val Gly Ser Tyr Asn Leu
1 5

<210> SEQ ID NO 117
<211> LENGTH: 3
<212> TYPE: PRT
<213> ORGANISM: Homo sapiens
<220> FEATURE:
<223> OTHER INFORMATION: CDR-L2 of CnC2t1p1_B4

<400> SEQUENCE: 117

Glu Gly Ser
1

<210> SEQ ID NO 118
<211> LENGTH: 10
<212> TYPE: PRT
<213> ORGANISM: Homo sapiens
<220> FEATURE:
<223> OTHER INFORMATION: CDR-L3 of CnC2t1p1_B4

<400> SEQUENCE: 118

Cys Ser Tyr Ala Gly Ser Ser Thr Trp Val
1 5 10

<210> SEQ ID NO 119
<211> LENGTH: 8
<212> TYPE: PRT
<213> ORGANISM: Homo sapiens
<220> FEATURE:
<223> OTHER INFORMATION: CDR-H1 of HbnC3t1p1_F4

<400> SEQUENCE: 119

Gly Phe Thr Phe Arg Arg Tyr Gly 1 5

<210> SEQ ID NO 120
<211> LENGTH: 8
<212> TYPE: PRT
<213> ORGANISM: Homo sapiens
<220> FEATURE:
<223> OTHER INFORMATION: CDR-H2 of HbnC3t1p1_F4

<400> SEQUENCE: 120

Ile Leu Phe Asp Gly Ser Asn Lys
1 5

<210> SEQ ID NO 121
<211> LENGTH: 13
<212> TYPE: PRT
<213> ORGANISM: Homo sapiens
<220> FEATURE:
<223> OTHER INFORMATION: CDR-H3 of HbnC3t1p1_F4

<400> SEQUENCE: 121

Ala Lys Gly Gly Asp Tyr Glu Trp Glu Leu Leu Glu Ser
1 5 10

<210> SEQ ID NO 122
<211> LENGTH: 6
<212> TYPE: PRT
<213> ORGANISM: Homo sapiens
<220> FEATURE:
<223> OTHER INFORMATION: CDR-L1 of HbnC3t1p1_F4

<400> SEQUENCE: 122

Gln Ser Ile Asp Asn Trp
1 5

<210> SEQ ID NO 123
<211> LENGTH: 3
<212> TYPE: PRT
<213> ORGANISM: Homo sapiens
<220> FEATURE:
<223> OTHER INFORMATION: CDR-L2 of HbnC3t1p1_F4

<400> SEQUENCE: 123

Lys Ala Ser
1

<210> SEQ ID NO 124
<211> LENGTH: 9
<212> TYPE: PRT
<213> ORGANISM: Homo sapiens
<220> FEATURE:
<223> OTHER INFORMATION: CDR-L3 of HbnC3t1p1_F4

<400> SEQUENCE: 124

Gln His Tyr His Ser Phe Pro Leu Thr
1 5

<210> SEQ ID NO 125
<211> LENGTH: 8
<212> TYPE: PRT
<213> ORGANISM: Homo sapiens
<220> FEATURE:
<223> OTHER INFORMATION: CDR-H1 of HbnC2t1p2_D9

<400> SEQUENCE: 125

Gly Phe Thr Phe Ser Ser Tyr Gly
1 5

<210> SEQ ID NO 126
<211> LENGTH: 8
<212> TYPE: PRT
<213> ORGANISM: Homo sapiens
<220> FEATURE:
<223> OTHER INFORMATION: CDR-H2 of HbnC2t1p2_D9

<400> SEQUENCE: 126

Ile Trp Tyr Asp Gly Arg Asn Lys
1               5

<210> SEQ ID NO 127
<211> LENGTH: 19
<212> TYPE: PRT
<213> ORGANISM: Homo sapiens
<220> FEATURE:
<223> OTHER INFORMATION: CDR-H3 of HbnC2t1p2_D9

<400> SEQUENCE: 127

Ala Arg Ala Ala Arg Arg Pro Val Val Thr Asp Thr Met Ala Tyr Tyr
1               5                   10                  15

Met Asp Val

<210> SEQ ID NO 128
<211> LENGTH: 6
<212> TYPE: PRT
<213> ORGANISM: Homo sapiens
<220> FEATURE:
<223> OTHER INFORMATION: CDR-L1 of HbnC2t1p2_D9

<400> SEQUENCE: 128

Leu Ser Leu Ser Ser Tyr
1               5

<210> SEQ ID NO 129
<211> LENGTH: 3
<212> TYPE: PRT
<213> ORGANISM: Homo sapiens
<220> FEATURE:
<223> OTHER INFORMATION: CDR-L2 of HbnC2t1p2_D9

<400> SEQUENCE: 129

Asp Ala Ser
1

<210> SEQ ID NO 130
<211> LENGTH: 11
<212> TYPE: PRT
<213> ORGANISM: Homo sapiens
<220> FEATURE:
<223> OTHER INFORMATION: CDR-L3 of HbnC2t1p2_D9

<400> SEQUENCE: 130

Gln Gln Arg Ser Asn Trp Pro Pro Thr Trp Thr
1               5                   10

<210> SEQ ID NO 131
<211> LENGTH: 8
<212> TYPE: PRT
<213> ORGANISM: Homo sapiens
<220> FEATURE:
<223> OTHER INFORMATION: CDR-H1 of MnC5t2p1_G1

<400> SEQUENCE: 131

Gly Phe Thr Phe Thr Ser Ser Ala 1 5

<210> SEQ ID NO 132
<211> LENGTH: 8
<212> TYPE: PRT
<213> ORGANISM: Homo sapiens
<220> FEATURE:
<223> OTHER INFORMATION: CDR-H2 of MnC5t2p1_G1

<400> SEQUENCE: 132

Ile Val Val Gly Ser Gly Asn Thr
1 5

<210> SEQ ID NO 133
<211> LENGTH: 16
<212> TYPE: PRT
<213> ORGANISM: Homo sapiens
<220> FEATURE:
<223> OTHER INFORMATION: CDR-H3 of MnC5t2p1_G1

<400> SEQUENCE: 133

Ala Ala Pro Arg Cys Ser Gly Gly Ser Cys Tyr Asp Gly Phe Asp Ile
1 5 10 15

<210> SEQ ID NO 134
<211> LENGTH: 7
<212> TYPE: PRT
<213> ORGANISM: Homo sapiens
<220> FEATURE:
<223> OTHER INFORMATION: CDR-L1 of MnC5t2p1_G1

<400> SEQUENCE: 134

Gln Ser Val Ser Ser Ser Tyr
1 5

<210> SEQ ID NO 135
<211> LENGTH: 3
<212> TYPE: PRT
<213> ORGANISM: Homo sapiens
<220> FEATURE:
<223> OTHER INFORMATION: CDR-L2 of MnC5t2p1_G1

<400> SEQUENCE: 135

Gly Ala Ser
1

<210> SEQ ID NO 136
<211> LENGTH: 9
<212> TYPE: PRT
<213> ORGANISM: Homo sapiens
<220> FEATURE:
<223> OTHER INFORMATION: CDR-L3 of MnC5t2p1_G1

<400> SEQUENCE: 136

Gln Gln Tyr Gly Ser Ser Pro Trp Thr
1 5

<210> SEQ ID NO 137
<211> LENGTH: 8
<212> TYPE: PRT
<213> ORGANISM: Homo sapiens
<220> FEATURE:
<223> OTHER INFORMATION: CDR-H1 of CnC2t1p1_E12

<400> SEQUENCE: 137

Gly Phe Thr Phe Gly Asp Tyr Ala
1 5

<210> SEQ ID NO 138
<211> LENGTH: 10
<212> TYPE: PRT
<213> ORGANISM: Homo sapiens
<220> FEATURE:
<223> OTHER INFORMATION: CDR-H2 of CnC2t1p1_E12

<400> SEQUENCE: 138

Ile Arg Ser Lys Ala Tyr Gly Gly Thr Thr
1 5 10

<210> SEQ ID NO 139
<211> LENGTH: 17
<212> TYPE: PRT
<213> ORGANISM: Homo sapiens
<220> FEATURE:
<223> OTHER INFORMATION: CDR-H3 of CnC2t1p1_E12

<400> SEQUENCE: 139

Thr Arg Val Arg Arg Leu Trp Phe Gly Ser Tyr Tyr Tyr Gly Met Asp
1 5 10 15

Val

<210> SEQ ID NO 140
<211> LENGTH: 11
<212> TYPE: PRT
<213> ORGANISM: Homo sapiens
<220> FEATURE:
<223> OTHER INFORMATION: CDR-L1 of CnC2t1p1_E12

<400> SEQUENCE: 140

Gln Ser Leu Leu His Ser Asn Gly Tyr Asn Tyr
1 5 10

<210> SEQ ID NO 141
<211> LENGTH: 3
<212> TYPE: PRT
<213> ORGANISM: Homo sapiens
<220> FEATURE:
<223> OTHER INFORMATION: CDR-L2 of CnC2t1p1_E12

<400> SEQUENCE: 141

Leu Gly Ser
1

<210> SEQ ID NO 142
<211> LENGTH: 9
<212> TYPE: PRT
<213> ORGANISM: Homo sapiens
<220> FEATURE:
<223> OTHER INFORMATION: CDR-L3 of CnC2t1p1_E12

<400> SEQUENCE: 142

Met Gln Ala Leu Gln Thr Pro Gly Thr
1 5

<210> SEQ ID NO 143
<211> LENGTH: 8
<212> TYPE: PRT
<213> ORGANISM: Homo sapiens
<220> FEATURE:
<223> OTHER INFORMATION: CDR-H1 of CnC2t1p1_D6

<400> SEQUENCE: 143

Gly Phe Thr Phe Gly Asp Tyr Ala 1 5

<210> SEQ ID NO 144
<211> LENGTH: 10
<212> TYPE: PRT
<213> ORGANISM: Homo sapiens
<220> FEATURE:
<223> OTHER INFORMATION: CDR-H2 of CnC2t1p1_D6

<400> SEQUENCE: 144

Ile Arg Ser Lys Ala Tyr Gly Gly Thr Thr
1 5 10

<210> SEQ ID NO 145
<211> LENGTH: 17
<212> TYPE: PRT
<213> ORGANISM: Homo sapiens
<220> FEATURE:
<223> OTHER INFORMATION: CDR-H3 of CnC2t1p1_D6

<400> SEQUENCE: 145

Thr Arg Val Arg Arg Leu Trp Phe Gly Ser Tyr Tyr Tyr Gly Met Asp
1 5 10 15

Val

<210> SEQ ID NO 146
<211> LENGTH: 11
<212> TYPE: PRT
<213> ORGANISM: Homo sapiens
<220> FEATURE:
<223> OTHER INFORMATION: CDR-L1 of CnC2t1p1_D6

<400> SEQUENCE: 146

Gln Ser Leu Leu His Ser Asn Gly Tyr Asn Tyr
1 5 10

<210> SEQ ID NO 147
<211> LENGTH: 3
<212> TYPE: PRT
<213> ORGANISM: Homo sapiens
<220> FEATURE:
<223> OTHER INFORMATION: CDR-L2 of CnC2t1p1_D6

<400> SEQUENCE: 147

Leu Gly Ser
1

<210> SEQ ID NO 148
<211> LENGTH: 9
<212> TYPE: PRT
<213> ORGANISM: Homo sapiens
<220> FEATURE:
<223> OTHER INFORMATION: CDR-L3 of CnC2t1p1_D6

<400> SEQUENCE: 148

Met Gln Ala Leu Gln Thr Pro Gly Thr
1 5

<210> SEQ ID NO 149
<211> LENGTH: 8
<212> TYPE: PRT
<213> ORGANISM: Homo sapiens
<220> FEATURE:
<223> OTHER INFORMATION: CDR-H1 of MnC2t1p1_C5

<400> SEQUENCE: 149

Gly Phe Thr Val Ser Ser Asn Tyr
1 5

<210> SEQ ID NO 150
<211> LENGTH: 7
<212> TYPE: PRT
<213> ORGANISM: Homo sapiens
<220> FEATURE:
<223> OTHER INFORMATION: CDR-H2 of MnC2t1p1_C5

<400> SEQUENCE: 150

Ile Tyr Ser Gly Gly Ser Thr
1 5

<210> SEQ ID NO 151
<211> LENGTH: 13
<212> TYPE: PRT
<213> ORGANISM: Homo sapiens
<220> FEATURE:
<223> OTHER INFORMATION: CDR-H3 of MnC2t1p1_C5

<400> SEQUENCE: 151

Ala Thr Gly Ala Arg Phe Gly Glu Ser Pro Phe Asp Tyr
1 5 10

<210> SEQ ID NO 152
<211> LENGTH: 6
<212> TYPE: PRT
<213> ORGANISM: Homo sapiens
<220> FEATURE:
<223> OTHER INFORMATION: CDR-L1 of MnC2t1p1_C5

<400> SEQUENCE: 152

Gln Gly Ile Ser Ser Trp
1 5

<210> SEQ ID NO 153
<211> LENGTH: 3
<212> TYPE: PRT
<213> ORGANISM: Homo sapiens
<220> FEATURE:
<223> OTHER INFORMATION: CDR-L2 of MnC2t1p1_C5

<400> SEQUENCE: 153

Ala Ala Ser
1

<210> SEQ ID NO 154
<211> LENGTH: 9
<212> TYPE: PRT
<213> ORGANISM: Homo sapiens
<220> FEATURE:
<223> OTHER INFORMATION: CDR-L3 of MnC2t1p1_C5

<400> SEQUENCE: 154

Gln Gln Ala Asn Ser Phe Pro Gly Thr
1 5

<210> SEQ ID NO 155
<211> LENGTH: 8
<212> TYPE: PRT
<213> ORGANISM: Homo sapiens
<220> FEATURE:
<223> OTHER INFORMATION: CDR-H1 of CnC2t1p1_E8

<400> SEQUENCE: 155

Gly Tyr Ile Phe Thr Asn Tyr Tyr 1 5

<210> SEQ ID NO 156
<211> LENGTH: 8
<212> TYPE: PRT
<213> ORGANISM: Homo sapiens
<220> FEATURE:
<223> OTHER INFORMATION: CDR-H2 of CnC2t1p1_E8

<400> SEQUENCE: 156

Ile His Ser Leu Ser Gly Gly Thr
1 5

<210> SEQ ID NO 157
<211> LENGTH: 13
<212> TYPE: PRT
<213> ORGANISM: Homo sapiens
<220> FEATURE:
<223> OTHER INFORMATION: CDR-H3 of CnC2t1p1_E8

<400> SEQUENCE: 157

Ala Arg Ala Ser Val Ser Thr Ile Thr Asp Phe Asp Tyr
1 5 10

<210> SEQ ID NO 158
<211> LENGTH: 9
<212> TYPE: PRT
<213> ORGANISM: Homo sapiens
<220> FEATURE:
<223> OTHER INFORMATION: CDR-L1 of CnC2t1p1_E8

<400> SEQUENCE: 158

Ser Gly Asp Val Gly Ser Tyr Asn Leu
1 5

<210> SEQ ID NO 159
<211> LENGTH: 3
<212> TYPE: PRT
<213> ORGANISM: Homo sapiens
<220> FEATURE:
<223> OTHER INFORMATION: CDR-L2 of CnC2t1p1_E8

<400> SEQUENCE: 159

Glu Ala Thr
1

<210> SEQ ID NO 160
<211> LENGTH: 10
<212> TYPE: PRT
<213> ORGANISM: Homo sapiens
<220> FEATURE:
<223> OTHER INFORMATION: CDR-L3 of CnC2t1p1_E8

<400> SEQUENCE: 160

Cys Ser Tyr Ala Gly Val Arg Thr Val Val
1 5 10

<210> SEQ ID NO 161
<211> LENGTH: 8
<212> TYPE: PRT
<213> ORGANISM: Homo sapiens
<220> FEATURE:
<223> OTHER INFORMATION: CDR-H1 of MnC1t3p1_G9

<400> SEQUENCE: 161

Gly Phe Thr Phe Arg Asn Tyr Ala
1 5

<210> SEQ ID NO 162
<211> LENGTH: 8
<212> TYPE: PRT
<213> ORGANISM: Homo sapiens
<220> FEATURE:
<223> OTHER INFORMATION: CDR-H2 of MnC1t3p1_G9

<400> SEQUENCE: 162

Ile Ser Asp Ser Gly Asp Arg Thr
1 5

<210> SEQ ID NO 163
<211> LENGTH: 13
<212> TYPE: PRT
<213> ORGANISM: Homo sapiens
<220> FEATURE:
<223> OTHER INFORMATION: CDR-H3 of MnC1t3p1_G9

<400> SEQUENCE: 163

Ala Leu Ala Ser Gly Ser Tyr Phe Gly Gly Ala Asn Tyr
1 5 10

<210> SEQ ID NO 164
<211> LENGTH: 9
<212> TYPE: PRT
<213> ORGANISM: Homo sapiens
<220> FEATURE:
<223> OTHER INFORMATION: CDR-L1 of MnC1t3p1_G9

<400> SEQUENCE: 164

Thr Gly Pro Val Thr Ser Asp His Tyr
1 5

<210> SEQ ID NO 165
<211> LENGTH: 3
<212> TYPE: PRT
<213> ORGANISM: Homo sapiens
<220> FEATURE:
<223> OTHER INFORMATION: CDR-L2 of MnC1t3p1_G9

<400> SEQUENCE: 165

Asp Thr Asn
1

<210> SEQ ID NO 166
<211> LENGTH: 9
<212> TYPE: PRT
<213> ORGANISM: Homo sapiens
<220> FEATURE:
<223> OTHER INFORMATION: CDR-L3 of MnC1t3p1_G9

<400> SEQUENCE: 166

Leu Leu Ser Tyr Thr Gly Ala Arg Val
1 5

<210> SEQ ID NO 167
<211> LENGTH: 8
<212> TYPE: PRT
<213> ORGANISM: Homo sapiens
<220> FEATURE:
<223> OTHER INFORMATION: CDR-H1 of HbnC4t1p1_D5

<400> SEQUENCE: 167

Gly Phe Thr Phe Asp Asp Tyr Ala
1 5

<210> SEQ ID NO 168
<211> LENGTH: 8
<212> TYPE: PRT
<213> ORGANISM: Homo sapiens
<220> FEATURE:
<223> OTHER INFORMATION: CDR-H2 of HbnC4t1p1_D5

<400> SEQUENCE: 168

Ile Ser Trp Asn Ser Gly Ser Ile
1 5

<210> SEQ ID NO 169
<211> LENGTH: 18
<212> TYPE: PRT
<213> ORGANISM: Homo sapiens
<220> FEATURE:
<223> OTHER INFORMATION: CDR-H3 of HbnC4t1p1_D5

<400> SEQUENCE: 169

Ala Lys Asp Ile Asn Tyr Asp Ser Gly Gly Tyr His Lys Asn Tyr Phe
1 5 10 15

Asp Tyr

<210> SEQ ID NO 170
<211> LENGTH: 6
<212> TYPE: PRT
<213> ORGANISM: Homo sapiens
<220> FEATURE:
<223> OTHER INFORMATION: CDR-L1 of HbnC4t1p1_D5

<400> SEQUENCE: 170

Gln Ser Ile Ser Ser Tyr
1 5

<210> SEQ ID NO 171
<211> LENGTH: 3
<212> TYPE: PRT
<213> ORGANISM: Homo sapiens
<220> FEATURE:
<223> OTHER INFORMATION: CDR-L2 of HbnC4t1p1_D5

<400> SEQUENCE: 171

Ala Ala Ser
1

<210> SEQ ID NO 172
<211> LENGTH: 9
<212> TYPE: PRT
<213> ORGANISM: Homo sapiens
<220> FEATURE:
<223> OTHER INFORMATION: CDR-L3 of HbnC4t1p1_D5

<400> SEQUENCE: 172

Gln Gln Ser Tyr Ser Asn Pro Leu Thr
1 5

<210> SEQ ID NO 173
<211> LENGTH: 8
<212> TYPE: PRT
<213> ORGANISM: Homo sapiens
<220> FEATURE:
<223> OTHER INFORMATION: CDR-H1 of CnC2t1p1_B10

<400> SEQUENCE: 173

Gly Gly Thr Phe Ser Ser Tyr Ala
1 5

<210> SEQ ID NO 174
<211> LENGTH: 8
<212> TYPE: PRT
<213> ORGANISM: Homo sapiens
<220> FEATURE:
<223> OTHER INFORMATION: CDR-H2 of CnC2t1p1_B10

<400> SEQUENCE: 174

Ile Ile Pro Ile Phe Gly Thr Ala
1               5

<210> SEQ ID NO 175
<211> LENGTH: 15
<212> TYPE: PRT
<213> ORGANISM: Homo sapiens
<220> FEATURE:
<223> OTHER INFORMATION: CDR-H3 of CnC2t1p1_B10

<400> SEQUENCE: 175

Ala Arg Val Ser Gly Tyr Asp Ser Ser Gly Tyr Trp Gly Asp Tyr
1               5                   10                  15

<210> SEQ ID NO 176
<211> LENGTH: 6
<212> TYPE: PRT
<213> ORGANISM: Homo sapiens
<220> FEATURE:
<223> OTHER INFORMATION: CDR-L1 of CnC2t1p1_B10

<400> SEQUENCE: 176

Gln Ser Val Ser Ser Tyr
1               5

<210> SEQ ID NO 177
<211> LENGTH: 3
<212> TYPE: PRT
<213> ORGANISM: Homo sapiens
<220> FEATURE:
<223> OTHER INFORMATION: CDR-L2 of CnC2t1p1_B10

<400> SEQUENCE: 177

Asp Ala Ser
1

<210> SEQ ID NO 178
<211> LENGTH: 11
<212> TYPE: PRT
<213> ORGANISM: Homo sapiens
<220> FEATURE:
<223> OTHER INFORMATION: CDR-L3 of CnC2t1p1_B10

<400> SEQUENCE: 178

Gln Gln Arg Ser Asn Trp Pro Pro Ala Leu Thr
1               5                   10

<210> SEQ ID NO 179
<211> LENGTH: 8
<212> TYPE: PRT
<213> ORGANISM: Homo sapiens
<220> FEATURE:
<223> OTHER INFORMATION: CDR-H1 of CnC2t1p1_G6

<400> SEQUENCE: 179

Gly Tyr Ile Phe Thr Asn Tyr Tyr
1               5

<210> SEQ ID NO 180
<211> LENGTH: 8
<212> TYPE: PRT
<213> ORGANISM: Homo sapiens
<220> FEATURE:
<223> OTHER INFORMATION: CDR-H2 of CnC2t1p1_G6

<400> SEQUENCE: 180

Ile His Ser Leu Ser Gly Gly Thr
1               5

<210> SEQ ID NO 181
<211> LENGTH: 13
<212> TYPE: PRT
<213> ORGANISM: Homo sapiens
<220> FEATURE:
<223> OTHER INFORMATION: CDR-H3 of CnC2t1p1_G6

<400> SEQUENCE: 181

Ala Arg Ala Ser Val Ala Thr Ile Thr Asp Phe Asp Tyr
1               5                   10

<210> SEQ ID NO 182
<211> LENGTH: 9
<212> TYPE: PRT
<213> ORGANISM: Homo sapiens
<220> FEATURE:
<223> OTHER INFORMATION: CDR-L1 of CnC2t1p1_G6

<400> SEQUENCE: 182

Ser Gly Asp Ile Gly Ser Tyr Asn Leu
1               5

<210> SEQ ID NO 183
<211> LENGTH: 3
<212> TYPE: PRT
<213> ORGANISM: Homo sapiens
<220> FEATURE:
<223> OTHER INFORMATION: CDR-L2 of CnC2t1p1_G6

<400> SEQUENCE: 183

Glu Ala Ser
1

<210> SEQ ID NO 184
<211> LENGTH: 10
<212> TYPE: PRT
<213> ORGANISM: Homo sapiens
<220> FEATURE:
<223> OTHER INFORMATION: CDR-L3 of CnC2t1p1_G6

<400> SEQUENCE: 184

Cys Ser Tyr Ala Gly Val Arg Thr Val Val
1               5                   10

<210> SEQ ID NO 185
<211> LENGTH: 8
<212> TYPE: PRT
<213> ORGANISM: Homo sapiens
<220> FEATURE:
<223> OTHER INFORMATION: CDR-H1 of FnC1t1p2_A5

<400> SEQUENCE: 185

Gly Tyr Thr Phe Thr Ser Tyr Asp
1               5

<210> SEQ ID NO 186
<211> LENGTH: 8
<212> TYPE: PRT
<213> ORGANISM: Homo sapiens
<220> FEATURE:
<223> OTHER INFORMATION: CDR-H2 of FnC1t1p2_A5

<400> SEQUENCE: 186

Met Asn Pro Asn Ser Gly Asn Thr
1 5

<210> SEQ ID NO 187
<211> LENGTH: 32
<212> TYPE: PRT
<213> ORGANISM: Homo sapiens
<220> FEATURE:
<223> OTHER INFORMATION: CDR-H3 of FnC1t1p2_A5

<400> SEQUENCE: 187

Ala Arg Ala Thr Thr Asp Cys Ser Ser Thr Ser Cys Trp Ser Leu Asp
1 5 10 15

Phe Trp Ser Gly Tyr Tyr Thr Gly Gly Arg Glu Lys Ile Phe Asp Tyr
20 25 30

<210> SEQ ID NO 188
<211> LENGTH: 7
<212> TYPE: PRT
<213> ORGANISM: Homo sapiens
<220> FEATURE:
<223> OTHER INFORMATION: CDR-L1 of FnC1t1p2_A5

<400> SEQUENCE: 188

Gln Ser Val Ser Ser Ser Tyr
1 5

<210> SEQ ID NO 189
<211> LENGTH: 3
<212> TYPE: PRT
<213> ORGANISM: Homo sapiens
<220> FEATURE:
<223> OTHER INFORMATION: CDR-L2 of FnC1t1p2_A5

<400> SEQUENCE: 189

Gly Ala Ser
1

<210> SEQ ID NO 190
<211> LENGTH: 9
<212> TYPE: PRT
<213> ORGANISM: Homo sapiens
<220> FEATURE:
<223> OTHER INFORMATION: CDR-L3 of FnC1t1p2_A5

<400> SEQUENCE: 190

Gln Gln Tyr Gly Ser Ser Pro Gly Thr
1 5

<210> SEQ ID NO 191
<211> LENGTH: 10
<212> TYPE: PRT
<213> ORGANISM: Homo sapiens
<220> FEATURE:
<223> OTHER INFORMATION: CDR-H1 of MnC4t2p1_D10

<400> SEQUENCE: 191

Gly Ala Ser Ile Ser Ser Asn His Tyr Phe
1 5 10

<210> SEQ ID NO 192
<211> LENGTH: 7
<212> TYPE: PRT
<213> ORGANISM: Homo sapiens
<220> FEATURE:
<223> OTHER INFORMATION: CDR-H2 of MnC4t2p1_D10

<400> SEQUENCE: 192

Met His Tyr Ser Gly Ser Thr
1 5

<210> SEQ ID NO 193
<211> LENGTH: 20
<212> TYPE: PRT
<213> ORGANISM: Homo sapiens
<220> FEATURE:
<223> OTHER INFORMATION: CDR-H3 of MnC4t2p1_D10

<400> SEQUENCE: 193

Ala Arg Gly Val Asn Tyr Tyr Asp Arg Asn Gly Tyr Tyr Arg Asn Asp
1 5 10 15

Gly Phe Asp Ile
20

<210> SEQ ID NO 194
<211> LENGTH: 6
<212> TYPE: PRT
<213> ORGANISM: Homo sapiens
<220> FEATURE:
<223> OTHER INFORMATION: CDR-L1 of MnC4t2p1_D10

<400> SEQUENCE: 194

Gln Gly Ile Arg Asn Asp
1 5

<210> SEQ ID NO 195
<211> LENGTH: 3
<212> TYPE: PRT
<213> ORGANISM: Homo sapiens
<220> FEATURE:
<223> OTHER INFORMATION: CDR-L2 of MnC4t2p1_D10

<400> SEQUENCE: 195

Ala Ala Ser
1

<210> SEQ ID NO 196
<211> LENGTH: 9
<212> TYPE: PRT
<213> ORGANISM: Homo sapiens
<220> FEATURE:
<223> OTHER INFORMATION: CDR-L3 of MnC4t2p1_D10

<400> SEQUENCE: 196

Leu Gln His Asn Thr Tyr Pro Phe Thr
1 5

<210> SEQ ID NO 197
<211> LENGTH: 8
<212> TYPE: PRT
<213> ORGANISM: Homo sapiens
<220> FEATURE:
<223> OTHER INFORMATION: CDR-H1 of MnC4t2p2_A4

<400> SEQUENCE: 197

```
Gly Tyr Ile Phe Ile Asn Tyr Ala
1               5


<210> SEQ ID NO 198
<211> LENGTH: 8
<212> TYPE: PRT
<213> ORGANISM: Homo sapiens
<220> FEATURE:
<223> OTHER INFORMATION: CDR-H2 of MnC4t2p2_A4

<400> SEQUENCE: 198

Ile Asn Thr Asn Thr Gly Asn Pro
1               5


<210> SEQ ID NO 199
<211> LENGTH: 11
<212> TYPE: PRT
<213> ORGANISM: Homo sapiens
<220> FEATURE:
<223> OTHER INFORMATION: CDR-H3 of MnC4t2p2_A4

<400> SEQUENCE: 199

Ala Lys Ile Gly Ser Arg Asn Ser Leu Gly Val
1               5                   10


<210> SEQ ID NO 200
<211> LENGTH: 7
<212> TYPE: PRT
<213> ORGANISM: Homo sapiens
<220> FEATURE:
<223> OTHER INFORMATION: CDR-L1 of MnC4t2p2_A4

<400> SEQUENCE: 200

His Ser Val Asp Arg Ser Tyr
1               5


<210> SEQ ID NO 201
<211> LENGTH: 3
<212> TYPE: PRT
<213> ORGANISM: Homo sapiens
<220> FEATURE:
<223> OTHER INFORMATION: CDR-L2 of MnC4t2p2_A4

<400> SEQUENCE: 201

Gly Ala Ser
1


<210> SEQ ID NO 202
<211> LENGTH: 9
<212> TYPE: PRT
<213> ORGANISM: Homo sapiens
<220> FEATURE:
<223> OTHER INFORMATION: CDR-L3 of MnC4t2p2_A4

<400> SEQUENCE: 202

Gln His Phe Gly Thr Ser Ser Val Thr
1               5


<210> SEQ ID NO 203
<211> LENGTH: 10
<212> TYPE: PRT
<213> ORGANISM: Homo sapiens
<220> FEATURE:
<223> OTHER INFORMATION: CDR-H1 of MnC4t1p1_A10

<400> SEQUENCE: 203

Gly Ala Ser Ile Ser Ser Asn His Tyr Phe
```

1 5 10

<210> SEQ ID NO 204
<211> LENGTH: 7
<212> TYPE: PRT
<213> ORGANISM: Homo sapiens
<220> FEATURE:
<223> OTHER INFORMATION: CDR-H2 of MnC4t1p1_A10

<400> SEQUENCE: 204

Met His Tyr Ser Gly Ser Thr
1 5

<210> SEQ ID NO 205
<211> LENGTH: 20
<212> TYPE: PRT
<213> ORGANISM: Homo sapiens
<220> FEATURE:
<223> OTHER INFORMATION: CDR-H3 of MnC4t1p1_A10

<400> SEQUENCE: 205

Ala Arg Gly Val Asn Tyr Tyr Asp Arg Asn Gly Tyr Tyr Arg Asn Asp
1 5 10 15

Gly Phe Asp Ile
20

<210> SEQ ID NO 206
<211> LENGTH: 6
<212> TYPE: PRT
<213> ORGANISM: Homo sapiens
<220> FEATURE:
<223> OTHER INFORMATION: CDR-L1 of MnC4t1p1_A10

<400> SEQUENCE: 206

Gln Gly Ile Arg Asn Asp
1 5

<210> SEQ ID NO 207
<211> LENGTH: 3
<212> TYPE: PRT
<213> ORGANISM: Homo sapiens
<220> FEATURE:
<223> OTHER INFORMATION: CDR-L2 of MnC4t1p1_A10

<400> SEQUENCE: 207

Ala Ala Ser
1

<210> SEQ ID NO 208
<211> LENGTH: 9
<212> TYPE: PRT
<213> ORGANISM: Homo sapiens
<220> FEATURE:
<223> OTHER INFORMATION: CDR-L3 of MnC4t1p1_A10

<400> SEQUENCE: 208

Leu Gln His Asn Thr Tyr Pro Phe Thr
1 5

<210> SEQ ID NO 209
<211> LENGTH: 8
<212> TYPE: PRT
<213> ORGANISM: Homo sapiens
<220> FEATURE:
<223> OTHER INFORMATION: CDR-H1 of MnC4t2p1_E6

<400> SEQUENCE: 209

Gly Phe Thr Phe Asp Asp Tyr Ala
1 5

<210> SEQ ID NO 210
<211> LENGTH: 8
<212> TYPE: PRT
<213> ORGANISM: Homo sapiens
<220> FEATURE:
<223> OTHER INFORMATION: CDR-H2 of MnC4t2p1_E6

<400> SEQUENCE: 210

Ile Ser Trp Asn Gly Gly Ile Leu
1 5

<210> SEQ ID NO 211
<211> LENGTH: 17
<212> TYPE: PRT
<213> ORGANISM: Homo sapiens
<220> FEATURE:
<223> OTHER INFORMATION: CDR-H3 of MnC4t2p1_E6

<400> SEQUENCE: 211

Ala Lys Asp Leu Arg Arg Gln Asp Tyr Tyr Ala Asp Trp Tyr Phe Asp
1 5 10 15

Leu

<210> SEQ ID NO 212
<211> LENGTH: 6
<212> TYPE: PRT
<213> ORGANISM: Homo sapiens
<220> FEATURE:
<223> OTHER INFORMATION: CDR-L1 of MnC4t2p1_E6

<400> SEQUENCE: 212

Gln Gly Ile Ser Ser Trp
1 5

<210> SEQ ID NO 213
<211> LENGTH: 3
<212> TYPE: PRT
<213> ORGANISM: Homo sapiens
<220> FEATURE:
<223> OTHER INFORMATION: CDR-L2 of MnC4t2p1_E6

<400> SEQUENCE: 213

Ala Ala Ser
1

<210> SEQ ID NO 214
<211> LENGTH: 9
<212> TYPE: PRT
<213> ORGANISM: Homo sapiens
<220> FEATURE:
<223> OTHER INFORMATION: CDR-L3 of MnC4t2p1_E6

<400> SEQUENCE: 214

Gln Gln Gly Asn Ser Phe Pro Phe Thr
1 5

<210> SEQ ID NO 215
<211> LENGTH: 8
<212> TYPE: PRT
<213> ORGANISM: Homo sapiens
<220> FEATURE:
<223> OTHER INFORMATION: CDR-H1 of MnC4t1p1_A11

<400> SEQUENCE: 215

Gly Phe Thr Phe Ser Ser Tyr Ser
1               5

<210> SEQ ID NO 216
<211> LENGTH: 8
<212> TYPE: PRT
<213> ORGANISM: Homo sapiens
<220> FEATURE:
<223> OTHER INFORMATION: CDR-H2 of MnC4t1p1_A11

<400> SEQUENCE: 216

Ile Ser Ser Ser Ser Asn Thr Arg
1               5

<210> SEQ ID NO 217
<211> LENGTH: 15
<212> TYPE: PRT
<213> ORGANISM: Homo sapiens
<220> FEATURE:
<223> OTHER INFORMATION: CDR-H3 of MnC4t1p1_A11

<400> SEQUENCE: 217

Ala Ser Ser Lys Gly Phe Cys Ser Gly Gly Ser Cys Ser Asp Tyr
1               5                   10                  15

<210> SEQ ID NO 218
<211> LENGTH: 7
<212> TYPE: PRT
<213> ORGANISM: Homo sapiens
<220> FEATURE:
<223> OTHER INFORMATION: CDR-L1 of MnC4t1p1_A11

<400> SEQUENCE: 218

Gln Ser Val Ser Ser Ser Tyr
1               5

<210> SEQ ID NO 219
<211> LENGTH: 3
<212> TYPE: PRT
<213> ORGANISM: Homo sapiens
<220> FEATURE:
<223> OTHER INFORMATION: CDR-L2 of MnC4t1p1_A11

<400> SEQUENCE: 219

Gly Val Ser
1

<210> SEQ ID NO 220
<211> LENGTH: 9
<212> TYPE: PRT
<213> ORGANISM: Homo sapiens
<220> FEATURE:
<223> OTHER INFORMATION: CDR-L3 of MnC4t1p1_A11

<400> SEQUENCE: 220

His Gln Tyr Gly Ser Ser Pro Trp Thr
1               5

<210> SEQ ID NO 221
<211> LENGTH: 10
<212> TYPE: PRT
<213> ORGANISM: Homo sapiens
<220> FEATURE:
<223> OTHER INFORMATION: CDR-H1 of MnC4t2p1_F5

<400> SEQUENCE: 221

```
Gly Ala Ser Ile Ser Ser Asn His Tyr Phe
1               5                   10


<210> SEQ ID NO 222
<211> LENGTH: 7
<212> TYPE: PRT
<213> ORGANISM: Homo sapiens
<220> FEATURE:
<223> OTHER INFORMATION: CDR-H2 of MnC4t2p1_F5

<400> SEQUENCE: 222

Met His Tyr Ser Gly Ser Thr
1               5


<210> SEQ ID NO 223
<211> LENGTH: 20
<212> TYPE: PRT
<213> ORGANISM: Homo sapiens
<220> FEATURE:
<223> OTHER INFORMATION: CDR-H3 of MnC4t2p1_F5

<400> SEQUENCE: 223

Ala Arg Gly Val Asn Tyr Tyr Asp Arg Asn Gly Tyr Tyr Arg Asn Asp
1               5                   10                  15

Gly Phe Asp Ile
            20


<210> SEQ ID NO 224
<211> LENGTH: 6
<212> TYPE: PRT
<213> ORGANISM: Homo sapiens
<220> FEATURE:
<223> OTHER INFORMATION: CDR-L1 of MnC4t2p1_F5

<400> SEQUENCE: 224

Gln Gly Ile Arg Asn Asp
1               5


<210> SEQ ID NO 225
<211> LENGTH: 3
<212> TYPE: PRT
<213> ORGANISM: Homo sapiens
<220> FEATURE:
<223> OTHER INFORMATION: CDR-L2 of MnC4t2p1_F5

<400> SEQUENCE: 225

Ala Ala Ser
1


<210> SEQ ID NO 226
<211> LENGTH: 9
<212> TYPE: PRT
<213> ORGANISM: Homo sapiens
<220> FEATURE:
<223> OTHER INFORMATION: CDR-L3 of MnC4t2p1_F5

<400> SEQUENCE: 226

Leu Gln His Asn Thr Tyr Pro Phe Thr
1               5


<210> SEQ ID NO 227
<211> LENGTH: 8
<212> TYPE: PRT
<213> ORGANISM: Homo sapiens
<220> FEATURE:
<223> OTHER INFORMATION: derivative of CDR-H2 of CnC2t1p1_B4
```

<400> SEQUENCE: 227

Ile Ser Ala Tyr Ser Gly Asn Thr
1               5

<210> SEQ ID NO 228
<211> LENGTH: 10
<212> TYPE: PRT
<213> ORGANISM: Homo sapiens
<220> FEATURE:
<223> OTHER INFORMATION: derivative of CDR-L3 of CnC2t1p1_B4

<400> SEQUENCE: 228

Gln Ser Tyr Ala Gly Ser Ser Thr Trp Val
1               5                   10

<210> SEQ ID NO 229
<211> LENGTH: 449
<212> TYPE: PRT
<213> ORGANISM: Artificial Sequence
<220> FEATURE:
<223> OTHER INFORMATION: Complete heavy chain of antibody DZIF-10c
      (HbnC3t1p1_F4(-K))

<400> SEQUENCE: 229

Gln Val Gln Leu Val Glu Ser Gly Gly Gly Val Val Gln Pro Gly Arg
1               5                   10                  15

Ser Leu Arg Leu Ser Cys Ala Ala Thr Gly Phe Thr Phe Arg Arg Tyr
            20                  25                  30

Gly Met His Trp Val Arg Gln Ala Pro Gly Lys Gly Leu Glu Trp Val
        35                  40                  45

Ala Gly Ile Leu Phe Asp Gly Ser Asn Lys Tyr Tyr Val Asp Ser Val
    50                  55                  60

Lys Gly Arg Phe Thr Ile Ser Arg Asp Ser Ser Arg Asn Thr Leu Tyr
65                  70                  75                  80

Leu Gln Leu Asn Ser Leu Arg Arg Glu Asp Thr Ala Val Tyr Tyr Cys
                85                  90                  95

Ala Lys Gly Gly Asp Tyr Glu Trp Glu Leu Leu Glu Ser Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu

```
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 230
<211> LENGTH: 214
<212> TYPE: PRT
<213> ORGANISM: Artificial Sequence
<220> FEATURE:
<223> OTHER INFORMATION: Complete light chain of antibody DZIF-10c
      (HbnC3t1p1_F4(-K))

<400> SEQUENCE: 230

Asp Ile Gln Met Thr Gln Ser Pro Ser Thr Val Ser Ala Ser Val Gly
1               5                   10                  15

Asp Arg Val Thr Ile Thr Cys Arg Ala Ser Gln Ser Ile Asp Asn Trp
            20                  25                  30

Leu Ala Trp Tyr Gln Glu Lys Pro Gly Lys Ala Pro Lys Val Leu Ile
        35                  40                  45

Tyr Lys Ala Ser Ser Leu Glu Ser Gly Val Pro Ser Arg Phe Ser Gly
    50                  55                  60

Arg Gly Ser Gly Thr Glu Phe Thr Leu Thr Ile Ser Ser Leu Gln Pro
65                  70                  75                  80

Gly Asp Phe Ala Thr Tyr Tyr Cys Gln His Tyr His Ser Phe Pro Leu
                85                  90                  95

Thr Phe Gly Gly Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
```

-continued

```
              165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

NEUTRALIZING ANTIBODIES AGAINST SARS-RELATED CORONAVIRUS

CROSS-REFERENCE TO RELATED APPLICATIONS

This application claims priority to and benefit of European Application No. 20177354.6, filed May 29, 2020, European Application No. 20182325.9, filed Jun. 25, 2020, and European Application No. 20213562.0, filed Dec. 11, 2020, the entire respective disclosures of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on May 26, 2021, is named 105218_03_5009_US_Sequence_Listing.txt and is 119,187 bytes in size.

TECHNICAL FIELD

The present invention relates to antibodies or antigen-binding fragments thereof against SARS-related coronavirus, a pharmaceutical composition comprising such antibodies or antigen-binding fragments thereof, and a kit comprising such antibodies or antigen-binding fragments thereof. The present invention also relates to the antibodies or antigen-binding fragments thereof, the pharmaceutical composition, and the kit for use as a medicament including in the treatment or prevention of a disease caused by SARS-related coronavirus.

BACKGROUND OF THE INVENTION

The emergence of a novel and highly pathogenic coronavirus (severe acute respiratory syndrome coronavirus 2, SARS-CoV-2) and its rapid international spread poses a serious global public health emergency. Similar to individuals infected with other highly pathogenic coronavirus strains such as severe acute respiratory syndrome coronavirus (SARS-CoV) which emerged in 2003 or Middle East respiratory syndrome coronavirus (MERS-CoV) which emerged in 2012, patients infected by SARS-CoV-2 can manifest a range of symptoms including dry cough, fever, headache, dyspnea and pneumonia with an estimated mortality rate in the range of 3-5%.

Since the initial outbreak in December of 2019, SARS-CoV-2 has spread to 217 countries, areas and territories worldwide overall. As of May 27, 2020, U.S. Pat. No. 5,488,825 infections with the virus have been confirmed globally with 349,095 confirmed deaths of infected patients (https://www.who.int/emergencies/diseases/novel-coronavirus-2019).

In response to the spread of the virus which turned into a global pandemic in 2020 and has been declared as such by the WHO, various cities and countries across the world are under lockdown to various extents to minimize continued spread. The SARS-CoV-2 pandemic of 2020 has led to unprecedented implications for public health, social life, and world economy.

Since approved drugs and vaccines are not available to counter this outbreak, new options for COVID-19 treatment and prevention are highly demanded. Therefore, decoding SARS-CoV-2 immunity for developing vaccines and potent antiviral drugs is an urgent health need.

Monoclonal antibodies (mAbs) have been demonstrated to effectively target and neutralize viruses such as Ebola virus, respiratory syncytial virus (RSV), or human immunodeficiency virus 1 (HIV-1). The most prominent target for an antibody-mediated response on the surface of SARS-CoV-2 virions is the homotrimeric spike (S) protein. The S protein promotes cell entry through the interaction of a receptor-binding domain (RBD) with angiotensin-converting enzyme 2 (ACE2). Monoclonal human antibodies that target the S protein are therefore of high value to prevent and/or treat COVID-19.

While promising data have recently been published (mostly in the form of pre-prints which have not been subject to formal peer review) for a small number of antibodies showing neutralizing activity against SARS-CoV-2 in different experimental setups, these data suffer either from a lack of public availability of amino acid sequences of the antibodies tested, lack of experimental evidence for neutralizing activity against the live virus, autoreactivity or self-reactivity of said antibodies, or comparatively low neutralization potency against the live SARS-CoV-2 virus.

Due to the shortcomings mentioned above, there remains a demand for human antibodies directed against SARS-related coronavirus which do not show autoreactivity and have superior neutralization potency against live virus in comparison to publicly available antibodies published in sufficient detail.

Thus, it is an object of the present invention to provide novel monoclonal antibodies against SARS-related coronavirus which do not demonstrate autoreactivity and have excellent neutralization potency against live virus. It is a further object of the present invention to provide monoclonal antibodies against SARS-related coronavirus which can be used in treatment or prevention of a disease caused by SARS-related coronavirus in human or animal subjects as well as in prevention of infection of a human or animal subject with SARS-related coronavirus.

SUMMARY OF THE INVENTION

These objects have been solved by the aspects of the present invention as specified hereinafter.

According to a first aspect of the present invention, an isolated antibody or antigen-binding fragment thereof directed against SARS-related coronavirus is provided, wherein the antibody or antigen-binding fragment thereof comprises the heavy chain CDR1, CDR2, and CDR3 and the light chain CDR1, CDR2, and CDR3 amino acid sequence of one antibody from the group comprising HbnC3t1p1_C6 (with the variable region heavy chain amino acid sequence of SEQ ID No. 1 and the variable region light chain amino acid sequence of SEQ ID No. 2), HbnC3t1p1_G4 (with the variable region heavy chain amino acid sequence of SEQ ID No. 3 and the variable region light chain amino acid sequence of SEQ ID No. 4), HbnC3t1p2_B10 with the variable region heavy chain amino acid sequence of SEQ ID No. 5 and the variable region light chain amino acid sequence of SEQ ID No. 6), MnC2t2p1_C11 (with the variable region heavy chain amino acid sequence of SEQ ID No. 7 and the variable region light chain amino acid sequence of SEQ ID No. 8), FnC1t2p1_D4 (with the variable region heavy chain amino acid sequence of SEQ ID No. 9 and the variable region light chain amino acid sequence of SEQ ID No. 10), FnC1t2p1_G5 (with the variable region heavy chain amino acid sequence of SEQ ID No. 11 and the variable region light chain amino acid sequence of SEQ ID No. 12), HbnC3t1p2_C6 (with the variable region heavy chain amino acid sequence of SEQ ID No. 13 and the variable region light chain amino acid sequence of SEQ ID No. 14), MnC4t2p1_B3 (with the variable region heavy chain amino acid sequence of SEQ ID No. 15 and the variable region light chain amino acid sequence of SEQ ID No. 16), MnC2t1p1_A3 (with the variable region heavy chain amino acid sequence of SEQ ID No. 17 and the variable region light chain amino acid sequence of SEQ ID No. 18), CnC2t1p1_B4 (with the variable region heavy chain amino acid sequence of SEQ ID No. 19 and the variable region light chain amino acid sequence of SEQ ID No. 20), HbnC3t1p1_F4 (with the variable region heavy chain amino acid sequence of SEQ ID No. 21 and the variable region light chain amino acid sequence of SEQ ID No. 22), HbnC2t1p2_D9 (with the variable region heavy chain amino acid sequence of SEQ ID No. 23 and the variable region light chain amino acid sequence of SEQ ID No. 24), MnC5t2p1_G1 (with the variable region heavy chain amino acid sequence of SEQ ID No. 25 and the variable region light chain amino acid sequence of SEQ ID No. 26), CnC2t1p1_E12 (with the variable region heavy chain amino acid sequence of SEQ ID No. 27 and the variable region light chain amino acid sequence of SEQ ID No. 28), CnC2t1p1_D6 (with the variable region heavy chain amino acid sequence of SEQ ID No. 29 and the variable region light chain amino acid sequence of SEQ ID No. 30), MnC2t1p1_C5 (with the variable region heavy chain amino acid sequence of SEQ ID No. 31 and the variable region light chain amino acid sequence of SEQ ID No. 32), CnC2t1p1_E8 (with the variable region heavy chain amino acid sequence of SEQ ID No. 33 and the variable region light chain amino acid sequence of SEQ ID No. 34), MnC1t3p1_G9 (with the variable region heavy chain amino acid sequence of SEQ ID No. 35 and the variable region light chain amino acid sequence of SEQ ID No. 36), HbnC4t1p1_D5 (with the variable region heavy chain amino acid sequence of SEQ ID No. 37 and the variable region light chain amino acid sequence of SEQ ID No. 38), CnC2t1p1_B10 (with the variable region heavy chain amino acid sequence of SEQ ID No. 39 and the variable region light chain amino acid sequence of SEQ ID No. 40), CnC2t1p1_G6 (with the variable region heavy chain amino acid sequence of SEQ ID No. 41 and the variable region light chain amino acid sequence of SEQ ID No. 42), FnC1t1p2_A5 (with the variable region heavy chain amino acid sequence of SEQ ID No. 43 and the variable region light chain amino acid sequence of SEQ ID No. 44), MnC4t2p1_D10 (with the variable region heavy chain amino acid sequence of SEQ ID No. 45 and the variable region light chain amino acid sequence of SEQ ID No. 46), MnC4t2p2_A4 (with the variable region heavy chain amino acid sequence of SEQ ID No. 47 and the variable region light chain amino acid sequence of SEQ ID No. 48), MnC4t1p1_A10 (with the variable region heavy chain amino acid sequence of SEQ ID No. 49 and the variable region light chain amino acid sequence of SEQ ID No. 50), MnC4t2p1_E6 (with the variable region heavy chain amino acid sequence of SEQ ID No. 51 and the variable region light chain amino acid sequence of SEQ ID No. 52), MnC4t1p1_A11 (with the variable region heavy chain amino acid sequence of SEQ ID No. 53 and the variable region light chain amino acid sequence of SEQ ID No. 54), and MnC4t2p1_F5 (with the variable region heavy chain amino acid sequence of SEQ ID No. 55 and the variable region light chain amino acid sequence of SEQ ID No. 56). In an embodiment, the antibody or antigen-binding fragment thereof comprises the heavy chain CDR1, CDR2, and CDR3 and the light chain CDR1, CDR2, and CDR3 amino acid sequence of one of the antibodies selected from the group comprising HbnC3t1p1_C6, HbnC3t1p1_G4, HbnC3t1p2_B10, MnC2t2p1_C11, FnC1t2p1_D4, FnC1t2p1_G5, HbnC3t1p2_06, MnC4t2p1_B3, MnC2t1p1_A3, CnC2t1p1_B4, HbnC3t1p1_F4, and HbnC2t1p2_D9. In an embodiment, the antibody or antigen-binding fragment thereof comprises the heavy chain CDR1, CDR2, and CDR3 and the light chain CDR1, CDR2, and CDR3 amino acid sequence of one of the antibodies selected from the group comprising HbnC3t1p1_C6, HbnC3t1p1_G4, HbnC3t1p2_B10, MnC2t2p1_C11, and FnC1t2p1_D4.

In one embodiment of the first aspect of the present invention, the antibody or antigen-binding fragment thereof comprises a combination of a variable region heavy chain sequence and of a variable region light chain sequence of one antibody selected from the group comprising HbnC3t1p1_C6 (with the variable region heavy chain amino acid sequence of SEQ ID No. 1 and the variable region light chain amino acid sequence of SEQ ID No. 2), HbnC3t1p1_G4 (with the variable region heavy chain amino acid sequence of SEQ ID No. 3 and the variable region light chain amino acid sequence of SEQ ID No. 4), HbnC3t1p2_B10 with the variable region heavy chain amino acid sequence of SEQ ID No. 5 and the variable region light chain amino acid sequence of SEQ ID No. 6), MnC2t2p1_C11 (with the variable region heavy chain amino acid sequence of SEQ ID No. 7 and the variable region light chain amino acid sequence of SEQ ID No. 8), FnC1t2p1_D4 (with the variable region heavy chain amino acid sequence of SEQ ID No. 9 and the variable region light chain amino acid sequence of SEQ ID No. 10), FnC1t2p1_G5 (with the variable region heavy chain amino acid sequence of SEQ ID No. 11 and the variable region light chain amino acid sequence of SEQ ID No. 12), HbnC3t1p2_C6 (with the variable region heavy chain amino acid sequence of SEQ ID No. 13 and the variable region light chain amino acid sequence of SEQ ID No. 14), MnC4t2p1_B3 (with the variable region heavy chain amino acid sequence of SEQ ID No. 15 and the variable region light chain amino acid sequence of SEQ ID No. 16), MnC2t1p1_A3 (with the variable region heavy chain amino acid sequence of SEQ ID No. 17 and the variable region light chain amino acid sequence of SEQ ID No. 18), CnC2t1p1_B4 (with the variable region heavy chain amino acid sequence of SEQ ID No. 19 and the variable region light chain amino acid sequence of SEQ ID No. 20), HbnC3t1p1_F4 (with the variable region heavy chain amino acid sequence of SEQ ID No. 21 and the variable region light chain amino acid sequence of SEQ ID No. 22), HbnC2t1p2_D9 (with the variable region heavy chain amino acid sequence of SEQ ID No. 23 and the variable region light chain amino acid sequence of SEQ ID No. 24), MnC5t2p1_G1 (with the variable region heavy chain amino acid sequence of SEQ ID No. 25 and the variable region light chain amino acid sequence of SEQ ID No. 26), CnC2t1p1_E12 (with the variable region heavy chain amino acid sequence of SEQ ID No. 27 and the variable region light chain amino acid sequence of SEQ ID No. 28), CnC2t1p1_D6 (with the variable region heavy chain amino acid sequence of SEQ ID No. 29 and the variable region light chain amino acid sequence of SEQ ID No. 30), MnC2t1p1_C5 (with the variable region heavy chain amino acid sequence of SEQ ID No. 31 and the variable region light chain amino acid sequence of SEQ ID No. 32), CnC2t1p1_E8 (with the variable region heavy chain amino acid sequence of SEQ ID No. 33 and the variable region light chain amino acid sequence of SEQ ID No. 34), MnC1t3p1_G9 (with the variable region heavy chain amino acid sequence of SEQ ID No. 35 and the variable region light chain amino acid sequence of SEQ ID No. 36), HbnC4t1p1_D5 (with the variable region heavy chain amino acid sequence of SEQ ID No. 37 and the variable region light chain amino acid sequence of SEQ ID No. 38), CnC2t1p1_B10 (with the variable region heavy chain amino acid sequence of SEQ ID No. 39 and the variable region light chain amino acid sequence of SEQ ID No. 40), CnC2t1p1_G6 (with the variable region heavy chain amino acid sequence of SEQ ID No. 41 and the variable region light chain amino acid sequence of SEQ ID No. 42), FnC1t1p2_A5 (with the variable region heavy chain amino acid sequence of SEQ ID No. 43 and the variable region light chain amino acid sequence of SEQ ID No. 44), MnC4t2p1_D10 (with the variable region heavy chain amino acid sequence of SEQ ID No. 45 and the variable region light chain amino acid sequence of SEQ ID No. 46), MnC4t2p2_A4 (with the variable region heavy chain amino acid sequence of SEQ ID No. 47 and the variable region light chain amino acid sequence of SEQ ID No. 48), MnC4t1p1_A10 (with the variable region heavy chain amino acid sequence of SEQ ID No. 49 and the variable region light chain amino acid sequence of SEQ ID No. 50), MnC4t2p1_E6 (with the variable region heavy chain amino acid sequence of SEQ ID No. 51 and the variable region light chain amino acid sequence of SEQ ID No. 52), MnC4t1p1_A11 (with the variable region heavy chain amino acid sequence of SEQ ID No. 53 and the variable region light chain amino acid sequence of SEQ ID No. 54), and MnC4t2p1_F5 (with the variable region heavy chain amino acid sequence of SEQ ID No. 55 and the variable region light chain amino acid sequence of SEQ ID No. 56). In an embodiment, the antibody or antigen-binding fragment thereof comprises a combination of a variable region heavy chain sequence and of a variable region light chain sequence of one antibody selected from the group comprising HbnC3t1p1_C6, HbnC3t1p1_G4, HbnC3t1p2_B10, MnC2t2p1_C11, FnC1t2p1_D4, FnC1t2p1_G5, HbnC3t1p2_C6, MnC4t2p1_B3, MnC2t1p1_A3, CnC2t1p1_B4, HbnC3t1p1_F4, and HbnC2t1p2_D9. In an embodiment, the antibody or antigen-binding fragment thereof comprises a combination of a variable region heavy chain sequence and of a variable region light chain sequence of one antibody selected from the group comprising HbnC3t1p1_C6, HbnC3t1p1_G4, HbnC3t1p2_B10, MnC2t2p1_C11, and FnC1t2p1_D4.

In one embodiment of the first aspect of the present invention, the isolated antibody or antigen-binding fragment thereof comprises a heavy chain CDR1, CDR2, and CDR3 and a light chain CDR1, CDR2, and CDR3, (a) wherein the heavy chain CDR1, CDR2, and CDR3 comprises SEQ ID NO: 59, SEQ ID NO: 60, and SEQ ID NO: 61, respectively; and wherein the light chain CDR1, CDR2, and CDR3 comprises SEQ ID NO: 62, SEQ ID NO: 63, and SEQ ID NO: 64, respectively;

(b) wherein the heavy chain CDR1, CDR2, and CDR3 comprises SEQ ID NO: 65, SEQ ID NO: 66, and SEQ ID NO: 67, respectively; and wherein the light chain CDR1, CDR2, and CDR3 comprises SEQ ID NO: 68, SEQ ID NO: 69, and SEQ ID NO: 70, respectively;

(c) wherein the heavy chain CDR1, CDR2, and CDR3 comprises SEQ ID NO: 71, SEQ ID NO: 72, and SEQ ID NO: 73, respectively; and wherein the light chain CDR1, CDR2, and CDR3 comprises SEQ ID NO: 74, SEQ ID NO: 75, and SEQ ID NO: 76, respectively;

(d) wherein the heavy chain CDR1, CDR2, and CDR3 comprises SEQ ID NO: 77, SEQ ID NO: 78, and SEQ ID NO: 79, respectively; and wherein the light chain CDR1, CDR2, and CDR3 comprises SEQ ID NO: 80, SEQ ID NO: 81, and SEQ ID NO: 82, respectively;

(e) wherein the heavy chain CDR1, CDR2, and CDR3 comprises SEQ ID NO: 83, SEQ ID NO: 84, and SEQ ID NO: 85, respectively; and wherein the light chain CDR1, CDR2, and CDR3 comprises SEQ ID NO: 86, SEQ ID NO: 87, and SEQ ID NO: 88, respectively;

(f) wherein the heavy chain CDR1, CDR2, and CDR3 comprises SEQ ID NO: 89, SEQ ID NO: 90, and SEQ ID NO: 91, respectively; and wherein the light chain CDR1, CDR2, and CDR3 comprises SEQ ID NO: 92, SEQ ID NO: 93, and SEQ ID NO: 94, respectively;

(g) wherein the heavy chain CDR1, CDR2, and CDR3 comprises SEQ ID NO: 95, SEQ ID NO: 96, and SEQ ID NO: 97, respectively; and wherein the light chain CDR1, CDR2, and CDR3 comprises SEQ ID NO: 98, SEQ ID NO: 99, and SEQ ID NO: 100, respectively;

(h) wherein the heavy chain CDR1, CDR2, and CDR3 comprises SEQ ID NO: 101, SEQ ID NO: 102, and SEQ ID NO: 103, respectively; and wherein the light chain CDR1, CDR2, and CDR3 comprises SEQ ID NO: 104, SEQ ID NO: 105, and SEQ ID NO: 106, respectively;

(i) wherein the heavy chain CDR1, CDR2, and CDR3 comprises SEQ ID NO: 107, SEQ ID NO: 108, and SEQ ID NO: 109, respectively; and wherein the light chain CDR1, CDR2, and CDR3 comprises SEQ ID NO: 110, SEQ ID NO: 111, and SEQ ID NO: 112, respectively;

(j) wherein the heavy chain CDR1, CDR2, and CDR3 comprises SEQ ID NO: 113, SEQ ID NO: 114, and SEQ ID NO: 115, respectively; and wherein the light chain CDR1, CDR2, and CDR3 comprises SEQ ID NO: 116, SEQ ID NO: 117, and SEQ ID NO: 118, respectively;

(k) wherein the heavy chain CDR1, CDR2, and CDR3 comprises SEQ ID NO: 119, SEQ ID NO: 120, and SEQ ID NO: 121, respectively; and wherein the light chain CDR1, CDR2, and CDR3 comprises SEQ ID NO: 122, SEQ ID NO: 123, and SEQ ID NO: 124, respectively;

(l) wherein the heavy chain CDR1, CDR2, and CDR3 comprises SEQ ID NO: 125, SEQ ID NO: 126, and SEQ ID NO: 127, respectively; and wherein the light chain CDR1, CDR2, and CDR3 comprises SEQ ID NO: 128, SEQ ID NO: 129, and SEQ ID NO: 130, respectively;

(m) wherein the heavy chain CDR1, CDR2, and CDR3 comprises SEQ ID NO: 131, SEQ ID NO: 132, and SEQ ID NO: 133, respectively; and wherein the light chain CDR1, CDR2, and CDR3 comprises SEQ ID NO: 134, SEQ ID NO: 135, and SEQ ID NO: 136, respectively;

(n) wherein the heavy chain CDR1, CDR2, and CDR3 comprises SEQ ID NO: 137, SEQ ID NO: 138, and SEQ ID NO: 139, respectively; and wherein the light chain CDR1, CDR2, and CDR3 comprises SEQ ID NO: 140, SEQ ID NO: 141, and SEQ ID NO: 142, respectively;

(o) wherein the heavy chain CDR1, CDR2, and CDR3 comprises SEQ ID NO: 143, SEQ ID NO: 144, and SEQ ID NO: 145, respectively; and wherein the light chain CDR1, CDR2, and CDR3 comprises SEQ ID NO: 146, SEQ ID NO: 147, and SEQ ID NO: 148, respectively;

(p) wherein the heavy chain CDR1, CDR2, and CDR3 comprises SEQ ID NO: 149, SEQ ID NO: 150, and SEQ ID NO: 151, respectively; and wherein the light chain CDR1, CDR2, and CDR3 comprises SEQ ID NO: 152, SEQ ID NO: 153, and SEQ ID NO: 154, respectively;

(q) wherein the heavy chain CDR1, CDR2, and CDR3 comprises SEQ ID NO: 155, SEQ ID NO: 156, and SEQ ID NO: 157, respectively; and wherein the light chain CDR1, CDR2, and CDR3 comprises SEQ ID NO: 158, SEQ ID NO: 159, and SEQ ID NO: 160, respectively;

(r) wherein the heavy chain CDR1, CDR2, and CDR3 comprises SEQ ID NO: 161, SEQ ID NO: 162, and SEQ ID NO: 163, respectively; and wherein the light chain CDR1, CDR2, and CDR3 comprises SEQ ID NO: 164, SEQ ID NO: 165, and SEQ ID NO: 166, respectively;

(s) wherein the heavy chain CDR1, CDR2, and CDR3 comprises SEQ ID NO: 167, SEQ ID NO: 168, and SEQ ID NO: 169, respectively; and wherein the light chain CDR1, CDR2, and CDR3 comprises SEQ ID NO: 170, SEQ ID NO: 171, and SEQ ID NO: 172, respectively;

(t) wherein the heavy chain CDR1, CDR2, and CDR3 comprises SEQ ID NO: 173, SEQ ID NO: 174, and SEQ ID NO: 175, respectively; and wherein the light chain CDR1, CDR2, and CDR3 comprises SEQ ID NO: 176, SEQ ID NO: 177, and SEQ ID NO: 178, respectively;

(u) wherein the heavy chain CDR1, CDR2, and CDR3 comprises SEQ ID NO: 179, SEQ ID NO: 180, and SEQ ID NO: 181, respectively; and wherein the light chain CDR1, CDR2, and CDR3 comprises SEQ ID NO: 182, SEQ ID NO: 183, and SEQ ID NO: 184, respectively;

(v) wherein the heavy chain CDR1, CDR2, and CDR3 comprises SEQ ID NO: 185, SEQ ID NO: 186, and SEQ ID NO: 187, respectively; and wherein the light chain CDR1, CDR2, and CDR3 comprises SEQ ID NO: 188, SEQ ID NO: 189, and SEQ ID NO: 190, respectively;

(w) wherein the heavy chain CDR1, CDR2, and CDR3 comprises SEQ ID NO: 191, SEQ ID NO: 192, and SEQ ID NO: 193, respectively; and wherein the light chain CDR1, CDR2, and CDR3 comprises SEQ ID NO: 194, SEQ ID NO: 195, and SEQ ID NO: 196, respectively;

(x) wherein the heavy chain CDR1, CDR2, and CDR3 comprises SEQ ID NO: 197, SEQ ID NO: 198, and SEQ ID NO: 199, respectively; and wherein the light chain CDR1, CDR2, and CDR3 comprises SEQ ID NO: 200, SEQ ID NO: 201, and SEQ ID NO: 202, respectively;

(y) wherein the heavy chain CDR1, CDR2, and CDR3 comprises SEQ ID NO: 203, SEQ ID NO: 204, and SEQ ID NO: 205, respectively; and wherein the light chain CDR1, CDR2, and CDR3 comprises SEQ ID NO: 206, SEQ ID NO: 207, and SEQ ID NO: 208, respectively;

(z) wherein the heavy chain CDR1, CDR2, and CDR3 comprises SEQ ID NO: 209, SEQ ID NO: 210, and SEQ ID NO: 211, respectively; and wherein the light chain CDR1, CDR2, and CDR3 comprises SEQ ID NO: 212, SEQ ID NO: 213, and SEQ ID NO: 214, respectively;

(aa) wherein the heavy chain CDR1, CDR2, and CDR3 comprises SEQ ID NO: 215, SEQ ID NO: 216, and SEQ ID NO: 217, respectively; and wherein the light chain CDR1, CDR2, and CDR3 comprises SEQ ID NO: 218, SEQ ID NO: 219, and SEQ ID NO: 220, respectively; or (ab) wherein the heavy chain CDR1, CDR2, and CDR3 comprises SEQ ID NO: 221, SEQ ID NO: 222, and SEQ ID NO: 223, respectively; and wherein the light chain CDR1, CDR2, and CDR3 comprises SEQ ID NO: 224, SEQ ID NO: 225, and SEQ ID NO: 226, respectively.

In one embodiment of the first aspect of the present invention, the antibody or antigen-binding fragment thereof comprises a heavy chain variable region and a light chain variable region, (a) wherein the heavy chain variable region comprises SEQ ID NO: 1 and the light chain variable region comprises SEQ ID NO: 2;

(b) wherein the heavy chain variable region comprises SEQ ID NO: 3 and the light chain variable region comprises SEQ ID NO: 4;

(c) wherein the heavy chain variable region comprises SEQ ID No. 5 and the light chain variable region comprises SEQ ID NO: 6;

(d) wherein the heavy chain variable region comprises SEQ ID NO: 7 and the light chain variable region comprises SEQ ID NO: 8;

(e) wherein the heavy chain variable region comprises SEQ ID NO: 9 and the light chain variable region comprises SEQ ID NO: 10

(f) wherein the heavy chain variable region comprises SEQ ID NO: 11 and the light chain variable region comprises SEQ ID NO: 12;

(g) wherein the heavy chain variable region comprises SEQ ID NO: 13 and the light chain variable region comprises SEQ ID NO: 14;

(h) wherein the heavy chain variable region comprises SEQ ID NO: 15 and the light chain variable region comprises SEQ ID NO: 16;

(i) wherein the heavy chain variable region comprises SEQ ID NO: 17 and the light chain variable region comprises SEQ ID NO: 18;

(j) wherein the heavy chain variable region comprises SEQ ID NO: 19 and the light chain variable region comprises SEQ ID NO: 20;

(k) wherein the heavy chain variable region comprises SEQ ID NO: 21 and the light chain variable region comprises SEQ ID NO: 22;

(l) wherein the heavy chain variable region comprises SEQ ID NO: 23 and the light chain variable region comprises SEQ ID NO: 24;

(m) wherein the heavy chain variable region comprises SEQ ID NO: 25 and the light chain variable region comprises SEQ ID NO: 26;

(n) wherein the heavy chain variable region comprises SEQ ID NO: 27 and the light chain variable region comprises SEQ ID NO: 28;

(o) wherein the heavy chain variable region comprises SEQ ID NO: 29 and the light chain variable region comprises SEQ ID NO: 30;

(p) wherein the heavy chain variable region comprises SEQ ID NO: 31 and the light chain variable region comprises SEQ ID NO: 32;
(q) wherein the heavy chain variable region comprises SEQ ID NO: 33 and the light chain variable region comprises SEQ ID NO: 34;
(r) wherein the heavy chain variable region comprises SEQ ID NO: 35 and the light chain variable region comprises SEQ ID NO: 36;
(s) wherein the heavy chain variable region comprises SEQ ID NO: 37 and the light chain variable region comprises SEQ ID NO: 38;
(t) wherein the heavy chain variable region comprises SEQ ID NO: 39 and the light chain variable region comprises SEQ ID NO: 40;
(u) wherein the heavy chain variable region comprises SEQ ID NO: 41 and the light chain variable region comprises SEQ ID NO: 42;
(v) wherein the heavy chain variable region comprises SEQ ID NO: 43 and the light chain variable region comprises SEQ ID NO: 44;
(w) wherein the heavy chain variable region comprises SEQ ID NO: 45 and the light chain variable region comprises SEQ ID NO: 46;
(x) wherein the heavy chain variable region comprises SEQ ID NO: 47 and the light chain variable region comprises SEQ ID NO: 48;
(y) wherein the heavy chain variable region comprises SEQ ID NO: 49 and the light chain variable region comprises SEQ ID NO: 50;
(z) wherein the heavy chain variable region comprises SEQ ID NO: 51 and the light chain variable region comprises SEQ ID NO: 52;
(aa) wherein the heavy chain variable region comprises SEQ ID NO: 53 and the light chain variable region comprises SEQ ID NO: 54; or
(ab) wherein the heavy chain variable region comprises SEQ ID NO: 55 and the light chain variable region comprises SEQ ID NO: 56.

According to another embodiment of the first aspect of the present invention, the SARS-related coronavirus strain is severe acute respiratory syndrome coronavirus 2 (SARS-CoV-2).

According to yet another embodiment of the first aspect of the present invention, the antibody or antigen-binding fragment thereof is directed against the ectodomain of the spike (S) protein of SARS-CoV-2, including, for example, against the ectodomain of the spike (S) homotrimer of SARS-CoV-2 in the prefusion-stabilized-variant of the virus isolate Wuhan-Hu-1 as described in Wrapp et al., Science (2020) doi: 10.1126/science.abb2507 (SEQ ID NO. 57), or the receptor-binding domain (RBD) of the spike (S) protein of SARS-CoV-2. In an embodiment, the RBD of the spike (S) protein of SARS-CoV-2 has the sequence set forth in SEQ ID NO. 58.

According to an embodiment of the first aspect of the present invention, the antibody or antigen-binding fragment thereof exhibits a neutralization potency against SARS-CoV-2 isolate BavPat1/2020 on VeroE6 cells ($IC_{100}$; lowest antibody dose leading to the complete absence of cytopathic effects) of less than 10 μg/ml when tested in a virus neutralization test using 100 $TCID_{50}$ of SARS-CoV-2 applied to VeroE6 cells following a 1 hour co-incubation of virus and antibody at 37° C. based on the assay described in Koch et al., *Lancet Infect. Dis.* (2020) doi:10.1016/s1473-3099(20)30248-6.

According to a further embodiment of the first aspect of the present invention, the antibody or antigen-binding fragment thereof exhibits a neutralization potency of less than 1 μg/ml.

According to a further embodiment of the first aspect of the present invention, the antibody or antigen-binding fragment thereof exhibits a neutralization potency of less than 0.5 μg/ml.

According to a further embodiment of the first aspect of the present invention, the antibody or antigen-binding fragment thereof exhibits a neutralization potency of 0.25 μg/ml or less.

According to another embodiment of the present invention, the antibody or antigen-binding fragment thereof binds to both Region 1 and Region 2 of the ectodomain of the spike (S) protein of SARS-CoV-2.

According to another embodiment of the present invention, the antibody or antigen-binding fragment thereof does not display autoreactivity. In an embodiment, autoreactivity is defined as detectable binding when tested against permeabilized HEp-2 cells using an antinuclear antibody (ANA) testing kit (NOVA-Lite HEp-2 ANA kit; Inova Diagnostics) at concentrations of 100 μg/ml of the antibody or antigen-binding fragment thereof.

According to another embodiment of the present invention, the isolated antibody or antigen-binding fragment thereof specifically binds to the ectodomain of the spike (S) homotrimer of SARS-CoV-2 (SEQ ID NO. 57) and/or against the receptor-binding domain (RBD) of the spike (S) protein of SARS-CoV-2 (SEQ ID NO. 58), and comprises a heavy chain CDR1, CDR2, CDR3 and a light chain CDR1, CDR2, CDR3, wherein the heavy chain CDR1, CDR2, and CDR3 comprises GFTFRRYG (SEQ ID NO: 119), ILFDGSNK (SEQ ID NO: 120) and AKGGDYEWELLES (SEQ ID NO: 121), respectively; and wherein the light chain CDR1, CDR2, and CDR3 comprises QSIDNW (SEQ ID NO: 122), KAS (SEQ ID NO: 123), and QHYHSFPLT (SEQ ID NO: 124), respectively.

According to another embodiment of the present invention, the antibody or antigen-binding fragment thereof comprises a heavy chain variable region and a light chain variable region, wherein the heavy chain variable region comprises SEQ ID NO: 21 and the light chain variable region comprises SEQ ID NO: 22.

According to another embodiment of the present invention, the heavy chain of the antibody has an amino acid sequence of SEQ ID No. 229 and the light chain of the antibody has an amino acid sequence of SEQ ID No. 230. According to another embodiment of the present invention, the antibody consists of two heavy chains of SEQ ID NO: 229 and two light chains of SEQ ID NO: 230.

According to the second aspect of the present invention, a pharmaceutical composition is provided comprising an antibody or antigen-binding fragment thereof according to the first aspect of the present invention, and at least one pharmaceutically acceptable excipient.

According to an embodiment of the second aspect of the present invention, the pharmaceutical composition is a vaccination composition for a human and/or animal subject.

According to the third aspect of the present invention, a kit is provided comprising an antibody or antigen-binding fragment thereof according to the first aspect of the present invention, and a container.

According to the fourth aspect of the present invention, an antibody or antigen-binding fragment thereof according to the first aspect of the invention, a pharmaceutical composition according to the second aspect of the invention, or a kit according to the third aspect of the invention are provided for use as a medicament (e.g., as a vaccine).

According to the fifth aspect of the present invention, an antibody or antigen-binding fragment thereof according to the first aspect of the invention, a pharmaceutical composition according to the second aspect of the invention, or a kit according to the third aspect of the invention are provided for use in the treatment and/or prevention of a disease caused by SARS-related coronavirus in human or animal subjects (e.g., for use in the treatment and/or prevention of a disease caused by severe acute respiratory syndrome coronavirus 2 (SARS-CoV-2) in human or animal subjects).

According to the sixth aspect of the present invention, an antibody or antigen-binding fragment thereof according to the first aspect of the invention, a pharmaceutical composition according to the second aspect of the invention, or a kit according to the third aspect of the invention are provided for use in prevention of infection of a human or animal subject with SARS-related coronavirus (e.g., an infection of a human or animal subject with severe acute respiratory syndrome coronavirus 2 (SARS-CoV-2)).

According to the seventh aspect of the present invention, a method of treating a SARS-related coronavirus in a human or animal subject comprises administering a therapeutically effective amount of at least one antibody and/or antigen-binding fragment thereof as described herein to said human or animal subject. In one aspect the subject is a human subject.

According to the eighth aspect of the present invention, a method of preventing infection of a human and/or animal subject with SARS-related coronavirus comprises administering a therapeutically effective amount of at least one antibody and/or antigen-binding fragment thereof as described herein to said human or animal subject. In one aspect the subject is a human subject.

According to the ninth aspect of the present invention, a method of reducing the severity of disease in a human or animal subject with SARS-related coronavirus comprises administering a therapeutically effective amount of at least one antibody and/or antigen-binding fragment thereof as described herein to said human or animal subject. In one aspect the subject is a human subject.

According to an embodiment of the fourth aspect, of the fifth aspect, of the sixth aspect, of the seventh aspect, of the eighth aspect, or of the ninth aspect of the present invention, the antibody or antigen-binding fragment thereof is administered by intravenous infusion. In an embodiment, the antibody or antigen-binding fragment thereof is administered at a dose of about 1 mg/kg body weight to about 100 mg/kg body weight of a subject (e.g., wherein the antibody or antigen-binding fragment thereof may be administered at a dose of about 2.5 mg/kg, about 5 mg/kg, about 10 mg/kg, about 20 mg/kg, about 25 mg/kg, about 30 mg/kg, about 40 mg/kg, about 50 mg/kg, or about 100 mg/kg).

According to another embodiment of the fourth aspect, of the fifth aspect, of the sixth aspect, of the seventh aspect, of the eighth aspect, or of the ninth aspect of the present invention, the antibody or antigen-binding fragment thereof is administered by inhalative application. In an embodiment, wherein the antibody or antigen-binding fragment thereof is provided in a liquid pharmaceutical composition which may be nebulized by a mesh nebulizer or a jet nebulizer prior to administration. In a further embodiment, the antibody or antigen-binding fragment thereof may be administered at a dose of about 50 mg, about 100 mg, about 200 mg, about 250 mg, about 300 mg, about 400 mg, about 500 mg, about 750 mg, or about 1000 mg.

In another embodiment, the antibodies or antigen-binding fragments thereof of the present invention are administered via inhalation as an initial dose followed by systemic administration such as, but not limited to, intravenous administration and/or intraperitoneal administration.

In another embodiment, the antibody or antigen-binding fragment thereof is administered in combination with at least one further antibody or antigen-binding fragment thereof directed against SARS-related coronavirus 2 (SARS-CoV-2), wherein said at least one further antibody or antigen-binding fragment thereof has a different binding specificity. In one embodiment, the further antibody or antigen-binding fragment thereof is a second antibody or antigen-binding fragment as described herein. In one embodiment, the further antibody or antigen-binding fragment thereof is directed against and/or has specificity for a variant of the virus isolate Wuhan-Hu-1.

According to another embodiment, methods of treating a SARS-related coronavirus in a human or animal subject are provided comprising administering a therapeutically effective amount of at least one antibody and/or antigen-binding fragment thereof or pharmaceutical composition comprising at least one antibody and/or antigen-binding fragment thereof of the present invention to said human or animal subject.

According to another embodiment, methods are provided for preventing infection of a human or animal subject with SARS-related coronavirus comprising administering a therapeutically effective amount of at least one antibody and/or antigen-binding fragment thereof or pharmaceutical composition comprising at least one antibody and/or antigen-binding fragment thereof of the present invention to said human or animal subject.

In yet another embodiment, methods are provided for reducing the severity of disease in a human or animal subject with SARS-related coronavirus comprising administering a therapeutically effective amount of at least one antibody and/or antigen-binding fragment thereof or pharmaceutical composition comprising at least one antibody and/or antigen-binding fragment of the present invention to said human or animal subject.

In one embodiment, the SARS-related coronavirus is SARS-CoV-2. In another embodiment, the subject is a human. In yet another embodiment, the subject is an animal.

In another aspect, the present invention provides a nucleic acid encoding the antibody or antigen binding fragment thereof as described herein.

In another aspect, the present invention provides an expression vector comprising the nucleic acid as described herein.

In another aspect, the present invention provides a host cell comprising the nucleic acid as described herein, in functional association with an expression control sequence.

In another aspect, the present invention provides a method of producing the antibody or antigen binding fragment thereof as described herein, comprising: (a) cultivating the host cell as described herein under conditions allowing expression of the antibody or antigen binding fragment thereof, and (b) recovering the antibody or antigen binding fragment thereof.

BRIEF DESCRIPTION OF FIGURES

FIG. 4 shows autoreactivity of selected SARS-CoV-2 binding and neutralizing antibodies as tested by staining HEp-2 cells with SARS-CoV-2 S-ectodomain antibodies and analysis by fluorescence microscopy (Leica DMI microscope 6000); representative pictures of the scoring system are shown.

FIGS. 5A-D show an extended data table with a summary of characteristics of isolated SARS-COV-2 interacting antibodies.

FIG. 6A shows the experimental scheme with numbers indicating experimental days. FIG. 6B shows SARS-CoV-2 genome copies per nanogram RNA in pulmonary tissues on day 4. FIG. 6C shows $TCID_{50}$ titer determined by virus isolation from 25 mg lung tissue homogenate on Vero E6 cells. i.n., intranasally. i.p., intraperitoneally.

FIG. 7A shows the experimental scheme with numbers indicating experimental days. FIG. 7B shows SARS-CoV-2 titer determined by qRT-PCR in nasal swabs. FIG. 7C shows SARS-CoV-2 titer determined by qRT-PCR in lung homogenates. FIG. 7D shows infectious SARS-CoV-2 titer determined by virus isolation from different pulmonary lobes.

FIG. 11A shows stability data at intended storage condition (5° C.) of DZIF-10c in formulations F5-F8 in terms of percentage of high molecular weight species (HMW).

FIG. 14 shows properties of DZIF-10c compared to antibodies REGN10987 and REGN10933.

DETAILED DESCRIPTION OF THE INVENTION

Figure 1A:
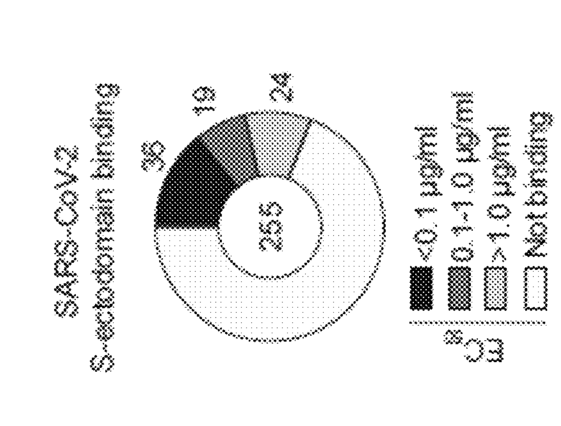
FIG. 1A shows the interaction of 255 isolated human monoclonal antibodies with the SARS-CoV-2 S-ectodomain as identified by ELISA; 79 binding antibodies (black to dark grey) were identified by defining cut-off values of an $EC_{50}$<30 μg/ml and an $OD_{415-695}$>0.25 (not shown)

In order that the present description can be more readily understood, certain terms are first defined. Additional definitions are set forth throughout the detailed description.

It is to be noted that the term "a" or "an" entity refers to one or more of that entity; for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International d'Unités (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The term "antibody" is used herein in the broadest sense to refer to molecules with an immunoglobulin-like domain (for example IgG, IgM, IgA, IgD or IgE) and includes monoclonal, recombinant, polyclonal, chimeric, human, humanized, multispecific antibodies, including bispecific antibodies, and heteroconjugate antibodies; a single variable domain (e.g., $V_H$, $V_{HH}$, $V_L$, domain antibody), antigen binding antibody fragments, Fab, $F(ab')_2$, Fv, disulphide linked Fv, single chain Fv, disulphide-linked scFv, diabodies, etc. and modified versions of any of the foregoing. The term "antibody" as used herein refers to a protein, derived from a germline immunoglobulin sequence, which is capable of specifically binding to an antigen or an antigen-binding portion thereof. The term includes full length antibodies of any class or isotype (that is, IgA, IgE, IgG, IgM and/or IgY) and any single chain or fragment thereof. An antibody that specifically binds to an antigen, or antigen-binding portion thereof, may bind exclusively to that antigen, or portion thereof, or it may bind to a limited number of homologous antigens, or portions thereof. Full-length antibodies usually comprise at least four polypeptide chains: two heavy (H) chains and two light (L) chains that are interconnected by disulfide bonds. One immunoglobulin sub-class of particular pharmaceutical interest is the IgG family. In humans, the IgG class may be sub-divided into 4 sub-classes: $IgG_1$, $IgG_2$, $IgG_3$ and $IgG_4$, based on the sequence of their heavy chain constant regions. The light chains can be divided into two types, kappa and lambda, based on differences in their sequence composition. IgG molecules are composed of two heavy chains, interlinked by two or more disulfide bonds, and two light chains, each attached to a heavy chain by a disulfide bond. A heavy chain may comprise a heavy chain variable region (VH) and up to three heavy chain constant (CH) regions: CH1, CH2 and CH3. A light chain may comprise a light chain variable region (VL) and a light chain constant region (CL). VH and VL regions can be further subdivided into regions of hypervariability, termed complementarity determining regions (CDRs), interspersed with regions that are more conserved, termed framework regions (FR). VH and VL regions are typically composed of three CDRs and four FRs, arranged from amino-terminus to carboxy-terminus in the following order: FR1, CDR1, FR2, CDR2, FR3, CDR3, FR4. The hypervariable regions of the heavy and light chains form a binding domain that is capable of interacting with an antigen, while the constant region of an antibody may mediate binding of the immunoglobulin to host tissues or factors, including but not limited to various cells of the immune system (effector cells), Fc receptors and the first component (C1q) of the classical complement system. Antibodies of the current invention may be isolated.

The terms "monoclonal antibody" or "mAb" as used herein refers to an antibody obtained from a population of substantially homogeneous antibodies, e.g., the individual antibodies comprising the population are identical and/or bind the same epitope, except for possible variant antibodies, e.g., containing naturally occurring mutations or arising during production, purification and/or storage of a monoclonal antibody preparation. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any method. For example, the monoclonal antibodies to be used in accordance with the present disclosure may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "isolated antibody" refers to an antibody that has been separated and/or recovered from (an)other component(s) in the environment in which it was produced and/or that has been purified from a mixture of components present in the environment in which it was produced. Certain antigen-binding fragments of antibodies may be suitable in the context of the current invention, as it has been shown that the antigen-binding function of an antibody can be performed by fragments of a full-length antibody.

The term "antigen-binding portion," "binding fragment," or "antigen-binding fragment" of an antibody refers to one or more fragment(s) of an antibody that retain the ability to specifically bind to an antigen, such as the spike (S) protein of SARS-CoV-2, as described herein. Examples of antigen-binding fragments include Fab, Fab', F(ab)2, F(ab')2, F(ab) S, Fv (typically the VL and VH domains of a single arm of an antibody), single-chain Fv (scFv; see, e.g., Bird et al., Science 242:42S-426 (1988); Huston et al., PNAS 85: 5879-5883 (1988)), dsFv, Fd (typically the VH and CH1 domain), and dAb (typically a $V_H$ domain) fragments; $V_H$, $V_L$, $V_{HH}$, and V-NAR domains; monovalent molecules comprising a single VH and a single VL chain; minibodies, diabodies, triabodies, tetrabodies, and kappa bodies (see, e.g., Ill et al., Protein Eng 10:949-57 (1997)); camel IgG; IgNAR; as well as one or more isolated CDRs or a functional paratope, where the isolated CDRs or antigen-binding residues or polypeptides can be associated or linked together so as to form a functional antibody fragment. Various types of antibody fragments have been described or reviewed in, e.g., Holliger and Hudson, Nat Biotechnol 2S:1126-1136 (2005); International Publ. No. WO 2005/040219, and U.S. Publ. Nos. 2005/0238646 and 2002/0161201. These antibody fragments may be obtained using conventional techniques known to those of skill in the art, and the fragments may be screened for utility in the same manner as intact antibodies.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The SARS-CoV-2 antibodies described herein can include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are used synonymously.

A "humanized" antibody refers to a human/non-human chimeric antibody that contains one or more sequences (CDR regions or parts thereof) that are derived from a non-human immunoglobulin. A humanized antibody is, thus, a human immunoglobulin (recipient antibody) in which at least residues from a hyper-variable region of the recipient are replaced by residues from a hyper-variable region of an antibody from a non-human species (donor antibody) such as from a mouse, rat, rabbit or non-human primate, which have the desired specificity, affinity, sequence composition and functionality. In some instances, FR residues of the human immunoglobulin are replaced by corresponding non-human residues. An example of such a modification is the introduction of one or more so-called back-mutations, which are typically amino acid residues derived from the donor antibody. Humanization of an antibody may be carried out using recombinant techniques known to the person skilled in the art (see, e.g., Antibody Engineering, Methods in Molecular Biology, vol. 248, edited by Benny K. C. Lo). A suitable human recipient framework for both the light and heavy chain variable domain may be identified by, for example, sequence or structural homology. Alternatively, fixed recipient frameworks may be used, e.g., based on knowledge of structure, biophysical and biochemical properties. The recipient frameworks can be germline derived or derived from a mature antibody sequence. CDR regions from the donor antibody can be transferred by CDR grafting. The CDR grafted humanized antibody can be further optimized for e.g. affinity, functionality and biophysical properties by identification of critical framework positions where re-introduction (backmutation) of the amino acid residue from the donor antibody has beneficial impact on the properties of the humanized antibody. In addition to donor antibody derived backmutations, the humanized antibody can be engineered by introduction of germline residues in the CDR or framework regions, elimination of immunogenic epitopes, site-directed mutagenesis, affinity maturation, etc.

Furthermore, humanized antibodies can comprise residues that are not found in the recipient antibody or in the donor antibody. These modifications are made to further refine antibody performance. In general, a humanized antibody will comprise at least one—typically two—variable domains, in which all or substantially all of the CDR regions correspond to those of a non-human immunoglobulin and in which all or substantially all of the FR residues are those of a human immunoglobulin sequence. The humanized antibody can, optionally, also comprise at least a portion of an immunoglobulin constant region (Fc), typically that of a human immunoglobulin. The term "humanized antibody derivative" refers to any modified form of the humanized antibody, such as a conjugate of the antibody and another agent or antibody.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg Nature Biotech. 23(9): 1117-1125 (2005)), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (i.e., have at least 80% identity).

A "chimeric antibody" refers to an antibody in which the variable regions are derived from one species and the constant regions are derived from another species, such as an antibody in which the variable regions are derived from a mouse antibody and the constant regions are derived from a human antibody.

Alternative antibody formats include alternative scaffolds in which the one or more CDRs of the antigen-binding portion can be arranged onto a suitable non-immunoglobulin protein scaffold or skeleton, such as an affibody, a SpA scaffold, an LDL receptor class A domain, an avimer or an EGF domain.

The term "domain" refers to a folded protein structure which retains its tertiary structure independent of the rest of the protein. Generally, domains are responsible for discrete functional properties of proteins and in many cases may be added, removed or transferred to other proteins without loss of function of the remainder of the protein and/or of the domain.

The term "single variable domain" refers to a folded polypeptide domain comprising sequences characteristic of antibody variable domains. It, therefore, includes complete antibody variable domains such as $V_H$, $V_{HH}$ and $V_L$ and modified antibody variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain. A single variable domain is capable of binding an antigen or epitope independently of a different variable region or domain. A "domain antibody" or "dAb™" may be considered the same as a "single variable domain". A single variable domain may be a human single variable domain, but also includes single variable domains from other species such as rodent, nurse shark and Camelid $V_{HH}$ dAbs™. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanized according to standard techniques available in the art, and such domains are considered to be "single variable domains". As used herein $V_H$ includes camelid $V_{HH}$ domains.

An antigen-binding fragment may be provided by means of arrangement of one or more CDRs on non-antibody protein scaffolds. "Protein Scaffold" as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al., mAbs 1:1 (2009)).

The phrases "an antibody recognizing an antigen" and "an antibody specific for an antigen" are used interchangeably herein with the term "an antibody which binds specifically to an antigen."

By the terms "treat," "treating," or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition.

As used herein, the terms "prevent," "prevents," or "prevention" and "inhibit," "inhibits," or "inhibition" (and grammatical equivalents thereof) are not meant to imply complete abolition of disease and encompasses any type of prophylactic treatment that reduces the incidence of the condition, delays the onset of the condition, and/or reduces the symptoms associated with the condition after onset.

An "effective," "prophylactically effective," or "therapeutically effective" amount as used herein is an amount that is sufficient to provide some improvement or benefit to the subject. Alternatively stated, an "effective," "prophylactically effective," or "therapeutically effective" amount is an amount that will provide some delay, alleviation, mitigation, or decrease in at least one clinical symptom in the subject. Those skilled in the art will appreciate that the effects need not be complete or curative, as long as some benefit is provided to the subject.

As used herein, a "neutralizing antibody" is any antibody or antigen-binding fragment thereof that binds to a pathogen and interferes with the ability of the pathogen to infect a cell and/or cause disease in a subject.

"Peptide" as used herein includes peptides which are conservative variations of those peptides specifically exemplified herein. "Conservative variations" and "Conservative amino acid substitutions" as used herein denotes the replacement of an amino acid residue by another, biologically similar residue. Examples of conservative variations include, but are not limited to, the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine. "Conservative variations" also includes the use of a substituted amino acid in place of an unsubstituted parent amino acid provided that antibodies raised to the substituted polypeptide also immunoreact with the unsubstituted polypeptide. Such conservative substitutions are within the definition of the classes of the peptides of the invention. The biological activity of the peptides can be determined by standard methods known to those of skill in the art and described herein.

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available at worldwideweb.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4: 11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. (48):444-453 (1970)) algorithm which has been incorporated into the GAP program in the GCG software package (available at worldwideweb.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) Nucleic Acids Res. 25(17):3389-3402. When utilizing BLAST and Gapped BLAST programs, the default parameters of the respective programs (e.g., XBLAST and NBLAST) can be used. See worldwideweb.ncbi.nlm.nih.gov.

The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, can be mutated, in accordance with standard techniques to provide gene sequences. For coding sequences, these mutations, can affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors") In general, expression vectors of utility in recombinant DNA techniques are often in the form of plasmids. In the present specification, "plasmid" and "vector" can be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and can be a cell into which a recombinant expression vector has been introduced. It should be understood that such terms are intended to refer not only to the particular subject cell but to the progeny of such a cell. Because certain modifications can occur in succeeding generations due to either mutation or environmental influences, such progeny cannot, in fact, be identical to the parent cell, but are still included within the scope of the term "host cell" as used herein.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

An "Fc receptor" or "FcR" is a receptor that binds to the Fc region of an immunoglobulin. FcRs that bind to an IgG antibody comprise receptors of the Fc.γR family, including allelic variants and alternatively spliced forms of these receptors. The FcγR family consists of three activating (FcγRI, FcγRIII, and Fc.RIV in mice; FcγRIA, FcγRIIA, and FcγRIIIA in humans) and one inhibitory (FcγRIIB) receptor. Various properties of human FcγRs are known in the art. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

"Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL).

In IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat. The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesion).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs (see, e.g., Jefferis et al., mAbs 1: 1 (2009)).

A "variant sequence Fc region" or "non-naturally occurring Fc" comprises a modification, typically to alter one or more of its functional properties, such as serum half-life, complement fixation, Fc-receptor binding, protein stability and/or antigen-dependent cellular cytotoxicity, or lack thereof, among others. In some embodiments, the antibodies of the present disclosure can be chemically modified (e.g., one or more chemical moieties can be attached to the antibody) or be modified to alter its glycosylation, again to alter one or more functional properties of the antibody.

The terms "hinge," "hinge domain," "hinge region," and "antibody hinge region" refer to the domain of a heavy chain constant region that joins the CH1 domain to the CH2 domain and includes the upper, middle, and lower portions of the hinge (Roux et al., J Immunol 161:4083 (1998)). The hinge provides varying levels of flexibility between the binding and effector regions of an antibody and also provides sites for intermolecular disulfide bonding between the two heavy chain constant regions. As used herein, a hinge starts at Glu216 and ends at Gly237 of all IgG isotypes (Roux et al., J Immunol 161:4083 (1998)). The sequence of wildtype IgG1, IgG2, IgG3, and IgG4 hinges are known in the art (e.g., International PCT publication no. WO 2017/087678). In one embodiment, the hinge region of CH1 of the antibodies is modified such that the number of cysteine residues in the hinge region is altered, e.g., increased or decreased. This approach is described further for instance in U.S. Pat. No. 5,677,425.

The constant region may be modified to stabilize the antibody, e.g., to reduce the risk of a bivalent antibody separating into two monovalent VH-VL fragments. For example, in an IgG4 constant region, residue S228 (residue numbering according to the EU index) may be mutated to a proline (P) residue to stabilize inter heavy chain disulphide bridge formation at the hinge (see, e.g., Angal et al., Mol Immunol. 30: 105-8(1995)). Antibodies or fragments thereof can also be defined in terms of their complementarity-determining regions (CDRs). The term "complementarity-determining region" or "hypervariable region", when used herein, refers to the regions of an antibody in which amino acid residues involved in antigen binding are situated. The region of hypervariability or CDRs can be identified as the regions with the highest variability in amino acid alignments of antibody variable domains. Databases can be used for CDR identification such as the Kabat database, the CDRs e.g., being defined as comprising amino acid residues 24-34 (CDR1), 50-59 (CDR2) and 89-97 (CDR3) of the light-chain variable domain, and 31-35 (CDR1), 50-65 (CDR2) and 95-102 (CDR3) in the heavy-chain variable domain (Kabat et al. 1991; Sequences of Proteins of Immunological Interest, Fifth Edition, U.S. Department of Health and Human Services, NIH Publication No. 91-3242). Alternatively CDRs can be defined as those residues from a "hypervariable loop" (residues 26-33 (L1), 50-52 (L2) and 91-96 (L3) in the light-chain variable domain and 26-32 (H1), 53-55 (H2) and 96-101 (H3) in the heavy-chain variable domain (Chothia and Lesk, J. Mol. Biol 196: 901-917 (1987)). Typically, the numbering of amino acid residues in this region is performed by the method described in Kabat et al., supra. Phrases such as "Kabat position", "Kabat residue", and "according to Kabat" herein refer to this numbering system for heavy chain variable domains or light chain variable domains. Using the Kabat numbering system, the actual linear amino acid sequence of a peptide may contain fewer or additional amino acids corresponding to a shortening of, or insertion into, a framework (FR) or CDR of the variable domain. For example, a heavy chain variable domain may include amino acid insertions (residue 52a, 52b and 52c according to Kabat) after residue 52 of CDR H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The term "epitope" or "antigenic determinant" refers to a site on an antigen to which an immunoglobulin or antibody specifically binds, e.g., as defined by the specific method used to identify it. Epitopes can be formed both from contiguous amino acids (usually a linear epitope) or non-contiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from the spike (S) protein of SARS-CoV-2) are tested for reactivity with a given antibody. Methods of determining spatial conformation of epitopes include techniques in the art and those described herein, for example, x-ray crystallography, antigen mutational analysis, 2-dimensional nuclear magnetic resonance and HDX-MS (see, e.g., Epitope Mapping Protocols in Methods in Molecular Biology, Vol. 66, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same $V_H$ and $V_L$ or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, can be determined using known competition experiments, e.g., BIACORE® surface plasmon resonance (SPR) analysis. In certain embodiments, an antibody competes with, and inhibits binding of another antibody to a target by at least 50%, 60%, 70%, 80%, 90% or 100%. The level of inhibition or competition can be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi: 10.1101/pdb.prot4277 or in Chapter 11 of "Using Antibodies" by Ed Harlow and David Lane, Cold Spring Harbor Laboratory Press, Cold Spring Harbor, N.Y., USA 1999. Two antibodies "cross-compete" if antibodies block each other both ways by at least 50%, i.e., regardless of whether one or the other antibody is contacted first with the antigen in the competition experiment.

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$ M or $10^{-10}$ M or even lower when determined by, e.g., surface plasmon resonance (SPR) technology in a BIACORE® 2000 instrument using the predetermined antigen as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen.

The term "binding affinity" herein refers to a measurement of the strength of a non-covalent interaction between two molecules, e.g. an antibody, or fragment thereof, and an antigen. The term "binding affinity" is used to describe monovalent interactions (intrinsic activity). The binding affinity between two molecules, e.g. an antibody, or fragment thereof, and an antigen, through a monovalent interaction may be quantified by determination of the equilibrium dissociation constant ($K_D$). In turn, $K_D$ can be determined by measurement of the kinetics of complex formation and dissociation, e.g. by the SPR method. The rate constants corresponding to the association and the dissociation of a monovalent complex are referred to as the association rate constant $k_a$ (or $k_{on}$) and dissociation rate constant $k_d$ (or $k_{off}$), respectively. $K_D$ is related to $k_a$ and $k_d$ through the equation $K_D=k_d/k_a$. Following the above definition, binding affinities associated with different molecular interactions, such as comparison of the binding affinity of different antibodies fora given antigen, may be compared by comparison of the $K_D$ values for the individual antibody/antigen complexes.

The term "binding specificity" herein refers to the interaction of a molecule such as an antibody, or fragment thereof, with a single exclusive antigen, or with a limited number of highly homologous antigens (or epitopes).

The specificity of an interaction and the value of an equilibrium binding constant can be determined directly by well-known methods. Standard assays to evaluate the ability of ligands (such as antibodies) to bind their targets are known in the art and include, for example, ELISAs, Western blots, RIAs, and flow cytometry analysis. The binding kinetics and binding affinity of the antibody also can be assessed by standard assays known in the art, such as SPR.

As used herein, the term "bin" is defined using a reference antibody. If a second antibody is unable to bind to an antigen at the same time as the reference antibody, the second antibody is said to belong to the same "bin" as the reference antibody. In this case, the reference and the second antibody competitively bind the same part of an antigen and are coined "competing antibodies". If a second antibody is capable of binding to an antigen at the same time as the reference antibody, the second antibody is said to belong to a separate "bin". In this case, the reference and the second antibody do not competitively bind the same part of an antigen and are coined "non-competing antibodies".

Antibody "binning" does not provide direct information about the epitope. Competing antibodies, i.e., antibodies belonging to the same "bin" can have identical epitopes, overlapping epitopes, or even separate epitopes. The latter is the case if the reference antibody bound to its epitope on the antigen takes up the space required for the second antibody to contact its epitope on the antigen ("steric hindrance"). Non-competing antibodies generally have separate epitopes.

The term "$EC_{50}$" in the context of an in vitro or in vivo assay using an antibody or antigen-binding fragment thereof, refers to the concentration of an antibody or an antigen-binding portion thereof that induces a response that is 50% of the maximal response, i.e., halfway between the maximal response and the baseline.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein can contain a modification such as, but not limited to, glycosylation, phosphorylation or disulfide bond formation. A "protein" can comprise one or more polypeptides.

The term "nucleic acid molecule," as used herein, is intended to include DNA molecules and RNA molecules. A nucleic acid molecule can be single-stranded or double-stranded, and can be cDNA.

The term "subject" includes human and other mammalian subjects that receive either prophylactic or therapeutic treatment. As used herein, the term "subject" includes any human or non-human animal. The term "non-human animal" includes all vertebrates, e.g., mammals and non-mammals, such as non-human primates, sheep, dog, cow, chickens, amphibians, reptiles, etc.

As used herein, the terms "ug" and "uM" are used interchangeably with "μg" and "μM," respectively.

As used herein, "administering" refers to the physical introduction of a composition comprising a therapeutic agent to a subject, using any of the various methods and delivery systems known to those skilled in the art. Different routes of administration for the antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

The term "$C_{max}$" refers to the maximum or peak serum or plasma concentration of an agent observed in a subject after its administration.

As used herein "vaccination composition" means a pharmaceutical composition comprising at least one antibody or antigen-binding portion thereof of the present invention which is capable of providing active and/or passive immunity. "Active immunity" as used herein means inducing or enhancing a subject's immune response to an antigen. "Passive immunity" as used herein means supplementing a subject's immune response to an antigen or pathogen by providing antibodies and/or antigen-binding portions thereof which neutralize an antigen.

In one embodiment, the antibody or antigen-binding fragment thereof of the invention is administered intravenously and exhibits a maximum serum concentration ($C_{max}$) of between about 5 μg/mL and about 235 μg/mL; a $C_{max}$ of between about 5 μg/mL and about 8 μg/mL; a $C_{max}$ of between about 5 μg/mL and about 10 μg/mL; a $C_{max}$ of between about 55 μg/mL and about 90 μg/mL; a $C_{max}$ of between about 185 μg/mL and about 250 μg/mL; a $C_{max}$ of between about 190 μg/mL and about 235 μg/mL. In another embodiment, the $C_{max}$ is between about 5 μg/mL and about 50 μg/mL, between about 50 μg/mL and about 75 μg/mL, between about 75 μg/mL and about 100 μg/mL, between about 100 μg/mL and about 125 μg/mL, between about 125 μg/mL and about 150 μg/mL, between about 150 μg/mL and about 175 μg/mL, between about 175 μg/mL and about 200

μg/mL, or between about 200 μg/mL and about 235 μg/mL. In one embodiment, the $C_{max}$ is between about 1000 nmol/L to about 2000 nmol/L.

The term "$T_{max}$" refers to the time at which $C_{max}$ occurred. In one embodiment, the antibody, or antigen-binding portion thereof, of the invention is administered intravenously and exhibits a $T_{max}$ of between about 1 day and about 5 days; a $T_{max}$ of between about 3 days and about 5 days; a $T_{max}$ of less than or equal to about 5 days; a $T_{max}$ of about 1 day, a $T_{max}$ of about 2 days, a $T_{max}$ of about 3 days, a $T_{max}$ of about 4 days, a $T_{max}$ of about 5 days, a $T_{max}$ of about 6 days, a $T_{max}$ of about 7 days, a $T_{max}$ of about 8 days, a $T_{max}$ of about 9 days, or a $T_{max}$ of about 10 days.

The term "bioavailability" or "F %" refers to a fraction or percent of a dose which is absorbed and enters the systemic circulation after administration of a given dosage form. In another embodiment, the antibody, or antigen-binding portion thereof, exhibits a bioavailability of at least about 35%, at least about 40%, at least about 45%, at least about 50%, at least about 60%, at least about 65%, at least about 70%, at least about 75%, at least about 80%, at least about 85%, at least about 90%, at least about 95%, or at least about 100%.

As used herein "Area Under the Curve" or "AUC" is the area under the curve in a plot of the concentration of a substance in plasma against time. AUC can be a measure of the integral of the instantaneous concentrations during a time interval and has the units mass×time/volume, which can also be expressed as molar concentration x time such as nM×day. AUC is typically calculated by the trapezoidal method (e.g., linear, linear-log). AUC is usually given for the time interval zero to infinity, and other time intervals are indicated (for example AUC (t1,t2) where t1 and t2 are the starting and finishing times for the interval). Thus, as used herein "$AUC_{0-24h}$" refers to an AUC over a 24-hour period, and "$AUC_{0-4h}$" refers to an AUC over a 4-hour period. The term "AUC" or "area under the curve" is related to clearance. A higher clearance rate is related to a smaller AUC, and a lower clearance rate is related to a larger AUC value. The AUC higher values represent slower clearance rates.

As used herein "weighted mean AUC" is the AUC divided by the time interval over which the time AUC is calculated. For instance, weighted mean $AUC_{0-24h}$ would represent the $AUC_{0-24h}$ divided by 24 hours.

In one embodiment of the present invention, the antibody or antigen-binding fragment thereof has an Area Under the $Curve_{(0-inf)}$ value that is at least about 10.0 μg×day/mL. In one embodiment of the present invention, the antibody or antigen-binding fragment thereof has an Area Under the $Curve_{(0-inf)}$ value that is at least about 100,000 nMol×hour/L. The AUC may be in the range of about 10.0 μg×day/mL to about 5000.0 μg×day/mL. The AUC may be in the range of about 10 nmol×hour/L to about 200,000.0 nmol×hour/L.

The present inventors developed human monoclonal antibodies against SARS-related coronavirus which overcome the disadvantages and shortcomings of known antibodies.

Herein, the inventors describe novel monoclonal antibodies of human origin which are directed against the spike (S) protein of SARS-CoV-2, do not exhibit autoreactivity and exceed the neutralization potency of similar antibodies of the prior art.

Therefore, the inventive antibodies include highly promising candidates for antibody-mediated strategies to effectively treat and/or prevent SARS-related coronavirus infection and disease symptoms caused by such an infection.

Thus, the present invention provides antibodies or antigen-binding fragments thereof directed against SARS-related coronavirus, wherein the antibody or antigen-binding fragment thereof comprises the heavy chain CDR1, CDR2, and CDR3 and the light chain CDR1, CDR2, CDR3 amino acid sequence of one antibody from the group comprising HbnC3t1p1_C6 (with the variable region heavy chain amino acid sequence of SEQ ID No. 1 and the variable region light chain amino acid sequence of SEQ ID No. 2), HbnC3t1p1_G4 (with the variable region heavy chain amino acid sequence of SEQ ID No. 3 and the variable region light chain amino acid sequence of SEQ ID No. 4), HbnC3t1p2_B10 with the variable region heavy chain amino acid sequence of SEQ ID No. 5 and the variable region light chain amino acid sequence of SEQ ID No. 6), MnC2t2p1_C11 (with the variable region heavy chain amino acid sequence of SEQ ID No. 7 and the variable region light chain amino acid sequence of SEQ ID No. 8), FnC1t2p1_D4 (with the variable region heavy chain amino acid sequence of SEQ ID No. 9 and the variable region light chain amino acid sequence of SEQ ID No. 10), FnC1t2p1_G5 (with the variable region heavy chain amino acid sequence of SEQ ID No. 11 and the variable region light chain amino acid sequence of SEQ ID No. 12), HbnC3t1p2_C6 (with the variable region heavy chain amino acid sequence of SEQ ID No. 13 and the variable region light chain amino acid sequence of SEQ ID No. 14), MnC4t2p1_B3 (with the variable region heavy chain amino acid sequence of SEQ ID No. 15 and the variable region light chain amino acid sequence of SEQ ID No. 16), MnC2t1p1_A3 (with the variable region heavy chain amino acid sequence of SEQ ID No. 17 and the variable region light chain amino acid sequence of SEQ ID No. 18), CnC2t1p1_B4 (with the variable region heavy chain amino acid sequence of SEQ ID No. 19 and the variable region light chain amino acid sequence of SEQ ID No. 20), HbnC3t1p1_F4 (with the variable region heavy chain amino acid sequence of SEQ ID No. 21 and the variable region light chain amino acid sequence of SEQ ID No. 22), HbnC2t1p2_D9 (with the variable region heavy chain amino acid sequence of SEQ ID No. 23 and the variable region light chain amino acid sequence of SEQ ID No. 24), MnC5t2p1_G1 (with the variable region heavy chain amino acid sequence of SEQ ID No. 25 and the variable region light chain amino acid sequence of SEQ ID No. 26), CnC2t1p1_E12 (with the variable region heavy chain amino acid sequence of SEQ ID No. 27 and the variable region light chain amino acid sequence of SEQ ID No. 28), CnC2t1p1_D6 (with the variable region heavy chain amino acid sequence of SEQ ID No. 29 and the variable region light chain amino acid sequence of SEQ ID No. 30), MnC2t1p1_C5 (with the variable region heavy chain amino acid sequence of SEQ ID No. 31 and the variable region light chain amino acid sequence of SEQ ID No. 32), CnC2t1p1_E8 (with the variable region heavy chain amino acid sequence of SEQ ID No. 33 and the variable region light chain amino acid sequence of SEQ ID No. 34), MnC1t3p1_G9 (with the variable region heavy chain amino acid sequence of SEQ ID No. 35 and the variable region light chain amino acid sequence of SEQ ID No. 36), HbnC4t1p1_D5 (with the variable region heavy chain amino acid sequence of SEQ ID No. 37 and the variable region light chain amino acid sequence of SEQ ID No. 38), CnC2t1p1_B10 (with the variable region heavy chain amino acid sequence of SEQ ID No. 39 and the variable region light chain amino acid sequence of SEQ ID No. 40), CnC2t1p1_G6 (with the variable region heavy chain amino acid sequence of SEQ ID No. 41 and the variable region light chain amino acid sequence of SEQ ID No. 42), FnC1t1p2_A5 (with the variable region heavy chain amino acid sequence of SEQ ID No. 43 and the variable region light chain amino acid sequence of SEQ ID No. 44), MnC4t2p1_D10 (with the variable region heavy chain amino acid sequence of SEQ ID No. 45 and the variable region light chain amino acid sequence of SEQ ID No. 46), MnC4t2p2_A4 (with the variable region heavy chain amino acid sequence of SEQ ID No. 47 and the variable region light chain amino acid sequence of SEQ ID No. 48), MnC4t1p1_A10 (with the variable region heavy chain amino acid sequence of SEQ ID No. 49 and the variable region light chain amino acid sequence of SEQ ID No. 50), MnC4t2p1_E6 (with the variable region heavy chain amino acid sequence of SEQ ID No. 51 and the variable region light chain amino acid sequence of SEQ ID No. 52), MnC4t1p1_A11 (with the variable region heavy chain amino acid sequence of SEQ ID No. 53 and the variable region light chain amino acid sequence of SEQ ID No. 54), and MnC4t2p1_F5 (with the variable region heavy chain amino acid sequence of SEQ ID No. 55 and the variable region light chain amino acid sequence of SEQ ID No. 56). In an embodiment, the antibody or antigen-binding fragment thereof comprises the heavy chain CDR1, CDR2, and CDR3 and the light chain CDR1, CDR2, and CDR3 amino acid sequence of one of the antibodies selected from the group comprising HbnC3t1p1_C6, HbnC3t1p1_G4, HbnC3t1p2_B10, MnC2t2p1_C11, FnC1t2p1_D4, FnC1t2p1_G5, HbnC3t1p2_C6, MnC4t2p1_B3, MnC2t1p1_A3, CnC2t1p1_B4, HbnC3t1p1_F4, and HbnC2t1p2_D9. In an embodiment, the antibody or antigen-binding fragment thereof comprises the heavy chain CDR1, CDR2, and CDR3 and the light chain CDR1, CDR2, CDR3 amino acid sequence of one of the antibodies selected from the group comprising HbnC3t1p1_C6, HbnC3t1p1_G4, HbnC3t1p2_B10, MnC2t2p1_C11, and FnC1t2p1_D4.

Within the context of the present invention, the antibodies, which have been generated and described herein, may be used and claimed as a complete monoclonal human antibody or as any functional or antigen-binding fragment thereof. In an embodiment, the antibody or any kind of functional or antigen-binding fragment thereof at least comprises the complementarity determining regions (CDR) 1, 2, and 3 of the heavy chain and CDR 1, 2, and 3 of the light chain of the antibody.

The CDR regions of the antibody sequences described herein may be defined according to any numbering scheme known in the art, including, for example, the numbering scheme of IMGT which is an adaptation of the numbering scheme of Chothia (ImMunoGeneTics information System®; Lefranc et al., NAR 27: 209-212 (1999); http://imgt.cines.fr).

Based on the common general knowledge and the information given herein on the variable region heavy chain amino acid sequences and the variable region light chain amino acid sequences of the antibodies of the invention, the CDRs can be easily and unambiguously determined by a skilled person.

According to one embodiment of the present invention, the CDR sequences of the light and heavy chain sequences of the antibodies described herein are as follows:

| Comprised in SEQ ID NO: | Source | CDR1 | SEQ ID of CDR1 | CDR2 | SEQ ID of CDR2 | CDR3 | SEQ ID of CDR3 |
|---|---|---|---|---|---|---|---|
| 1 | Heavy chain of HbnC3t1p1_C6 | GFTFTSSA | 59 | IVVGSGNT | 60 | AAPHCSSTICY DGFDI | 61 |
| 2 | Light chain of HbnC3t1p1_C6 | QSVSSSY | 62 | GAS | 63 | QQYGSSPWT | 64 |
| 3 | Heavy chain of HbnC3t1p1_G4 | GFTVSSNY | 65 | IYSGGST | 66 | ARDFGDFFFDY | 67 |
| 4 | Light chain of HbnC3t1p1_G4 | QSVSSY | 68 | GVS | 69 | QQYGSSPRT | 70 |
| 5 | Heavy chain of HbnC3t1p2_B10 | GFIVSSNY | 71 | IYSGGST | 72 | ARDYGDYFFDY | 73 |
| 6 | Light chain of HbnC3t1p2_B10 | QSVSSY | 74 | GAS | 75 | QQYGSSPRT | 76 |
| 7 | Heavy chain of MnC2t2p1_C11 | GGTFSRYT | 77 | IIPILDIA | 78 | AREGGLDYFGS RNSGWTYTWFD P | 79 |
| 8 | Light chain of MnC2t2p1_C11 | QNISSY | 80 | AAS | 81 | QQSYSTLYS | 82 |
| 9 | Heavy chain of FnC1t2p1_D4 | GYTFLRFA | 83 | IDTNTGTP | 84 | ARSLRGANLVP | 85 |
| 10 | Light chain of FnC1t2p1_D4 | QDVSNY | 86 | DAF | 87 | QQYDNLPLT | 88 |
| 11 | Heavy chain of FnC1t2p1_G5 | GYTFLRFA | 89 | IDTNTGTP | 90 | ARSLRGANLVP | 91 |
| 12 | Light chain of FnC1t2p1_G5 | QDVSNY | 92 | DAF | 93 | QQYDNLPLT | 94 |
| 13 | Heavy chain of HbnC3t1p2_C6 | GFTFSSSA | 95 | IVVGSGNT | 96 | AAPYCSSTRCY DAFDI | 97 |

-continued

| Comprised in SEQ ID NO: | Source | CDR1 | SEQ ID of CDR1 | CDR2 | SEQ ID of CDR2 | CDR3 | SEQ ID of CDR3 |
|---|---|---|---|---|---|---|---|
| 14 | Light chain of HbnC3t1p2_C6 | QSVSSSY | 98 | GAS | 99 | QQYGRSPWT | 100 |
| 15 | Heavy chain of MnC4t2p1_B3 | GFTFDDYA | 101 | ISWNGGIL | 102 | AKDLRRQDYYA DWYFDL | 103 |
| 16 | Light chain of MnC4t2p1_B3 | QGISSW | 104 | AAS | 105 | QQGNSFPFT | 106 |
| 17 | Heavy chain of MnC2t1p1_A3 | GFTVSSNY | 107 | IYSGGST | 108 | ATGARFGESPF DY | 109 |
| 18 | Light chain of MnC2t1p1_A3 | QGISSW | 110 | AAS | 111 | QQANSFPGT | 112 |
| 19 | Heavy chain of CnC2t1p1_B4 | GYTFTSYG | 113 | ISAYNGNT | 114 | ARDGELLGWFD P | 115 |
| 20 | Light chain of CnC2t1p1_B4 | SSDVGSYN L | 116 | EGS | 117 | CSYAGSSTWV | 118 |
| 21 | Heavy chain of HbnC3t1p1_F4 | GFTFRRYG | 119 | ILFDGSNK | 120 | AKGGDYEWELL ES | 121 |
| 22 | Light chain of HbnC3t1p1_F4 | QSIDNW | 122 | KAS | 123 | QHYHSFPLT | 124 |
| 23 | Heavy chain of HbnC2t1p2_D9 | GFTFSSYG | 125 | IWYDGRNK | 126 | ARAARRPVVTD TMAYYMDV | 127 |
| 24 | Light chain of HbnC2t1p2_D9 | LSLSSY | 128 | DAS | 129 | QQRSNWPPTWT | 130 |
| 25 | Heavy chain of MnC5t2p1_G1 | GFTFTSSA | 131 | IVVGSGNT | 132 | AAPRCSGGSCY DGFDI | 133 |
| 26 | Light chain of MnC5t2p1_G1 | QSVSSSY | 134 | GAS | 135 | QQYGSSPWT | 136 |
| 27 | Heavy chain of CnC2t1p1_E12 | GFTFGDYA | 137 | IRSKAYGG TT | 138 | TRVRRLWFGSY YYGMDV | 139 |
| 28 | Light chain of CnC2t1p1_E12 | QSLLHSNG YNY | 140 | LGS | 141 | MQALQTPGT | 142 |
| 29 | Heavy chain of CnC2t1p1_D6 | GFTFGDYA | 143 | IRSKAYGG TT | 144 | TRVRRLWFGSY YYGMDV | 145 |
| 30 | Light chain of CnC2t1p1_D6 | QSLLHSNG YNY | 146 | LGS | 147 | MQALQTPGT | 148 |
| 31 | Heavy chain of MnC2t1p1_C5 | GFTVSSNY | 149 | IYSGGST | 150 | ATGARFGESPF DY | 151 |
| 32 | Light chain of MnC2t1p1_C5 | QGISSW | 152 | AAS | 153 | QQANSFPGT | 154 |
| 33 | Heavy chain of CnC2t1p1_E8 | GYIFTNYY | 155 | IHSLSGGT | 156 | ARASVSTITDF DY | 157 |
| 34 | Light chain of CnC2t1p1_E8 | SGDVGSYN L | 158 | EAT | 159 | CSYAGVRTVV | 160 |
| 35 | Heavy chain of MnC1t3p1_G9 | GFTFRNYA | 161 | ISDSGDRT | 162 | ALASGSYFGGA NY | 163 |
| 36 | Light chain of MnC1t3p1_G9 | TGPVTSDH Y | 164 | DTN | 165 | LLSYTGARV | 166 |
| 37 | Heavy chain of HbnC4t1p1_D5 | GFTFDDYA | 167 | ISWNSGSI | 168 | AKDINYDSGGY HKNYFDY | 169 |
| 38 | Light chain of HbnC4t1p1_D5 | QSISSY | 170 | AAS | 171 | QQSYSNPLT | 172 |

-continued

| Comprised in SEQ ID NO: | Source | CDR1 | SEQ ID of CDR1 | CDR2 | SEQ ID of CDR2 | CDR3 | SEQ ID of CDR3 |
|---|---|---|---|---|---|---|---|
| 39 | Heavy chain of CnC2t1p1_1310 | GGTFSSYA | 173 | IIPIFGTA | 174 | ARVSGYDSSGY WGDY | 175 |
| 40 | Light chain of CnC2t1p1_1310 | QSVSSY | 176 | DAS | 177 | QQRSNWPPALT | 178 |
| 41 | Heavy chain of CnC2t1p1_G6 | GYIFTNYY | 179 | IHSLSGGT | 180 | ARASVATITDF DY | 181 |
| 42 | Light chain of CnC2t1p1_G6 | SGDIGSYN L | 182 | EAS | 183 | CSYAGVRIVV | 184 |
| 43 | Heavy chain of FnC1t1p2_A5 | GYTFTSYD | 185 | MNPNSGNT | 186 | ARATTDCSSTS CWSLDFWSGYY TGGREKIFDY | 187 |
| 44 | Light chain of FnC1t1p2_A5 | QSVSSSY | 188 | GAS | 189 | QQYGSSPGT | 190 |
| 45 | Heavy chain of MnC4t2p1_D10 | GASISSNH YF | 191 | MHYSGST | 192 | ARGVNYYDRNG YYRNDGFDI | 193 |
| 46 | Light chain of MnC4t2p1_D10 | QGIRND | 194 | AAS | 195 | LQHNTYPFT | 196 |
| 47 | Heavy chain of MnC4t2p2_A4 | GYIFINYA | 197 | INTNTGNP | 198 | AKIGSRNSLGV | 199 |
| 48 | Light chain of MnC4t2p2_A4 | HSVDRSY | 200 | GAS | 201 | QHFGTSSVT | 202 |
| 49 | Heavy chain of MnC4t1p1_A10 | GASISSNH YF | 203 | MHYSGST | 204 | ARGVNYYDRNG YYRNDGFDI | 205 |
| 50 | Light chain of MnC4t1p1_A10 | QGIRND | 206 | AAS | 207 | LQHNTYPFT | 208 |
| 51 | Heavy chain of MnC4t2p1_E6 | GFTFDDYA | 209 | ISWNGGIL | 210 | AKDLRRQDYYA DWYFDL | 211 |
| 52 | Light chain of MnC4t2p1_E6 | QGISSW | 212 | AAS | 213 | QQGNSFPFT | 214 |
| 53 | Heavy chain of MnC4t1p1_A11 | GFTFSSYS | 215 | ISSSSNTR | 216 | ASSKGFCSGGS CSDY | 217 |
| 54 | Light chain of MnC4t1p1_A11 | QSVSSSY | 218 | GVS | 219 | HQYGSSPWT | 220 |
| 55 | Heavy chain of MnC4t2p1_F5 | GASISSNH YF | 221 | MHYSGST | 222 | ARGVNYYDRNG YYRNDGFDI | 223 |
| 56 | Light chain of MnC4t2p1_F5 | QGIRND | 224 | AAS | 225 | LQHNTYPFT | 226 |

The present invention further comprises a derivative of antibody CnC2t1p1_B4 as described herein. In an embodiment, the antibody or antigen-binding fragment thereof is a derivative of an antibody (e.g., CnC2t1p1_B4) having the variable region heavy chain amino acid sequence of SEQ ID NO: 19 and the variable region light chain amino acid sequence of SEQ ID NO: 20, and thus the heavy chain CDR1, CDR2, and CDR3 amino acid sequences of SEQ ID NOs: 113, 114, and 115, respectively, and the light chain CDR1, CDR2, and CDR3 amino acid sequences of SEQ ID NOs: 116, 117, and 118, respectively, wherein the derivative has a heavy chain CDR2 amino acid sequence of SEQ ID NO: 227 and/or the derivative has a light chain CDR3 amino acid sequence of SEQ ID NO: 228.

According to one particularly embodiment of the present invention, the antibody has a heavy chain amino acid sequence of SEQ ID No. 229 and a light chain amino acid sequence of SEQ ID No. 230. This antibody is a variant of HbnC3t1p1_F4, wherein the terminal lysine of the heavy chain constant domain has been removed (referenced herein as DZIF-10c, alternatively referenced as HbnC3t1p1_F4(-K)). In a different embodiment of the present invention, the terminal lysine of the heavy chain constant region of the antibody HbnC3t1p1_F4(-K) is still present.

In various embodiments, the antibody is an antibody as described herein, wherein the terminal lysine of the heavy chain constant domain (e.g., a C-terminal lysine) has been removed and/or the heavy chain of the antibody lacks a terminal lysine (e.g., a C-terminal lysine).

According to one embodiment, the present invention also provides antibodies or antigen-binding fragments thereof, wherein the antibody or antigen-binding fragment thereof comprises the combination of the variable region heavy chain sequence and of the variable region light chain sequence of one antibody selected from the group comprising HbnC3t1p1_C6 (with the variable region heavy chain amino acid sequence of SEQ ID No. 1 and the variable region light chain amino acid sequence of SEQ ID No. 2), HbnC3t1p1_G4 (with the variable region heavy chain amino acid sequence of SEQ ID No. 3 and the variable region light chain amino acid sequence of SEQ ID No. 4), HbnC3t1p2_B10 with the variable region heavy chain amino acid sequence of SEQ ID No. 5 and the variable region light chain amino acid sequence of SEQ ID No. 6), MnC2t2p1_C11 (with the variable region heavy chain amino acid sequence of SEQ ID No. 7 and the variable region light chain amino acid sequence of SEQ ID No. 8), FnC1t2p1_D4 (with the variable region heavy chain amino acid sequence of SEQ ID No. 9 and the variable region light chain amino acid sequence of SEQ ID No. 10), FnC1t2p1_G5 (with the variable region heavy chain amino acid sequence of SEQ ID No. 11 and the variable region light chain amino acid sequence of SEQ ID No. 12), HbnC3t1p2_C6 (with the variable region heavy chain amino acid sequence of SEQ ID No. 13 and the variable region light chain amino acid sequence of SEQ ID No. 14), MnC4t2p1_B3 (with the variable region heavy chain amino acid sequence of SEQ ID No. 15 and the variable region light chain amino acid sequence of SEQ ID No. 16), MnC2t1p1_A3 (with the variable region heavy chain amino acid sequence of SEQ ID No. 17 and the variable region light chain amino acid sequence of SEQ ID No. 18), CnC2t1p1_B4 (with the variable region heavy chain amino acid sequence of SEQ ID No. 19 and the variable region light chain amino acid sequence of SEQ ID No. 20), HbnC3t1p1_F4 (with the variable region heavy chain amino acid sequence of SEQ ID No. 21 and the variable region light chain amino acid sequence of SEQ ID No. 22), HbnC2t1p2_D9 (with the variable region heavy chain amino acid sequence of SEQ ID No. 23 and the variable region light chain amino acid sequence of SEQ ID No. 24), MnC5t2p1_G1 (with the variable region heavy chain amino acid sequence of SEQ ID No. 25 and the variable region light chain amino acid sequence of SEQ ID No. 26), CnC2t1p1_E12 (with the variable region heavy chain amino acid sequence of SEQ ID No. 27 and the variable region light chain amino acid sequence of SEQ ID No. 28), CnC2t1p1_D6 (with the variable region heavy chain amino acid sequence of SEQ ID No. 29 and the variable region light chain amino acid sequence of SEQ ID No. 30), MnC2t1p1_C5 (with the variable region heavy chain amino acid sequence of SEQ ID No. 31 and the variable region light chain amino acid sequence of SEQ ID No. 32), CnC2t1p1_E8 (with the variable region heavy chain amino acid sequence of SEQ ID No. 33 and the variable region light chain amino acid sequence of SEQ ID No. 34), MnC1t3p1_G9 (with the variable region heavy chain amino acid sequence of SEQ ID No. 35 and the variable region light chain amino acid sequence of SEQ ID No. 36), HbnC4t1p1_D5 (with the variable region heavy chain amino acid sequence of SEQ ID No. 37 and the variable region light chain amino acid sequence of SEQ ID No. 38), CnC2t1p1_B10 (with the variable region heavy chain amino acid sequence of SEQ ID No. 39 and the variable region light chain amino acid sequence of SEQ ID No. 40), CnC2t1p1_G6 (with the variable region heavy chain amino acid sequence of SEQ ID No. 41 and the variable region light chain amino acid sequence of SEQ ID No. 42), FnC1t1p2_A5 (with the variable region heavy chain amino acid sequence of SEQ ID No. 43 and the variable region light chain amino acid sequence of SEQ ID No. 44), MnC4t2p1_D10 (with the variable region heavy chain amino acid sequence of SEQ ID No. 45 and the variable region light chain amino acid sequence of SEQ ID No. 46), MnC4t2p2_A4 (with the variable region heavy chain amino acid sequence of SEQ ID No. 47 and the variable region light chain amino acid sequence of SEQ ID No. 48), MnC4t1p1_A10 (with the variable region heavy chain amino acid sequence of SEQ ID No. 49 and the variable region light chain amino acid sequence of SEQ ID No. 50), MnC4t2p1_E6 (with the variable region heavy chain amino acid sequence of SEQ ID No. 51 and the variable region light chain amino acid sequence of SEQ ID No. 52), MnC4t1p1_A11 (with the variable region heavy chain amino acid sequence of SEQ ID No. 53 and the variable region light chain amino acid sequence of SEQ ID No. 54), and MnC4t2p1_F5 (with the variable region heavy chain amino acid sequence of SEQ ID No. 55 and the variable region light chain amino acid sequence of SEQ ID No. 56). In an embodiment, the antibody or antigen-binding fragment thereof comprises the variable region heavy chain sequence and of the variable region light chain sequence of one antibody selected from the group comprising HbnC3t1p1_C6, HbnC3t1p1_G4, HbnC3t1p2_B10, MnC2t2p1_C11, FnC1t2p1_D4, FnC1t2p1_G5, HbnC3t1p2_C6, MnC4t2p1_B3, MnC2t1p1_A3, CnC2t1p1_B4, HbnC3t1p1_F4, and HbnC2t1p2_D9. In an embodiment, the antibody or antigen-binding fragment thereof comprises the variable region heavy chain sequence and of the variable region light chain sequence of one antibody selected from the group comprising HbnC3t1p1_C6, HbnC3t1p1_G4, HbnC3t1p2_B10, MnC2t2p1_C11, and FnC1t2p1_D4.

In general, the antibodies or antigen-binding fragments thereof as described herein further encompass antibody amino acid sequences being at least 80% identical to the sequences as defined above as long as they are still directed against the spike (S) protein of SARS-CoV-2 as in SEQ ID NO. 57 (e.g., as long as they are still directed against the receptor-binding domain (RBD) of the spike (S) protein of SARS-CoV-2 as in SEQ ID NO. 58).

This is meant to include sequences having conservative mutations of the antibody amino acid sequence which do not interfere with structural folds and the affinity of the antibody to the spike (S) protein. For example, the deviations in the amino acid sequence leading to an at least 80%, 85%, 90% or 95% overall identity to the individualized sequences explicitly disclosed herein are present exclusively outside the CDR regions of the antibodies according to the invention. In particular, the present invention encompasses antibody amino acid sequences having 1, 2, 3, 4, or 5 mutations within the constant regions of the antibody. In some embodiments, the present invention encompasses antibody amino acid sequences having 1, 2, 3, 4, or 5 mutations within one or more framework regions of the antibody.

In some embodiments, the present invention includes an antibody directed against the spike (S) protein of SARS-CoV-2, the antibody having a heavy chain and a light chain, wherein the heavy chain amino acid sequence and the light chain amino acid sequence are independently at least 95%, at least 98%, or at least 99% identical to the amino acid sequence of SEQ ID NO: 229 and/or 230, provided that the antibody retains binding to the spike (S) protein of SARS-CoV-2.

In some embodiments, the antibody or antigen-binding fragment thereof directed against the spike (S) protein of SARS-CoV-2 comprises a heavy chain variable region sequence that comprises an amino acid sequence with at least about 95%, at least about 96%, at least about 97%, at least about 98%, or at least about 99% sequence identity to the amino acid sequence set forth in SEQ ID NO: 229, provided that the antibody retains binding to the spike (S) protein of SARS-CoV-2. In some embodiments, the antibodies comprise the heavy chain variable region sequence of SEQ ID NO: 229, and have one or more conservative amino acid substitutions, e.g., 1, 2, 3, 4, or 5 conservative amino acid substitutions in the heavy chain variable region sequence. In further embodiments, the conservative amino acid substitutions fall within one or more framework regions in SEQ ID NO: 229.

In some embodiments, the antibody or antigen-binding fragment thereof directed against the spike (S) protein of SARS-CoV-2 comprises a light chain variable region sequence that comprises an amino acid sequence with at least about 95%, at least about 96%, at least about 97%, at least about 98%, or at least about 99% sequence identity to the amino acid sequence set forth in SEQ ID NO: 230, provided that the antibody retains binding to the spike (S) protein of SARS-CoV-2. In some embodiments, the antibodies comprise the light chain variable region sequence of SEQ ID NO: 230, and have one or more conservative amino acid substitutions, e.g., 1, 2, 3, 4, or 5 conservative amino acid substitutions in the light chain variable region sequence. In further embodiments, the conservative amino acid substitutions fall within one or more framework regions in SEQ ID NO: 230.

The antibodies according to the present invention may be of human origin. Thus, at least the sequences outside the CDRs, such as framework and constant regions of the antibody, may be of human origin or can be attributed to human origin. Furthermore, the antibodies of the present invention may be monoclonal antibodies.

In one embodiment, the antibody is a monoclonal antibody or a fragment thereof that retains binding specificity and ability to neutralize infectious pathogen. In one embodiment, the antibody is an IgG1, IgG2, IgG3, or IgG4 antibody. For example, the antibody may be an antibody comprising an Fc domain of any human IgG isotype (e.g. IgG1, IgG2, IgG3, or IgG4).

Optionally, the antigen-binding compound consists of or comprises a Fab, Fab', Fab'-SH, $F(ab)_2$, Fv, a diabody, single-chain antibody fragment, or a multispecific antibody comprising multiple different antibody fragments.

Within the present invention, an antibody or antigen-binding fragment thereof directed against the spike (S) protein of SARS-CoV-2 means an antibody or antigen-binding fragment thereof binding to the spike (S) protein of SARS-CoV-2 with an at least 10-fold, including, at least 50-fold, or at least 100-fold increased affinity compared to unrelated epitopes, proteins or protein regions.

One skilled in the art could determine if an antibody which exhibits a certain degree of identity is directed against the spike (S) protein of SARS-CoV-2 based on the above or the common general knowledge.

The determination of percent identity between two sequences is accomplished according to the present invention by using the mathematical algorithm of Karlin and Altschul (Proc. Natl. Acad. Sci. USA (1993) 90: 5873-5877). Such an algorithm is the basis of the BLASTN and BLASTP programs of Altschul et al. (J. Mol. Biol. (1990) 215: 403-410). BLAST nucleotide searches are performed with the BLASTN program. To obtain gapped alignments for comparative purposes, Gapped BLAST is utilized as described by Altschul et al. (Nucleic Acids Res. (1997) 25: 3389-3402). When utilizing BLAST and Gapped BLAST programs, the default parameters of the respective programs are used.

According to another embodiment of the present invention, are nucleic acid sequences which encode the antibody amino acid sequences being at least 85%, 90%, 95%, 99%, or 100% identical to the sequences defined above and disclosed herein.

According to an embodiment of the present invention, the SARS-related coronavirus strain is severe acute respiratory syndrome coronavirus 2 (SARS-CoV-2) which may alternatively be referred to as SARS-related coronavirus 2 in the art. According to another embodiment of the present invention, the SARS-related coronavirus strain is severe acute respiratory syndrome coronavirus (SARS-CoV or SARS-CoV-1)

According to another embodiment of the invention, the antibody or antigen-binding fragment thereof is directed against the ectodomain of the spike (S) protein of SARS-CoV-2.

According to a more embodiment of the present invention, the antibody or antigen-binding fragment thereof is directed against the ectodomain of the spike (S) homotrimer of SARS-CoV-2 in the prefusion-stabilized-variant of the virus isolate Wuhan-Hu-1 as described in Wrapp et al., Science (2020) doi: 10.1126/science.abb2507 (SEQ ID NO. 57). This virus isolate has been studied intensively and is best understood at the time of filing.

The antibody or antigen-binding fragment thereof may also be directed against equivalent sequences of other virus variants. According to one specific embodiment, the antibody or antigen-binding fragment thereof is directed against the receptor-binding domain (RBD) of the spike (S) protein of SARS-CoV-2 (SEQ ID NO. 58).

According to one embodiment of the present invention, the antibody or antigen-binding fragment thereof is directed against a sequence of the ectodomain of the spike (S) homotrimer of SARS-CoV-2 in the prefusion-stabilized-variant of the virus isolate Wuhan-Hu-1 as described in Wrapp et al., Science (2020) doi: 10.1126/science.abb2507 (SEQ ID NO. 57) outside the receptor-binding domain (RBD) of the spike (S) protein of SARS-CoV-2 (SEQ ID NO. 58).

According to one embodiment of the present invention, the antibody or antigen-binding fragment thereof exhibits a neutralization potency of the authentic SARS-CoV-2 isolate BavPat1/2020 on VeroE6 cells (IC100; lowest antibody dose leading to the complete absence of cytopathic effects) of less than 10 μg/ml when tested in a virus neutralization test using 100 TCID50 of SARS-CoV-2 applied to VeroE6 cells following a 1 hour co-incubation of virus and antibody at 37° C. according to Koch et al., Lancet Infect. Dis. (2020) doi:10.1016/s1473-3099(20)30248-6.

In one aspect, the neutralization potency defined above is tested by following the protocol of the "Virus neutralization test" disclosed in the Examples section. According to a embodiment of the invention, the antibody or antigen-binding fragment thereof exhibits a neutralization potency of less than 1 μg/ml, less than 0.5 μg/ml, less than 0.25 μg/ml, or less than 0.12 μg/ml.

According to one embodiment of the present invention, the antibody or antigen-binding fragment thereof exhibits a binding constant ($K_D$) to the RBD of SEQ ID NO: 58 as determined by surface plasmon resonance of 20 nM or less, 5 nM or less, 1 nM or less, 0.2 nM or less, or 0.1 nM or less.

According to an embodiment of the present invention, the antibody or antigen-binding fragment thereof does not display autoreactivity against human cells defined as detectable binding when tested against permeabilized HEp-2 cells using an antinuclear antibody (ANA) testing kit (NOVA-Lite HEp-2 ANA kit; Inova Diagnostics) at concentrations of 100 μg/ml of the antibody or antigen-binding fragment thereof. Alternatively, other assays known in the art may be used to determine or exclude autoreactivity of antibodies or antigen-binding fragments thereof.

In the description of the present application, antibody designations may be used. It is pointed out that the antibodies consist of heavy and light chains which also form part of the present description. If reference is made to an antibody by its designation or to a SEQ ID No., it should be understood that these ways of reference are interchangeable.

The present invention further relates to a pharmaceutical composition comprising an antibody or antigen-binding fragment thereof according to the invention and at least one pharmaceutically acceptable excipient. In one aspect, the pharmaceutical composition is a vaccination composition for a human and/or animal subject. The present invention also encompasses a kit comprising an antibody or antigen-binding fragment thereof according to the invention as defined and further described herein and a container.

In one aspect, the present invention is also directed to the antibody or antigen-binding fragment as described herein, the pharmaceutical composition as described herein, and the kit as described herein for use as a medicament (e.g., for use as a vaccine composition).

In another aspect, the present invention is also directed to the antibody or antigen-binding fragment thereof as described herein, the pharmaceutical composition as described herein, and the kit as described herein for use in the treatment or prevention of a disease caused by SARS-related coronavirus in human or animal subjects (e.g., for use in the treatment or prevention of a disease caused by SARS-related coronavirus 2 (SARS-CoV-2) in human or animal subjects).

In one aspect, the present invention is directed to the antibody or antigen-binding fragment thereof as described herein, the pharmaceutical composition as described herein, and the kit as described herein for use in prevention of infection of a human and/or animal subject with SARS-related coronavirus (e.g., an infection of a human and/or animal subject with SARS-related coronavirus 2 (SARS-CoV-2)).

In another aspect of the invention, an antibody or antigen-binding fragment thereof according to the invention is administered to a patient in need thereof by intravenous injection or infusion. In a embodiment, the antibody or antigen-binding fragment thereof is administered by intravenous infusion at a dose of about 1 mg/kg body weight to about 100 mg/kg body weight of the patient. In an embodiment, the antibody or antigen-binding fragment thereof is administered at a dose of about 2.5 mg/kg, about 5 mg/kg, about 10 mg/kg, about 20 mg/kg, about 25 mg/kg, about 30 mg/kg, about 40 mg/kg, about 50 mg/kg, or about 100 mg/kg. In an embodiment, the antibody or antigen-binding fragment thereof is administered at a dose of about 2.5 mg/kg to about 5 mg/kg, about 5 mg/kg to about 10 mg/kg, about 10 mg/kg to about 20 mg/kg, about 20 mg/kg to about 25 mg/kg, about 25 mg/kg to about 30 mg/kg, about 30 mg/kg to about 40 mg/kg, about 40 mg/kg to about 50 mg/kg, about 50 mg/kg to about 100 mg/kg, about 50 mg/kg to about 60 mg/kg, about 60 mg/kg to about 70 mg/kg, about 70 mg/kg to about 80 mg/kg, about 80 mg/kg to about 90 mg/kg, and/or about 90 mg/kg to about 100 mg/kg. The dosage of an antibody or antigen-binding fragment thereof to be administered to a subject can further vary depending on such things as the severity of the symptoms exhibited as well as the age, sex, and health of the subject.

In another aspect of the invention, an antibody or antigen-binding fragment thereof according to the invention is administered to a patient in need thereof by inhalative application. In an embodiment, the antibody or antigen-binding fragment thereof is administered by inhalative application, wherein it is provided in a liquid pharmaceutical composition which is nebulized by a mesh nebulizer or a jet nebulizer prior to administration. In an embodiment, the antibody or antigen-binding fragment thereof is administered by inhalative application at a dose of about 50 mg, about 100 mg, about 200 mg, about 250 mg, about 300 mg, about 400 mg, about 500 mg, about 750 mg, or about 1000 mg. In an embodiment, the antibody or antigen-binding fragment thereof is administered by inhalative application at a dose of about 50 mg to about 100 mg, about 100 mg to about 200 mg, about 200 mg to about 250 mg, about 250 mg to about 300 mg, about 300 mg to about 400 mg, about 400 mg to about 500 mg, about 500 mg to about 750 mg, and/or about 750 mg to about 1000 mg. In another embodiment, the antibody or antigen-binding fragment thereof is administered by inhalative application, followed by a second dose which is administered by intravenous injection or infusion.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation and inhaled through the mouth), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

The methods of the invention may comprise pulmonary administration, e.g., by use of an inhaler or nebulizer, of a composition formulated with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entireties. In a specific embodiment, an antibody or antigen-binding fragment thereof of the invention, combination therapy, and/or composition of the invention is administered using Alkermes AIR® pulmonary drug delivery technology (Alkermes, Inc., Cambridge, Mass., U.S.A.). In another specific embodiment, an antibody or antigen-binding fragment thereof of the invention, combination therapy, and/or composition of the invention is administered using Aerogen Solo® pulmonary drug delivery technology (Aerogen GmbH, Ratingen, Germany).

The methods of the invention may also comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The pharmaceutical formulation of the present invention may be provided in liquid form or may be provided in lyophilized form.

The pharmaceutical formulation according to the present invention may comprise a buffering agent. Buffering agents include, but are not limited to citric acid, HEPES, histidine, potassium acetate, potassium citrate, potassium phosphate ($KH_2PO_4$), sodium acetate, sodium bicarbonate, sodium citrate, sodium phosphate ($NAH_2PO_4$). Tris base, and Tris-HCl. In one embodiment, the buffering agent is histidine. In certain embodiments, the histidine concentration is about 5, 10, 15, 20, 25, 30, 35, 40, 45, 50, 55, 60, 65, 70, 75, 80, 85, 90, 95, or 100 mM. In one embodiment the histidine concentration is 10±5 mM. In one embodiment, the histidine concentration is 10±2 mM. In one embodiment, the histidine concentration is about 10 mM. In one embodiment, the histidine concentration is about 15 mM.

As used herein the term "buffering agent providing a pH of about 5.0 to about 7.0" refers to an agent which provides that the solution comprising it resists changes in pH by the action of its acid/base conjugate components. The buffer used in the formulations in accordance with the present invention may have a pH in the range from about 5.5 to about 7.5, or from about 5.8 to about 7.0. In one embodiment the pH is about 6.0. In one embodiment the pH is about 7.0. Examples of buffering agents that will control the pH in this range include acetate, succinate, gluconate, histidine, citrate, glycylglycine and other organic acid buffers. In one embodiment the buffer is acetate. In one embodiment the acetate is between about 10 mM and 50 mM. In one embodiment the acetate is about 20 mM.

The pharmaceutical formulation according to the present invention may comprises a tonicity agent. Tonicity agents, include, but are not limited to dextrose, glycerin, mannitol, potassium chloride, and sodium chloride. In one embodiment the tonicity agent is sodium chloride. In one embodiment the sodium chloride concentration is about 70 to 170 mM; about 90-150 mM; or about 115±10 mM. In certain embodiments the sodium chloride concentration is about 70, 75, 80, 85, 90, 95, 100, 105, 110, 115, 120, 125, 130, 135, 140, 145, 150, 155, 160, 165, 170, or 175 mM. In one embodiment, the sodium chloride concentration is about 115 mM. In another embodiment, the sodium chloride concentration is 150±10 mM. In one embodiment, the sodium chloride concentration is about 150 mM.

By "isotonic" is meant that the formulation has essentially the same osmotic pressure as human blood. Isotonic formulations will generally have an osmotic pressure from about 250 to 350 mOsm. Isotonicity can be measured using a vapor pressure or freezing-point depression type osmometer.

As used herein a "saccharide" means a stabilizing sugar that is pharmaceutically acceptable for injection. Suitably, disaccharides include sucrose, lactulose, lactose, maltose, trehalose, raffinose, or cellobiose, and/or mixtures thereof. Other contemplated disaccharides include kojibiose, nigerose, isomaltose, ββ-trehalose, αβ-trehalose, sophorose, laminaribiose, gentiobiose, turanose, maltulose, palatinose, gentiobiulose, mannobiose, melibiose, melibiulose, rutinose, rutinulose, and xylobiose. A saccharide includes, but is not limited to, a disaccharide, monosaccharide or polysaccharide. The term "sugar" can be used to refer to all saccharides. A disaccharide can be, for example, sucrose or trehalose, or a mixture thereof. Suitably, a saccharide or a sugar can also serve as a stabilizer agent in the liquid compositions of the present invention. In some aspects of the present invention, the trehalose is trehalose dihydrate.

In certain embodiments, the pharmaceutical formulation according to the present invention comprises a stabilizer. Stabilizers, include, but are not limited to human serum albumin (hsa), bovine serum albumin (bsa), α-casein, globulins, α-lactalbumin, LDH, lysozyme, myoglobin, ovalbumin, and RNase A. Stabilizers also include amino acids and their metabolites, such as, glycine, alanine (α-alanine, β-alanine), arginine, betaine, leucine, lysine, glutamic acid, aspartic acid, proline, 4-hydroxyproline, sarcosine, γ-aminobutyric acid (GABA), opines (alanopine, octopine, strombine), and trimethylamine N-oxide (TMAO). In one embodiment the stabilizer is an amino acid.

In certain embodiments, the pharmaceutical formulation according to the present invention comprises a nonionic surfactant. Nonionic surfactants, include, but are not limited to, polyoxyethylensorbitan fatty acid esters (such as polysorbate 20 and polysorbate 80), polyethylene-polypropylene copolymers, polyethylene-polypropylene glycols, polyoxyethylene-stearates, polyoxyethylene alkyl ethers, e.g. polyoxyethylene monolauryl ether, alkylphenylpolyoxyethylene ethers (TRITON-X), polyoxyethylene-polyoxypropylene copolymer (Poloxamer, Pluronic), sodium dodecyl sulphate (SDS). In one embodiment the nonionic surfactant is polysorbate 80. In one embodiment the polysorbate 80 concentration is about 0.005 to 0.02% (w/v). In one embodiment, the polysorbate 80 concentration is about 0.01% (w/v). In one embodiment, the polysorbate 80 concentration is about 0.02% (w/v). In one embodiment the nonionic surfactant is polysorbate 20. In one embodiment the polysorbate 20 concentration is about 0.005 to 0.05% (w/v). In one embodiment, the polysorbate 20 concentration is about 0.04% (w/v).

In certain embodiments, the pharmaceutical formulation according to the present invention comprises a metal chelator. Metal chelators, include, but are not limited to EDTA and EGTA. In one embodiment the metal chelator is EDTA. In one embodiment the EDTA concentration is about 0.01 to about 0.02 mM. In one embodiment, the EDTA concentration is about 0.05 mM.

In one other aspect, the present invention is also directed to a method of treatment of a patient suffering from a disease caused by SARS-related coronavirus in human or animal subjects (e.g., for use in the treatment or prevention of COVID-19 in human or animal subjects), wherein the patient is administered an effective amount of the antibody or antigen-binding fragment thereof according to the invention or a pharmaceutical composition of the invention.

In another aspect, the present invention is also directed to the use of the antibody or antigen-binding fragment thereof according to the invention or a pharmaceutical composition of the invention in the manufacture of a medicament for treatment of a disease caused by SARS-related coronavirus in human or animal subjects (e.g., for treatment or prevention of COVID-19 in human or animal subjects).

All embodiments of the present invention as described herein are deemed to be combinable in any combination, unless the skilled person considers such a combination to not make any technical sense.

Examples

Example 1: SARS-CoV-2 Infected Individuals and Sample Collection

Samples were obtained under a study protocol approved by the Institutional Review Board of the University of Cologne and all participants provided written informed consent and were recruited at hospitals or as outpatients.

Example 2: Isolation of Peripheral Blood Mononuclear Cells (PBMCs), Plasma and Total IgG from Whole Blood Blood draws were performed using EDTA tubes and/or syringes pre-filled with heparin. PBMC isolation was performed immediately upon arrival using Leucosep centrifuge tubes (Greiner Bio-one) prefilled with density gradient separation medium (Histopaque; Sigma-Aldrich) according to manufacturer's instructions. Plasma was collected and stored separately.

For IgG isolation, 1 ml of the collected plasma was heat-inactivated (56° C. for 40 min) and incubated with Protein G Sepharose (GE Life Sciences) overnight at 4° C. The suspension was transferred to chromatography columns and washed with PBS. IgGs were eluted from Protein G using 0.1 M glycine (pH=3.0) and buffered in 1 M Tris (pH=8.0). For buffer exchange to PBS, 30 kDa Amicon spin membranes (Millipore) were used. Purified IgG concentration was measured with Nanodrop (A280) and samples were stored at 4° C.

Example 3: SARS-CoV-2 S Protein Expression and Purification

The construct encoding the prefusion stabilized SARS-CoV-2 S ectodomain (aminoacids 1-1208 of SARS-CoV-2 S; GenBank: MN908947) was kindly provided by Jason McLellan (Texas, USA) and described previously (Wrapp, D. et al. Cryo-EM structure of the 2019-nCoV spike in the prefusion conformation. *Science* 367, 1260-1263 (2020)).

In detail, two proline substitutions at residues 986 and 987 were introduced for prefusion state stabilization, a "GSAS" substitution at residues 682-685 to eliminate the furin cleavage site and a C-terminal T4 fibritin trimerization motif. For purification, the protein is C-terminally fused to a Twin-StrepTag and 8×HisTag. Protein production was done in HEK293-6E cells by transient transfection with polyethylenimine (PEI, Sigma-Aldrich) and 1 μg DNA per 1 mL cell culture medium at a cell density of 0.8 $10^6$ cells/mL in FreeStyle 293 medium (Thermo Fisher Scientific). After 7 days of culture at 37° C. and 5% $CO_2$ supernatant was harvested and filtered by a 0.45 μm polyethersulfone (PES) Filter (Thermo Fisher Scientific).

Recombinant protein was purified by Strep-Tactin affinity chromatography (IBA lifescience, Gottingen Germany) according to the Strep-Tactin XT manual. Briefly, filtered medium was adjusted to pH8 by adding 100 mL 10× Buffer W (1 M Tris/HCl, pH 8.0, 1.5 M NaCl, 10 mM EDTA, IBA lifescience) and loaded with a low pressure pump at 1 mL/min on 5 mL bedvolume Strep-Tactin resin. The column was washed with 15 column volumes (CV) 1× Buffer W (IBA lifescience) and eluted with 6×2.5 mL 1× Buffer BXT (IBA lifescience). Elution fractions were pooled and buffer was exchanged to PBS pH7.4 (Thermo Fisher Scientific) by filtrating 4 times over 100 kDa cutoff Cellulose centrifugal filter (Merck).

Example 4: Cloning and Expression of Different SARS-CoV-2 S Protein Subunits and Ebola Surface Glycoprotein The RBD of SARS-CoV-2 spike protein (MN908947; AA:319-541) was expressed in 293T cells from a plasmid kindly provided by Florian Krammer and purified using Ni-NTA Agarose (Macherey-Nagel), as previously published (Stadlbauer, D. et al. SARS-CoV-2 Seroconversion in Humans: A Detailed Protocol for a Serological Assay, Antigen Production, and Test Setup. *Curr. Protoc. Microbiol.* 57, (2020)).

SARS-CoV-2 S ectodomain "monomer" without trimerization domain (MN908947; AA:1-1207) and S1 subunit (MN908947; AA:14-529) regions of the spike DNA were amplified from a synthetic gene plasmid (furin site mutated; Wrapp, D. et al. Cryo-EM structure of the 2019-nCoV spike in the prefusion conformation. *Science* 367, 1260-1263 (2020)) by PCR. PCR products were cloned into a modified sleeping beauty transposon expression vector containing a C-terminal thrombin cleavage and a double Strep II purification tag. For the S1 subunit, the tag was added at the 5' end and a BM40 signal peptide was included.

For recombinant protein production, stable HEK293 EBNA cell lines were generated employing the sleeping beauty transposon system (Kowarz, E., Löscher, D. & Marschalek, R. Optimized Sleeping Beauty transposons rapidly generate stable transgenic cell lines. *Biotechnol. J.* 10, 647-653 (2015)).

Briefly, expression constructs were transfected into the HEK293 EBNA cells using FuGENE HD transfection reagent (Promega). After selection with puromycin, cells were induced with doxycycline. Supernatants were filtered and the recombinant proteins purified via Strep-Tactin® XT (IBA Lifescience) resin. Proteins were then eluted by biotin containing TBS-buffer (IBA Lifescience), and dialyzed against TBS-buffer. Ebola surface glycoprotein (EBOV Makona (GenBank KJ660347) lacking the transmembrane domain (Δ651-676)) and HIV-gp140 (strain YU2), also lacking the transmembrane domain, and both containing a GCN4 trimerization domain, were produced and purified as previously described (Ehrhardt, S. A. et al. Polyclonal and convergent antibody response to Ebola virus vaccine rVSV-ZEBOV. *Nat. Med.* 25, 1589-1600 (2019)).

Example 5: Isolation of SARS-CoV-S Ectodomain-Specific IgG$^+$ B Cells

B cells were isolated from PBMCs using CD19-microbeads (Miltenyi Biotec) according to manufacturer's instruction. CD19-labeled cells were separated using MACS LS columns (Miltenyi Biotec). Isolated B cells were stained for 20 minutes on ice with a fluorescence staining-mix containing 4',6-Diamidin-2-phenylindol (DAPI; Thermo Fisher Scientific), anti-human CD20-Alexa Fluor 700 (BD), anti-human IgG-APC (BD), anti-human CD27-PE (BD) and DyLight488-labeled SARS-CoV-2 spike protein (10 μg/mL).

Dapi⁻, CD20⁺, IgG⁺, SARC-CoV-2 spike protein positive cells were sorted using a FACSAria Fusion (Becton Dickinson) in a single cell manner into 96-well plates. All wells contained 4 μl lysis buffer (0.5×PBS, 0.5 U/μl RNAsin (Promega), 0.5 U/μl RNaseOUT (Thermo Fisher Scientific), and 10 mM DTT (Thermo Fisher Scientific), After sorting, plates were immediately stored at −80° C. until further processing.

Example 6: Antibody Heavy/Light Chain Amplification and Sequence Analysis

Single cell amplification of antibody heavy and light chains was mainly performed as previously described (Schommers, P. et al. Restriction of HIV-1 Escape by a Highly Broad and Potent Neutralizing Antibody. *Cell* 180, 471-489.e22 (2020)).

Briefly, reverse transcription was performed with Random Hexamers (Invitrogen), and Superscript IV (Thermo Fisher Scientific) in the presence of RNase-inhibitors RNaseOUT (Thermo Fisher Scientific) and RNasin (Promega). cDNA was used to amplify heavy and light chains using PlatinumTaq HotStart polymerase (Thermo Fisher Scientific) with 6% KB extender and optimized V gene specific primer mixes (Schommers, P. et al. Restriction of HIV-1 Escape by a Highly Broad and Potent Neutralizing Antibody. *Cell* 180, 471-489.e22 (2020)) in a sequential semi-nested approach with minor modifications to increase throughput. PCR products were analyzed by gel electrophoresis for correct sizes and subjected to Sanger sequencing.

For sequence analysis, chromatograms were filtered for a mean Phred score of 28 and a minimal length of 240 nt. Sequences were annotated with IgBLAST and trimmed to extract only the variable region from FWR1 to the end of the J gene. Base calls within the variable region with a Phred score below 16 were masked and sequences with more than 15 masked nucleotides, stop codons, or frameshifts were excluded from further analyses.

Clonal analysis was performed separately for each patient. All productive heavy chain sequences were grouped by identical $V_H/J_H$ gene pairs and the pairwise Levenshtein distance for their CDRH3s was determined. Starting from a random sequence, clone groups were assigned four sequences with a minimal CDRH3 amino acid identity of at least 75% (with respect to the shortest CDRH3). 100 rounds of input sequence randomization and clonal assignment were performed and the result with the lowest number of remaining unassigned (non-clonal) sequences was selected for downstream analyses.

All clones were cross-validated by the investigators taking also into account shared mutations. V gene usage, CDRH3 length and V gene germline identity distributions for all clonal sequences were determined for all input sequences without further collapsing. CDRH3 Hydrophobicity was calculated based on the Eisenberg-scale (Eisenberg, D., Schwarz, E., Komaromy, M. & Wall, R. Analysis of membrane and surface protein sequences with the hydrophobic moment plot. *J. Mol. Biol.* 179, 125-142 (1984)). V gene statistics for neutralizer and non-neutralizer were calculated from collapsed clonal sequences.

For longitudinal analyses on mutation frequencies of recurring clones, a multiple sequence alignment for the B cell sequences was calculated with Clustal Omega (version 1.2.3; Sievers, F. et al. Fast, scalable generation of high-quality protein multiple sequence alignments using Clustal Omega. *Mol. Syst. Biol.* 7, (2011)) using standard parameters.

Example 7: Cloning and Production of Monoclonal Antibodies

Antibody cloning from 1st PCR products was performed as previously described (Schommers, P. et al. Restriction of HIV-1 Escape by a Highly Broad and Potent Neutralizing Antibody. *Cell* 180, 471-489.e22 (2020)) by sequence and ligation independent cloning (SLIC; Von Boehmer, L. et al. Sequencing and cloning of antigen-specific antibodies from mouse memory B cells. *Nat. Protoc.* 11, 1908-1923 (2016)) with a minor modification.

In contrast to the published protocol, PCR amplification for SLIC assembly was performed with extended primers (Kreer, C. et al. openPrimeR for multiplex amplification of highly diverse templates. *J. Immunol. Methods* 480, (2020)) based on covering the complete endogenous leader sequence of all heavy and light chain V genes.

Variable regions with endogenous leader sequences were assembled into mammalien expression vectors for IgH, IgK, and IgL and transfected into HEK293-6E cells for expression and Protein G purification of monoclonal antibodies as previously described (Schommers, P. et al. Restriction of HIV-1 Escape by a Highly Broad and Potent Neutralizing Antibody. *Cell* 180, 471-489.e22 (2020)).

Example 8: ELISA Analysis to Determine Antibody Binding Activity to SARS-CoV-2 S and Subunit Binding ELISA plates (Corning #3369) were coated with 2 μg $ml^{-1}$ of protein in PBS (SARS-CoV-2 spike ectodomain, RBD, or n-terminal truncated S1) or in 2 M Urea (SARS-CoV-2 spike ectodomain “monomer” lacking the trimerization domain) at 4° C. over night. For SARS-CoV-2 spike ectodomain ELISA, plates were blocked with 5% BSA in PBS for 60 min at RT, incubated with primary antibody in 1% BSA in PBS for 90 min, followed by anti-human IgG-HRP (Southern Biotech 2040-05) diluted 1:2500 in 1% BSA in PBS for 60 min at RT.

SARS-CoV-2 spike subunit ELISAs were done following a published protocol (Stadlbauer, D. et al. SARS-CoV-2 Seroconversion in Humans: A Detailed Protocol for a Serological Assay, Antigen Production, and Test Setup. *Curr. Protoc. Microbiol.* 57, (2020)).

ELISAs were developed with ABTS solution (Thermo Fisher 002024) and absorbance was measured at 415 nm-695 nm. Positive binding was defined by an OD>0.25 and an $EC_{50}$<30 μg/ml (cf. FIG. 1). The commercial anti-SARS-CoV-2 ELISA kit for immunoglobulin class G was provided by Euroimmun (Euroimmun Diagnostik, Lubeck, Germany). Antibody detection was done according to manufacturer’s instructions and a concentration of 50 μg/ml of antibodies was used. The samples were tested using the automated platform Euroimmun Analyzer 1.

Example 9: Surface Plasmon Resonance (SPR) Measurements

For SPR measurement, the receptor-binding domain (RBD) of the spike(S) protein of SARS-COV-2 as in SEQ ID NO. 58 was additionally purified by size exclusion chromatography 9SEC) purification with a Superdex200 10/300 column (GE Healthcare). Binding of the RBD to the various mAbs was measured using single-cycle kinetics experiments with a BiaCore™ instrument (GE Healthcare).

Purified mAbs were first immobilized at coupling densities of 800-1200 response units (RU) on a series S sensor chip protein A (GE Healthcare) in PBS and 0.02% sodium azide buffer. One of the four flow cells on the sensor chip was empty to serve as a blank. Soluble RBD was then injected at a series of concentrations (i.e. 0.8, 4, 20, 100, and 500 nM) in PBS at a flow rate of 60 μL/min. The sensor chip was regenerated using 10 mM Glycine-HCl pH 1.5 buffer.

A 1:1 binding model was used to describe the experimental data and to derive kinetic parameters. For some mAbs, a 1:1 binding model did not provide an adequate description for binding. In these cases, we fitted a two-state binding model that assumes two binding constants due to conformational change. In these cases, we report the first binding constants ($K_D^1$).

Binding constants as $K_D$ values have been determined for the following antibodies of the present invention:

| | |
|---|---|
| FnC1t2p1_D4 | 0.20 nM |
| FnC1t2p1_G5 | 0.10 nM |
| MnC2t1p1_A3 | 0.70 nM |
| MnC2t2p1_C11 | 0.02 nM |
| MnC4t2p1_B3 | 0.09 nM |
| MnC4t2p2_A4 | 14 nM |
| MnC5t2p1_G1 | 17 nM |

Example 10: Virus Neutralization Test

SARS-CoV-2 neutralizing activity of poly-IgG samples or human monoclonal antibodies was investigated based on a previously published protocol for MERS-CoV (Koch, T. et al. Safety and immunogenicity of a modified vaccinia virus Ankara vector vaccine candidate for Middle East respiratory syndrome: an open-label, phase 1 trial. *Lancet Infect. Dis.* (2020) doi:10.1016/s1473-3099(20)30248-6).

Briefly, samples were serially diluted in 96-well plates starting from a concentration of 100 μg/ml for monoclonal antibodies. Samples were incubated for 1 h at 37° C. together with 100 50% tissue culture infective doses (TCID50) SARS-CoV-2 (BavPat1/2020 isolate, European Virus Archive Global #026V-03883).

Figure 1B:
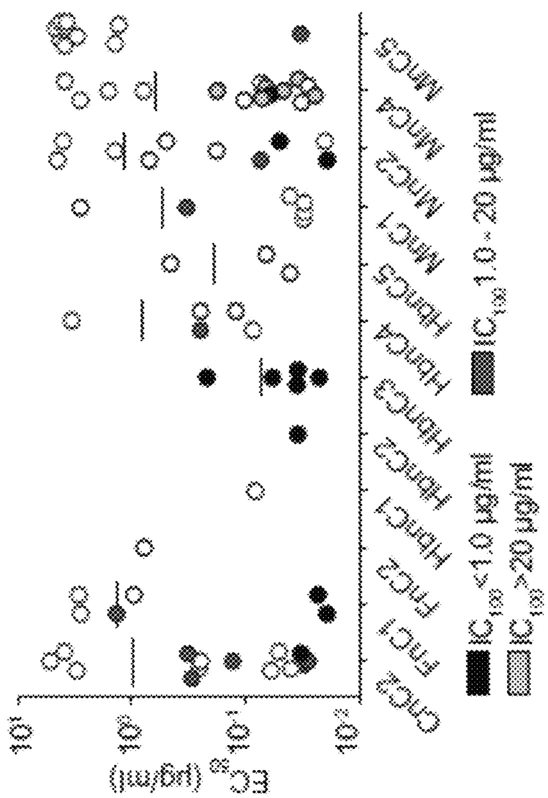
FIG. 1B shows $EC_{50}$ values (mean of duplicates) of SARS-CoV-2 S-ectodomain interacting antibodies per individual patient, from which antibodies were isolated; neutralizing antibodies are labelled in differing shades of grey depending on their $IC_{100}$ values.
Figure 1C:
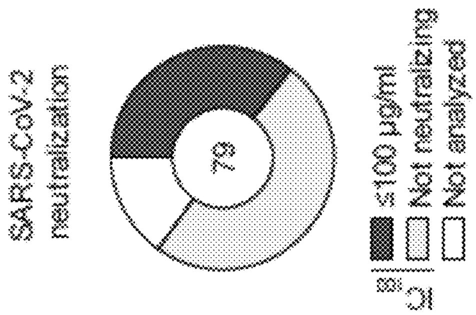
FIG. 1C shows authentic SARS-CoV-2 neutralization activity (complete inhibition of VeroE6 cell infection, $IC_{100}$, in quadruplicates) of S ectodomain-specific antibodies with 28 antibodies having equal or higher neutralization activity than the cut-off value of an $IC_{100}$ of 100 μg/ml.
Figure 2:
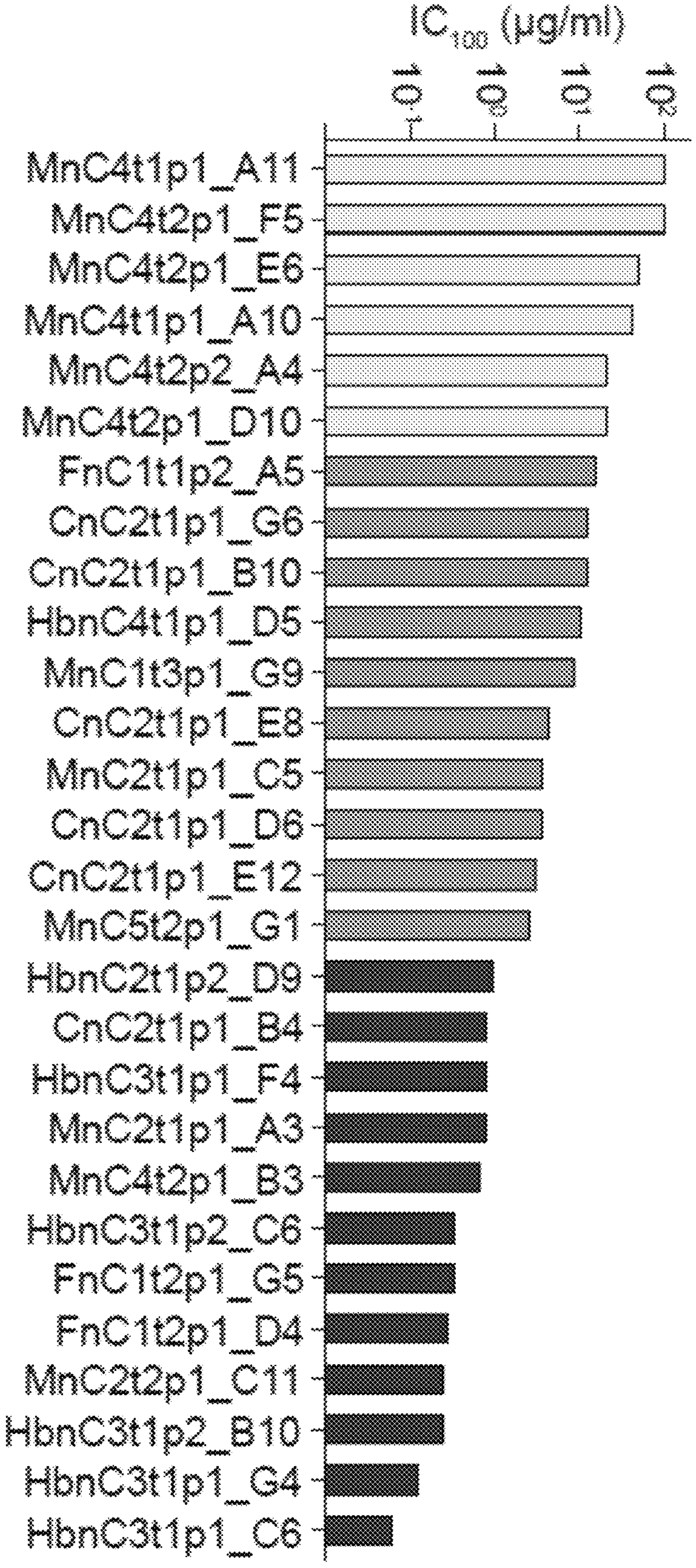
FIG. 2 shows the neutralization efficiency against authentic SARS-CoV-2 expressed in $IC_{100}$ in μg/ml; bars depict the lowest neutralizing mAb concentration.
Figure 3:
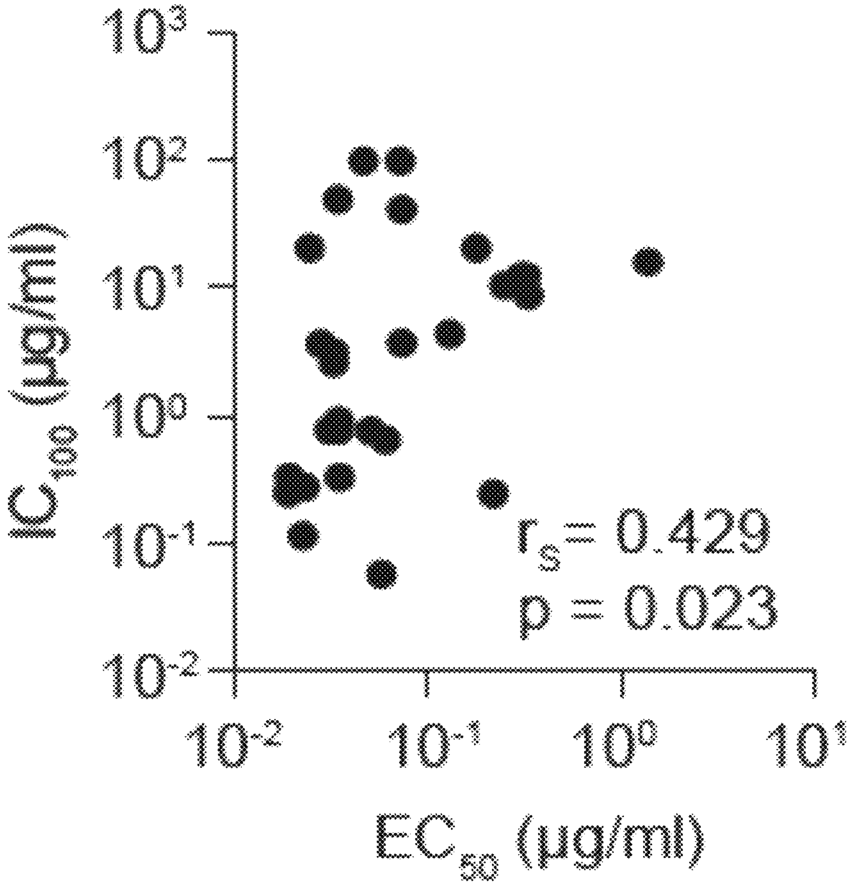
FIG. 3 shows the correlation between SARS-CoV-2 S ectodomain binding as determined by ELISA ($EC_{50}$) and neutralization potency for authentic SARS-CoV-2 ($IC_{100}$); correlation coefficient $r_S$ and approximate p-value were calculated by Spearman's rank-order correlation.

Cytopathic effect (CPE) on VeroE6 cells was analyzed 4 days post-infection. Neutralization was defined as absence of CPE compared to virus controls. For each test, a positive control (neutralizing COVID-19 patient plasma) was used in duplicates as an inter-assay neutralization standard. Results are shown in FIGS. 1 to 3 and in the Table of FIGS. 5A-D.

Example 11: HEp-2 Cell Assay

Monoclonal antibodies were tested at a concentration of 100 μg/ml in PBS using the NOVA Lite HEp-2 ANA Kit (Inova Diagnostics) according to the manufacturer's instructions, including positive and negative kit controls on each substrate slide. HIV-1-reactive antibodies with known reactivity profiles were included as additional controls. Images were acquired using a DMI3000 B microscope (Leica) and an exposure time of 3.5 s, intensity of 100%, and a gain of 10. Results of the autoreactivity assay are shown in FIG. 4.

Example 12: Quantification and Statistics

Flow cytometry analysis and quantifications were done by FlowJo10. GraphPad Prism (v7), and Microsoft Excel for Mac (v14.7.3). Spearman correlation coefficients $r_S$ and approximated two-tailed p values were calculated in GraphPad Prism (v7).

A summary of the results obtained with the antibodies of the invention is shown in the Table of FIGS. 5A-D.

The therapeutic in vivo efficacy of DZIF-10c was investigated in BALB/c mice that were genetically modified to express the SARS-CoV-2 receptor human angiotensin-converting enzyme 2 (ACE2). DZIF-10c, is a variant of HbnC3t1p1_F4, wherein the terminal lysine of the heavy chain constant domain has been removed (HbnC3t1p1_F4 (-K); heavy chain sequence of SEQ ID No. 229 and light chain sequence of SEQ ID No. 230). For this experiment, a recombinant replication-deficient adenovirus encoding for hACE2 is instilled intratracheally. In this model, adenovirus-mediated transduction of hACE2 followed by SARS-CoV-2 challenge ($1.5\times10^4$ $TCID_{50}$ SARS-CoV-2 BavPat1/2020) three days later results in pulmonary viral replication and the development of interstitial pneumonia peaking 4 days after SARS-CoV-2 challenge.

Figures 6A, 6B, 6C:
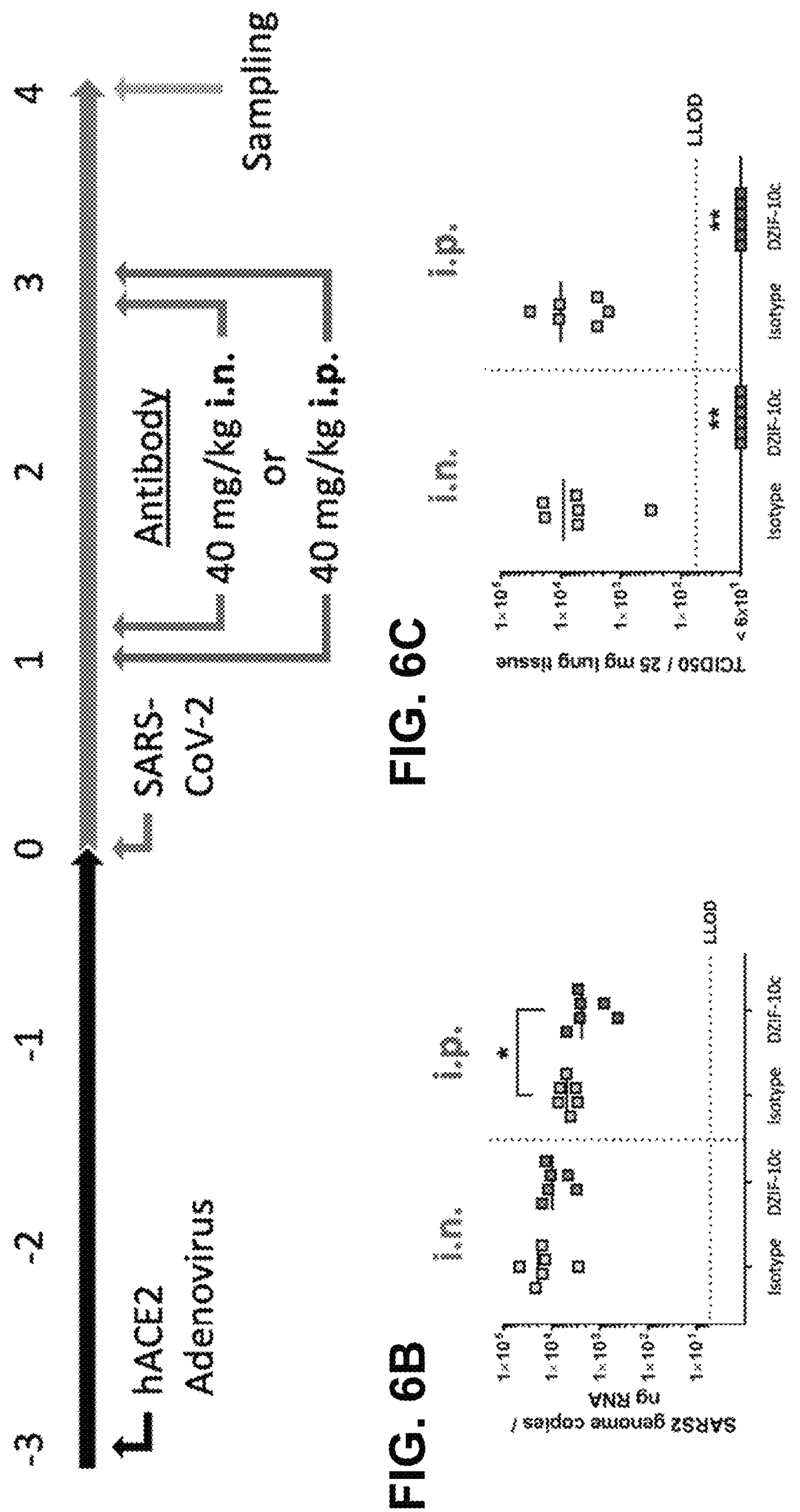
FIGS. 6A, 6B and 6C show the therapeutic efficacy of DZIF-10c in ACE2-transduced SARS-CoV-2-challenged BALB/c mice.

To investigate the in vivo effect of DZIF-10c therapy in ACE2-transduced mice challenged with SARS-CoV-2, DZIF-10c was administered either intraperitoneally or intranasally at a dose of 40 mg/kg on days 1 and 3 after SARS-CoV-2 challenge (see FIG. 6A).

While DZIF-10c therapy resulted in only limited changes on the total SARS-CoV-2 RNA concentration in pulmonary tissues on day 4 as determined by qRT-PCR when compared to an IgG1 isotype control antibody (FIG. 6B), DZIF-10c treatment by either route resulted in undetectable viral titers when determined by virus isolation (FIG. 6C).

Figure 7A:
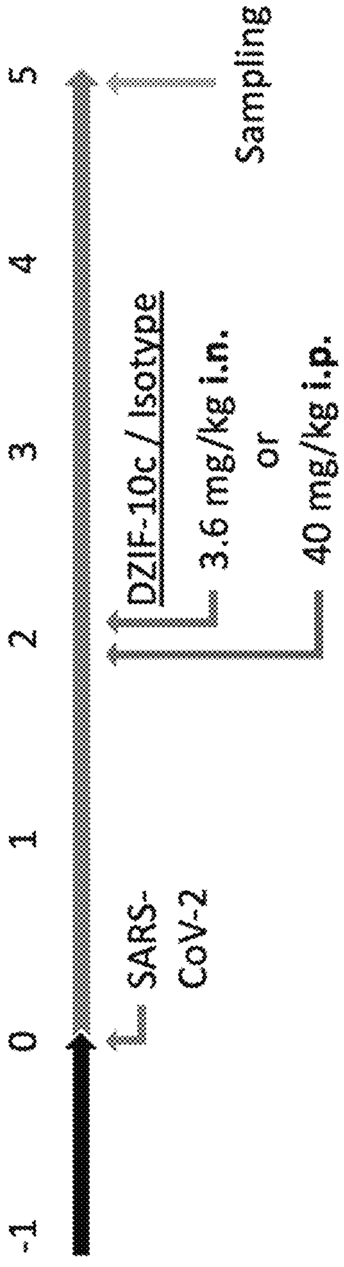
FIGS. 7A, 7B, 7C, and 7D show therapeutic efficacy of DZIF-10c in SARS-CoV-2 challenged golden Syrian hamster.

In a separate small animal model of SARS-CoV-2 infection, golden Syrian hamsters were challenged intranasally with $1\times10^5$ plaque-forming units of SARS-CoV-2. Two days later, animals were treated with either a 40 mg/kg dose of DZIF-10c or isotype control intraperitoneally, or with a 3.6 mg/kg dose of DZIF-10c or isotype control intranasally. Viral RNA and infectious viral titers were obtained in swab samples and/or pulmonary tissues 3 or 5 days after viral challenge (FIG. 7A).

Figure 7B:
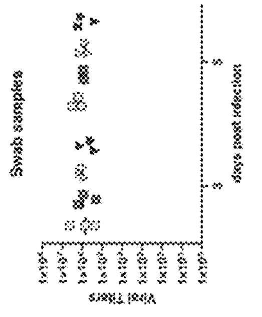
Figure 7C:
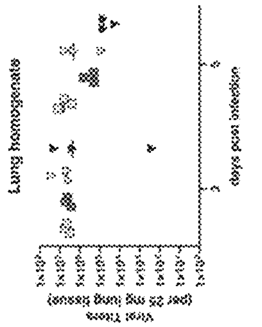
Figure 7D:

Similar to the observations in hACE2-transduced mice, no changes on SARS-CoV-2 RNA levels were detected in respiratory swabs and pulmonary homogenates of SARS-CoV-2-challenged hamsters (FIG. 7B-C). However, compared to isotype control-treated hamsters, reduced titers of infectious SARS-CoV-2 could be detected in pulmonary tissues of hamsters receiving DZIF-10c either intranasally or intraperitoneally (FIG. 7D).

Fc-mediated uptake of antibody-bound viral particles resulting in increased infection and disease is a phenomenon observed for dengue virus, particularly at non- or low-level-neutralizing antibody titers. To investigate whether DZIF-10c may enhance infection of Fc receptor-expressing cells, the effects of SARS-CoV-2-/DZIF-10c-co-incubation on infection of human $CD14^+$ peripheral blood-derived macrophages from one donor were investigated. qRT-PCR analysis of virus-challenged cells indicates that, similar to Vero E6 cells, these macrophages can effectively be infected by human coronaviruses.

Figure 8B:
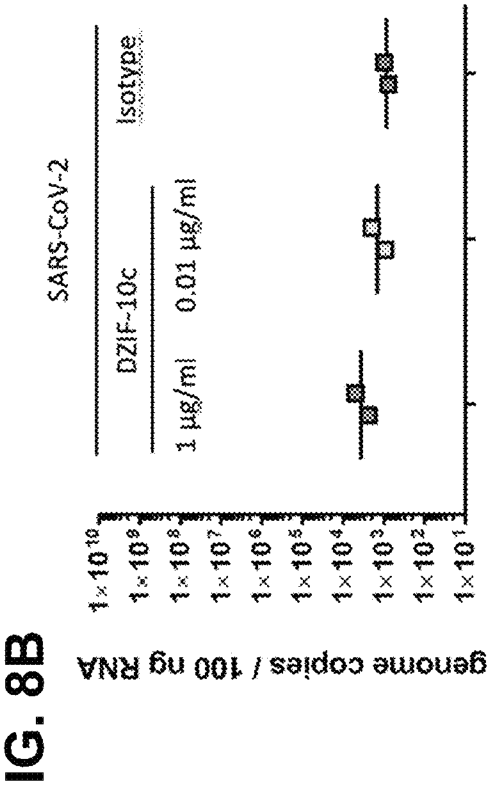
FIG. 8B shows SARS-CoV-2 genome copies after challenge of $CD14^+$ human macrophages with SARS-CoV-2 following a 1 hour co-incubation with DZIF-10c or isotype control antibody. Cells were incubated for four days after viral challenge. LLOD, lower limit of detection.
Figure 8A:
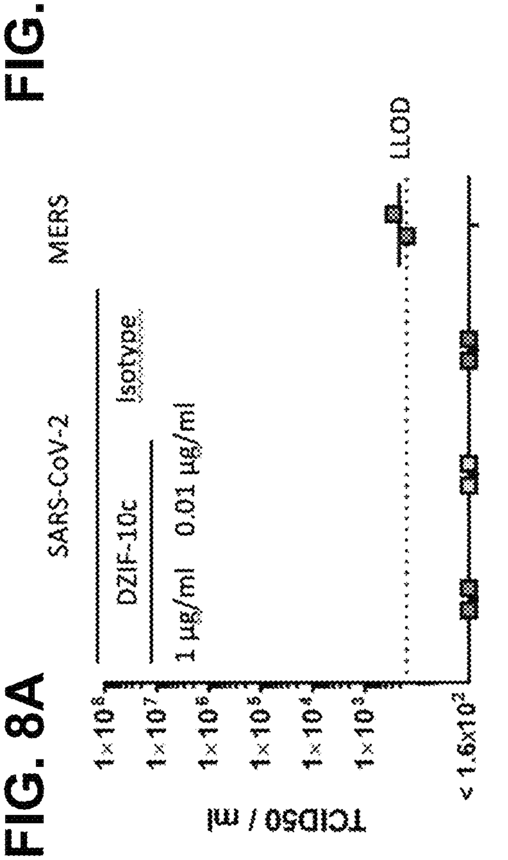
FIG. 8A shows infectious $TCID_{50}$ in cell culture supernatants of $CD14^+$ human macrophages challenged with SARS-CoV-2 after a 1 hour co-incubation with DZIF-10c or isotype control antibody, or after challenge with MERS-CoV.

Infection of $CD14^+$ human macrophages with SARS-CoV-2 was investigated after co-incubation of the virus with IgG1 isotype control antibodies or DZIF-10c at either neutralizing (1 μg/ml) or non-neutralizing (0.01 μg/ml) concentrations. While infection with MERS-CoV could be detected by the isolation of infectious virus, no SARS-CoV-2 could be isolated at either of the tested concentrations (FIG. 8A). Moreover, SARS-CoV-2 genome copies determined in CD14+ macrophages tested at the different conditions did not indicate substantial differences in the absence or presence of DZIF-10c (FIG. 8B).

While susceptibility of CD14+ human macrophages to SARS-CoV-2 may be limited, these observations do not indicate relevant Fc receptor-mediated enhancement of SARS-CoV-2 infection caused by DZIF-10c.

To determine the pharmacokinetic profile of DZIF-10c, rats (*Rattus norvegicus* Wistar) were administered DZIF-10c either intravenously or intratracheally. Concentrations of DZIF-10c in plasma and bronchoalveolar lavage fluid (BALF) were determined using a ligand-binding assay targeting human IgG1. Epithelial lining fluid concentrations were derived from BALF measurements by considering the BALF dilution factor determined as the ratio of urea in serum and BALF (assuming that urea is equally distributed in the body).

Following an intravenous injection of DZIF-10c at a dose of 10 mg/kg body weight to four rats, blood samples were collected after 0.083, 0.5, 2, 8, 24, 48, 72, 168, 240, 312, and 336 hours. DZIF-10c plasma concentrations in all animals were in good agreement, and the linear part of the antibody concentration curve revealed low antibody clearance, a low volume of distribution and a long terminal half-life (mean $t_{1/2}$ of 190 h or 7.9 d) (see following table):

~650-fold higher ELF concentrations (dose normalized) of DZIF-10c compared to i.v. application after 2 h and 24 h, respectively.

The human neonatal Fc receptor (huFcRn) reduces lysosomal degradation of human IgG and plays a key role in antibody half-life. Mice genetically engineered to express the human neonatal Fc receptor can therefore show human antibody pharmacokinetics that more closely resemble the pharmacokinetic profile in humans.

DZIF-10c was investigated in immunodeficient scid mice (B6.Cg-Fcgrt$^{tm1Dcr}$ Prkdc$^{scid}$ Tg(FCGRT)32Dcr/DcrJ) that transgenically express the human neonatal Fc receptor. In these mice, DZIF-10c showed a favorable pharmacokinetic profile after a single intravenous injection of 0.5 mg per mouse that was similar to two human IgG1 antibodies that have a half-life of 2-3 weeks in humans.

In addition, the pharmacokinetic profile of DZIF-10c was investigated in immunodeficient NRG mice that do not express the 112 receptor common gamma chain, carry a knock-out mutation in the Rag1 gene, and do not develop murine lymphocytes or NK cells. Again, DZIF-10c demonstrated a favorable pharmacokinetic profile that was similar or prolonged compared to IgG1 antibodies in clinical investigation.

Pharmacokinetic Profile of DZIF-10c after i.v. administration (rats).

| Parameter | Unit | mean | CV | 1 | 2 | 3 | 4 |
|---|---|---|---|---|---|---|---|
| AUC(0-inf) | nmol· h/L | 112600 | 5.4 | 107700 | 121300 | 111900 | 109500 |
| AUC(0-312 h) | nmol · h/L | 81130 | 2.9 | 79950 | 83800 | 78470 | 82300 |
| AUC(rest, tz-inf) | % | 27.8 | 10.8 | 25.8 | 30.9 | 29.8 | 24.8 |
| C(max) | nmol/L | 1470 | 4.0 | 1443 | 1472 | 1550 | 1413 |
| CL | mL/(min · kg) | 0.00996 | 5.2 | 0.01039 | 0.00923 | 0.01001 | 0.01023 |
| V(ss) | L/kg | 0.1446 | 5.9 | 0.1407 | 0.1475 | 0.1549 | 0.1353 |
| MRT | h | 242.6 | 9.5 | 225.6 | 266.5 | 257.9 | 220.5 |
| t(½) | h | 189.9 | 4.6 | 177.6 | 209.2 | 208.7 | 164.2 |

In addition, administration of a second 10 mg/kg i.v. dose at day 13 resulted in a plasma concentration increase from 115±6.4 nM to 662±44 nM, suggesting no anti-drug antibodies (ADAs) developed.

To determine the DZIF-10c concentration in the epithelial lining fluid after intravenous administration, a bronchoalveolar lavage was performed on day 14, one day after the second 10 mg/kg i.v. application. Analysis of BALF determined a plasma/ELF ratio of 33.2, indicating that the ELF concentration of DZIF-10c was 3% of that found in plasma.

To investigate the pharmacokinetic profile of DZIF-10c after intratracheal (i.t.) application of a dose of 1 mg/kg, a bronchoalveolar lavage was performed in different cohorts of rats after either 2 hours (n=4) or 24 hours (n=4).

Figure 9:
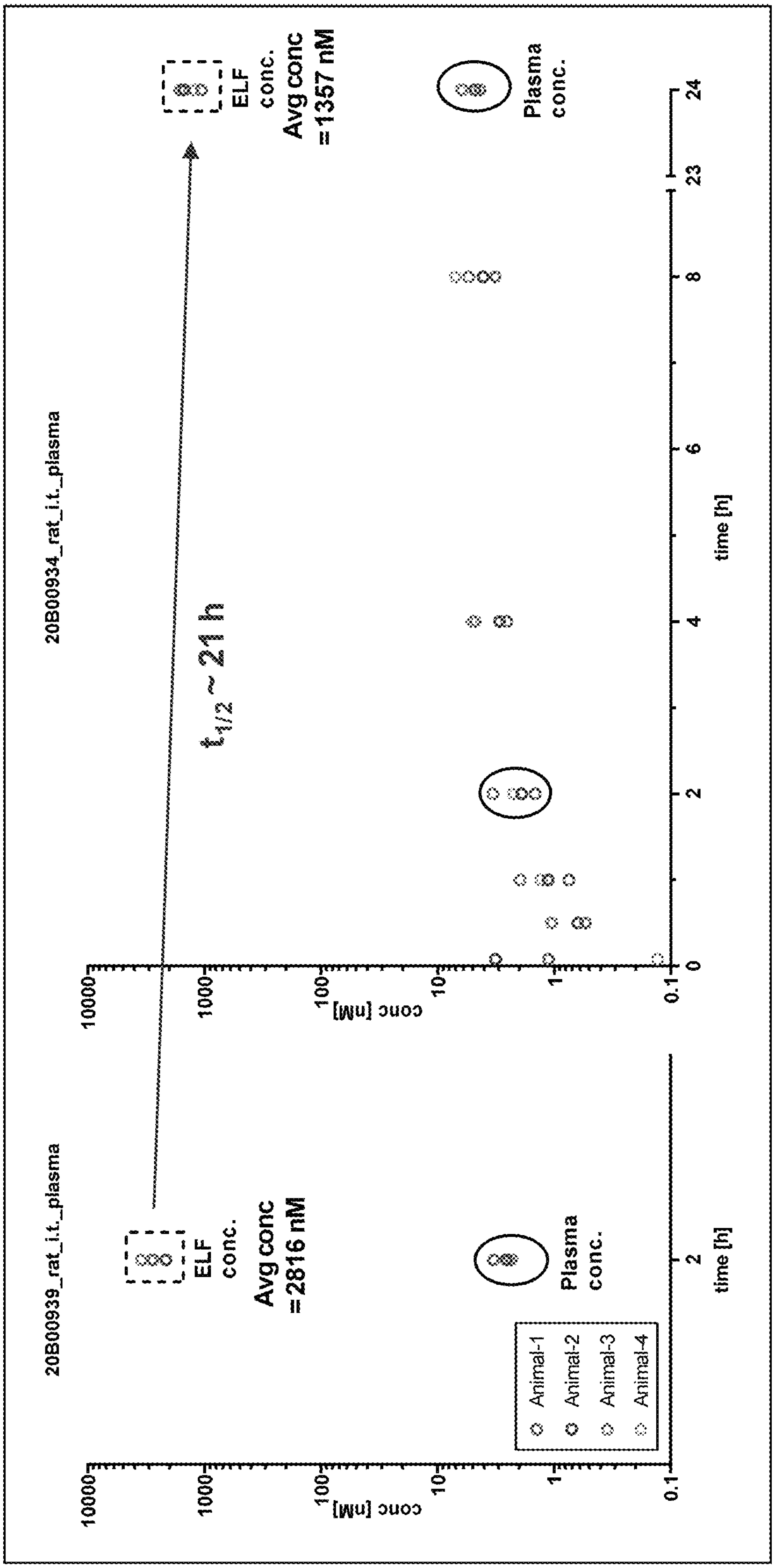
FIG. 9 shows DZIF-10c concentrations in ELF and plasma of Wistar rats after intratracheal administration of a dose of 1 mg/kg.

Upon i.t. administration, mean ELF concentrations of DZIF-10c were ~1000-fold higher and ~250-fold higher compared to plasma after two hours and 24 hours, respectively. The mean half-life of DZIF-10c in ELF was determined to be ~21 hours. A time-dependent increase in plasma concentrations that plateaued at a concentration of 2.5-5.0 nM was reached after four hours (FIG. 9).

Figure 10:
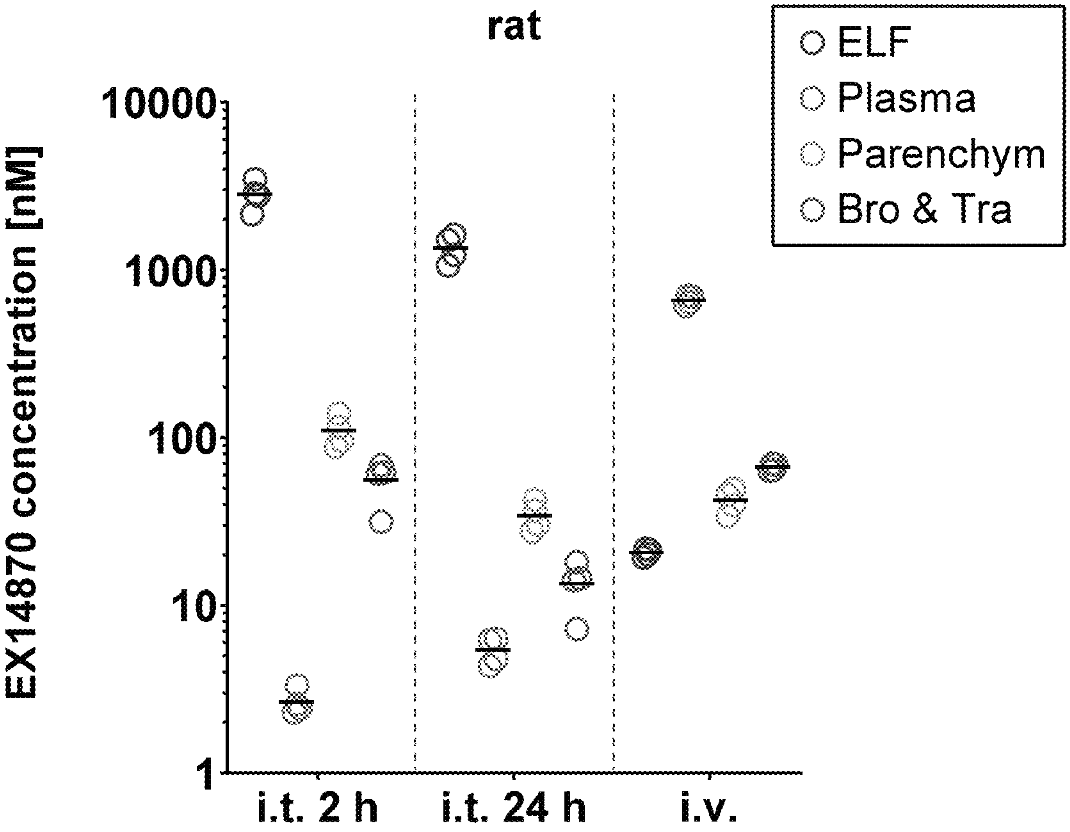
FIG. 10 shows DZIF-10c (referred to as EX14870) concentrations in all investigated tissues of Wistar rats 2 hours or 24 hours after intratracheal application of 1 mg/kg, or 24 hours after the second i.v. application of a dose of 10 mg/kg. Bro & Tra, bronchi and trachea.

Similar antibody concentrations were determined in the lower and upper airway tissues across all dosing groups (10 mg/kg i.v., 1 mg/kg i.t.) (FIG. 10).

Overall, the analysis of plasma and ELF concentrations of DZIF-10c for the different administration routes in Wistar rats revealed that i.t. application resulted in ~1300-fold and

Example 13: Higher Affinity and Alternative Binding Mode of DZIF-10c Vs. Two Comparator Antibodies Various properties of DZIF-10c were compared to two antibodies (REGN10987, REGN10933) resynthesized from J. Hansen et al., *Science* 10.1126/science.abd0827 (2020). As shown in FIG. 14, DZIF-10c showed a significantly higher binding affinity as the comparators, and a binding mode covering a larger area of the antigen, making it more suitable for use as a single compound treatment.

Example 14: Treatment of SARS-CoV-2-Infection

As an example for antibodies of the invention, DZIF-10c can be used for the treatment of SARS-CoV-2-infection, the prevention of SARS-CoV-2-infection, or as post-exposure prophylaxis in individuals recently exposed to SARS-CoV-2.

DZIF-10c can be provided as a single-use sterile solution at a concentration of 50 mg/mL. Each vial of DZIF-10c drug product may contain 20 mL of a buffered solution composed of acetic acid, sodium acetate, glycine, trehalose, and polysorbate 20 (see table).

| Component | Concentration[mg/mL] |
|---|---|
| DZIF-10c | 50.00 |
| Acetic acid glacial | 0.25 |

-continued

| Component | Concentration[mg/mL] |
|---|---|
| Sodium acetate trihydrate | 2.15 |
| Glycine | 16.52 |
| Trehalose dihydrate | 7.57 |
| Polysorbate 20 | 0.40 |
| Water for Injection (WFI) | Ad 1 mL |

In an embodiment, DZIF-10c is formulated at about 50 mg/ml in about 20 mM acetate, about 220 mM glycine, about 20 mM trehalose, about 0.4 g/L polysorbate 20 at a pH of about 5.5.

DZIF-10c can be applied by intravenous infusion or inhaled administration after aerosolization using a nebulizer.

DZIF-10c can be administered intravenously at doses of about 2.5 mg/kg, about 10 mg/kg, or about 40 mg/kg by intravenous infusion diluted in formulation buffer over 60 minutes (+/−10 minutes) using a 0.2 μm nylon in-line filter. The formulation exemplified above may be diluted to the appropriate volume with formulation buffer.

For the inhaled administration, individuals may be treated with doses of 50 mg, 100 mg, or 250 mg per treatment through a mouthpiece following aerosol generation using a mesh nebulizer, or a jet nebulizer. The formulation exemplified above may be diluted to the appropriate volume with formulation buffer.

A single inhalation may be followed by a single intravenous infusion.

Example 15: Antibody Formulations

In the context of the present invention, a formulation was developed which has several advantages. Importantly, it represents a solution which can be used for multiple purposes such as for intravenous (i.v.), inhalative (inh.) via oral and nasal, and subcutaneous (s.c.) administration. In addition, it can be used for pediatric use. In particular, it can be used both for an injection presentation as well as a presentation for inhalation e.g. by means of a jet nebulizer.

Furthermore, the formulation as described is applicable especially for high dose administrations needed in pandemic situations or oncology (>1 g per patient per day) where commonly used excipients often exceed the level of maximum daily exposure for patients, and thus reaching critical toxicological level. In addition, sugar and polyols are commonly used to maintain the solution isotonicity known to be essential for e.g. i.v. and s.c. application. However, for high dose administrations sugar or polyols often exceed the maximum daily exposure levels for patients.

The particular combination of excipients used in this formulation meet both the maximum daily exposure level for patients as well as for the solution tonicity evaluated for high dose administration of up to 5 g per patient per day considering 100 kg patient population.

Therefore, a pharmaceutical composition is generally provided herein comprising an antibody or antigen-binding fragment thereof in an aqueous solution at a concentration of 10-260 mg/mL, 10-25 mM acetate, 172.7-259.1 mM glycine, 17.3-25.9 mM trehalose, 0.2-0.6 g/L polysorbate 20 (polyoxyethylene (20)-sorbitan-monolaurate), with an osmolality of 240-340 mOsmol/kg and a pH of 5.2-5.8. The formulation provided has been shown to work for different antibodies.

In one embodiment, a pharmaceutical composition is provided comprising an an antibody comprising a heavy chain of sequence SEQ ID NO: 229, and a light chain of sequence SEQ ID NO: 230, or antigen-binding fragment thereof, in an aqueous solution at a concentration of 10-260 mg/mL, 10-25 mM acetate, 172.7-259.1 mM glycine, 17.3-25.9 mM trehalose, 0.2-0.6 g/L polysorbate 20 (polyoxyethylene (20)-sorbitan-monolaurate), with an osmolality of 240-340 mOsmol/kg and a pH of 5.2-5.8.

In another embodiment, a pharmaceutical composition is provided comprising an antibody comprising a heavy chain of sequence SEQ ID NO: 229, and a light chain of sequence SEQ ID NO: 230, or antigen-binding fragment thereof, at 50 mg/ml in 20 mM acetate, 220 mM glycine, 20 mM trehalose, 0.4 g/L polysorbate 20 at pH 5.5.

The formulation was shown to be applicable as high-concentrated liquid formulation (HLCF), essential in order to accommodate high dose administration s.c. via syringe by injection of considerably low volume (max. 1.5-2.0 mL) into the patient. The aforementioned solution without active ingredient (antibody) can be used as dedicated diluent, solvent for dilution, and placebo. It has further been shown to be compatible with commercial clinical dilution media.

The pharmaceutical composition as described could be demonstrated to efficiently stabilize DZIF-10c and other antibodies for inhalative administration using (i) different nebulizer systems (e.g. mesh nebulizer, jet nebulizer), (ii) diluted and undiluted formulation (different API concentration), and (iii) different masks (oral and nasal).

The formulation was shown to be stable in different container closure systems (20 mL and 6 mL Type I glass vial) covering a wide range of technical parameter (e.g. surface/volume ratio).

TABLE 1

Example formulations for antibodies of the invention

| Annotation | Buffer | pH | Excipient 1 | Excipient 2 | PS20 | API conc. |
|---|---|---|---|---|---|---|
| F1 | 20 mM Histidine | 6.0 | — | 240 mM Trehalose | 0.4 g/L | 50 mg/mL |
| F2 | 20 mM Succinate | 5.7 | — | 240 mM Trehalose | 0.4 g/L | |
| F3 | 20 mM Acetate | 5.4 | — | 240 mM Trehalose | 0.4 g/L | |
| F4 | 10 mM Acetate | 5.4 | 50 mM Methionine | 190 mM Trehalose | 0.4 g/L | |
| F5 | 20 mM Acetate | 5.5 | 220 mM Glycine | 20 mM Trehalose | 0.4 g/L | |
| F6 | 20 mM Citrate | 6.5 | 220 mM Glycine | 20 mM Trehalose | 0.4 g/L | |
| F7 | 20 mM Histidine | 6.0 | 220 mM Glycine | 20 mM Trehalose | 0.4 g/L | |
| F8 | 20 mM Histidine | 6.0 | — | 180 mM Trehalose | 0.4 g/L | |

Formulation F5 showed a stabilizing effect when tested in different commercially available nebulizer systems (mesh and jet nebulizers), see Table 2.

TABLE 2

Product quality parameters upon nebulization of formulation F5 using different nebulizer

| | | Control unnebulized | Aerogen Solo ® nebulized | eFlow-Rapid ® nebulized | Phillips InnoSpire Go ® nebulized | Pariboy ® nebulized | Droh ® nebulized |
|---|---|---|---|---|---|---|---|
| UV/Vis (mg/mL) | | 48.6 | 48.3 | 48.8 | 48.8 | 61.3 | 68.8 |
| Osmolality (mOsmol/kg) | | 291 | 292 | 291 | 293 | 374 | 429 |
| Surface Tension (mN/m) | | 38.2 | N/A | N/A | N/A | N/A | N/A |
| UP-SEC (%) | HMW | 0.6 | 0.5 | 0.5 | 0.5 | 0.5 | 0.5 |
| | Monomer | 98.8 | 98.9 | 98.9 | 98.9 | 98.9 | 98.9 |
| | LMW | 0.6 | 0.6 | 0.6 | 0.6 | 0.6 | 0.6 |
| CGE (non-red) (%) | HMW | 0.2 | 0.2 | 0.2 | 0.2 | 0.2 | 0.2 |
| | Monomer | 96.5 | 96.6 | 96.4 | 96.5 | 96.5 | 96.4 |
| | LMW | 3.4 | 3.3 | 3.5 | 3.3 | 3.4 | 3.4 |
| SPR Binding Activity (RLCA %) | | 100 | 100 | 100 | 100 | 100 | 100 |

Different formulations according to Table 1 were tested in the Aerogen Solo® nebulizer in undiluted and diluted formulation

TABLE 3

Results of undiluted formulations (50 mg/mL DZIF-10c)

| | | Ref. Stand. | F5 | | F6 | | F7 | | F8 | |
|---|---|---|---|---|---|---|---|---|---|---|
| | | initial | initial | nebulized | initial | nebulized | initial | nebulized | initial | nebulized |
| UV/Vis (mg/mL) | | 50.1 | 50.4 | | 50.2 | | 50.9 | | 50.8 | |
| pH (-) | | 5.5. | 5.5 | 5.5 | 6.4 | 6.4 | 6.0 | 6.0 | 6.0 | 6.0 |
| Osmolality (mOsmol/kg) | | | 292 | N/A | 322 | N/A | 284 | N/A | 241 | N/A |
| Surface Tension (mN/m) | | | 38.98 | N/A | 39.93 | N/A | 39.00 | N/A | 38.56 | N/A |
| Viscosity at 20° C. (mPas) | | | 1.76 | N/A | 1.85 | N/A | 1.82 | N/A | 1.97 | N/A |
| Density at 20° C. (g/mL) | | | 1.023 | N/A | 1.026 | N/A | 1.024 | N/A | 1.038 | N/A |
| UP-SEC (%) | HMW | 0.6 | 0.4 | 0.4 | 0.7 | 0.7 | 0.4 | 0.4 | 0.4 | 0.4 |
| | Monomer | 98.9 | 99.1 | 99.0 | 98.7 | 98.7 | 99.0 | 99.0 | 99.0 | 99.0 |
| | LMW | 0.5 | 0.6 | 0.6 | 0.6 | 0.6 | 0.6 | 0.6 | 0.6 | 0.6 |
| CGE (non-red) (%) | HMW | 0.3 | 0.1 | 0.1 | 0.3 | 0.3 | 0.2 | 0.1 | 0.2 | 0.2 |
| | Monomer | 96.4 | 96.6 | 96.6 | 96.4 | 96.5 | 96.5 | 96.5 | 96.5 | 96.5 |
| | LMW | 3.2 | 3.3 | 3.3 | 3.2 | 3.3 | 3.3 | 3.3 | 3.3 | 3.4 |
| CGE (red.) (%) | HMW | 1.2 | 1.1 | 1.1 | 1.2 | 1.1 | 1.0 | 1.0 | 1.0 | 1.0 |
| | HC + LC | 97.8 | 97.9 | 98.0 | 97.8 | 98.0 | 98.1 | 98.1 | 98.0 | 98.0 |
| | LMW | 1.0 | 1.0 | 1.0 | 1.0 | 0.9 | 0.9 | 0.9 | 1.0 | 1.0 |
| SPR Binding Activity (RLCA %) | | 100 | 96 | 96 | 95 | 96 | 96 | 96 | 96 | 96 |

TABLE 4

Results of 1:5 diluted formulations (10 mg/mL DZIF-10c)

| | Ref. Stand. | F5 | | F6 | | F7 | | F8 | |
|---|---|---|---|---|---|---|---|---|---|
| | initial | initial | nebulized | initial | nebulized | initial | nebulized | initial | nebulized |
| UV/Vis (mg/mL) | 50.1 | 9.9 | | 9.9 | | 9.9 | | 10.1 | |
| pH (-) | 5.5 | 5.5 | 5.5 | 6.5 | 6.5 | 6.0 | 6.0 | 6.0 | 6.0 |
| Osmolality (mOsmol/kg) | | N/A | N/A | N/A | N/A | N/A | N/A | N/A | N/A |
| Surface Tension (mN/m) | | 39.29 | N/A | 40.20 | N/A | 40.08 | N/A | 38.56 | N/A |
| Viscosity at 20° C. (mPas) | | 1.21 | N/A | 1.23 | N/A | 1.23 | N/A | 1.40 | N/A |
| Density at 20 ° C. (g/mL) | | 1.012 | N/A | 1.015 | N/A | 1.012 | N/A | 1.027 | N/A |

TABLE 4-continued

| Results of 1:5 diluted formulations (10 mg/mL DZIF-10c) | | | | | | | | | | |
|---|---|---|---|---|---|---|---|---|---|---|
| | | Ref. Stand. | F5 | | F6 | | F7 | | F8 | |
| | | initial | initial | nebulized | initial | nebulized | initial | nebulized | initial | nebulized |
| UP-SEC (%) | HMW | 0.6 | 0.4 | 0.4 | 0.7 | 0.7 | 0.4 | 0.5 | 0.4 | 0.5 |
| | Monomer | 98.9 | 99.1 | 99.0 | 98.7 | 98.6 | 99.0 | 99.0 | 99.0 | 99.0 |
| | LMW | 0.5 | 0.6 | 0.6 | 0.6 | 0.6 | 0.6 | 0.6 | 0.6 | 0.6 |
| CGE (non-red) (%) | HMW | 0.3 | 0.1 | 0.1 | 0.3 | 0.4 | 0.2 | 0.2 | 0.2 | 0.2 |
| | Monomer | 96.4 | 96.6 | 96.6 | 96.4 | 96.2 | 96.4 | 96.4 | 96.3 | 96.2 |
| | LMW | 3.2 | 3.3 | 3.3 | 3.2 | 3.4 | 3.4 | 3.5 | 3.5 | 3.5 |
| CGE (red.) (%) | HMW | 1.2 | 1.1 | 1.1 | 1.2 | 1.3 | 0.9 | 1.0 | 1.0 | 1.0 |
| | HC + LC | 97.8 | 97.9 | 98.0 | 97.8 | 98.0 | 98.2 | 98.1 | 98.0 | 98.0 |
| | LMW | 1.0 | 1.0 | 1.0 | 1.0 | 1.1 | 0.9 | 1.0 | 1.0 | 1.0 |
| SPR Binding Activity (RLCA %) | | 100 | 96 | 96 | 96 | 96 | 96 | 96 | 96 | 96 |

Figure 11B:
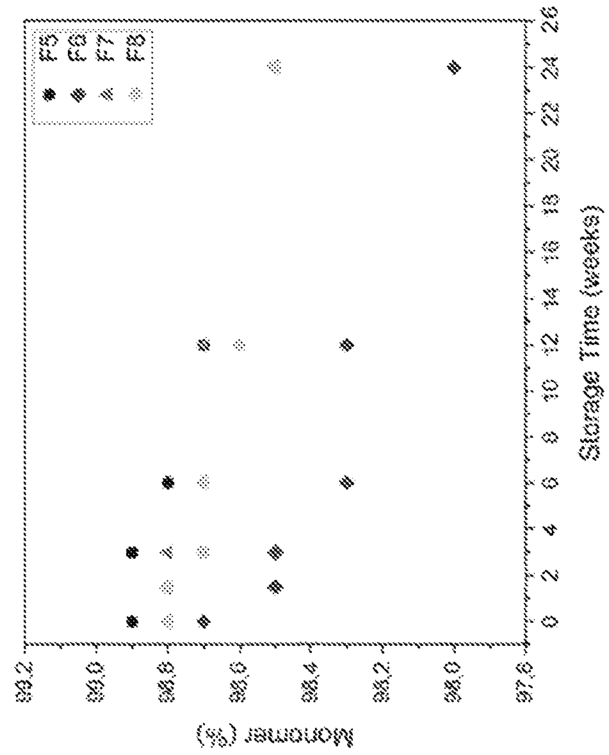
FIG. 11B shows stability data at intended storage condition (5° C.) of DZIF-10c in formulations F5-F8 in terms of percentage of monomer.

Stability data of formulations F5 to F8 at intended storage conditions (5° C.) have been measured via the percentage of high molecular weight species (HMW (%) in A) or via the percentage of monomer (monomer (%) in B) over a storage time of up to 24 weeks. Results of this measurement are shown in FIG. 11.

Example 16: Assessment of the Antiviral Efficacy of Two Prophylactic Nebulizations of the Antibody DZIF-10c in Cynomolgus Monkeys The antiviral efficacy of two prophylactic nebulizations of the antibody DZIF-10c was assessed in 6 cynomolgus monkeys prior to their infection with SARS-CoV-2. For the study, 6 cynomolgus monkeys (*Macaca fascicularis*) were divided in two treatment groups: 4 animals were included in the treatment group that received antibody before infection, while two animals received vehicle only before infection.

Animals of the treatment group received two applications of 10 ml DZIF-10c antibody (50 mg/mL in 20 mM acetate, 220 mM glycine, 20 mM trehalose, 0.04% (w/v) Polysorbate 20, pH 5,5) 4 (D-4) and 2 (D-2) days before infection. Application was with an Aerogen Solo® nebulizer (Aerogen GmbH, Ratingen, Germany) and a suitable face mask (Laerdal Medical GmbH, Puchheim, Germany, size S).

At day of infection (D0), all animals were inoculated with $10^7$ $TCID_{50}$ SARS-CoV-2 strain hCoV-19/France/OCC-NRC02765/2020 (accession GISAID "EPI_ISL_640002, spike substitution D614G, K1073N) by intranasal (IN) application of 500 μL per nostril with a microsprayer device (model IA-1B, PennCentury®) connected to a 1 mL safety syringe with Luer Lock, and by intra-tracheal (IT) infection by spraying 1 mL of the inoculum in the trachea using a microsprayer device (model IA-1B, PennCentury™) connected to a 1 mL safety syringe with Luer Lock.

Daily blood and saliva samples, nasopharyngeal and oropharyngeal swabs were collected for analysis. Bronchoalveolar lavages were taken at D2, D4, and D6. Clinical monitoring included body temperature, food consumption, and body weight. Necropsy at D6 included histopathology of the lungs and viral load assay of lungs, nasal mucosa, oropharynx, and kidneys.

Figure 12:
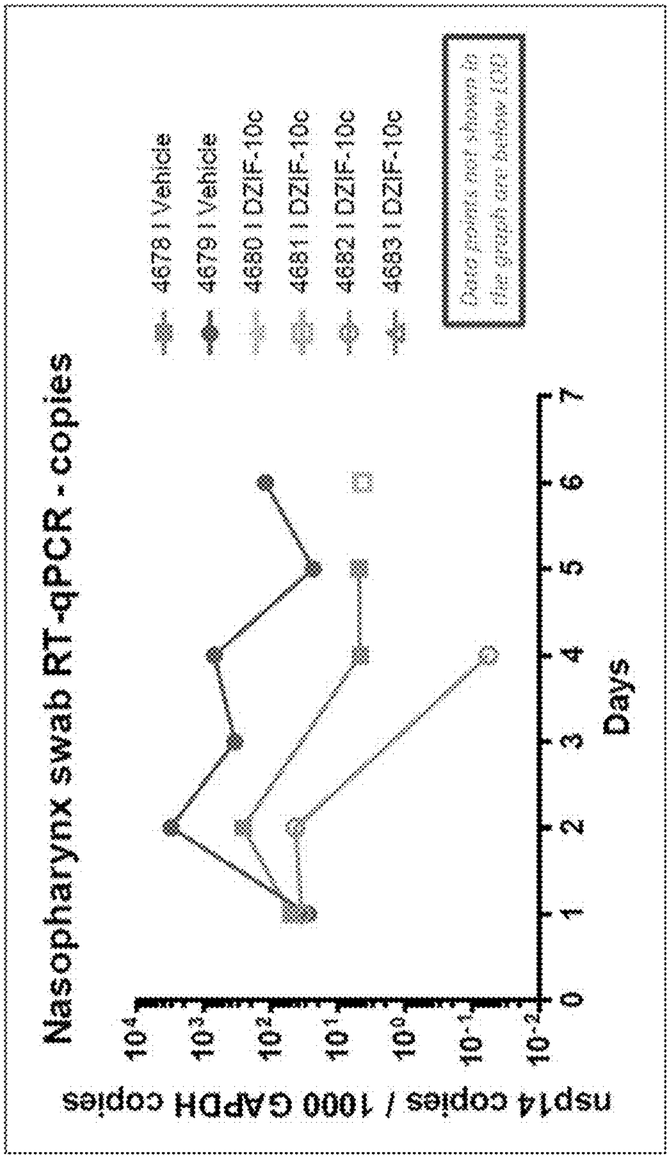
FIG. 12 shows SARS-CoV-2 load in nasopharyngeal swabs of animals pretreated with DZIF-10c or vehicle prior to infection; LOD=limit of detection.
Figure 13:
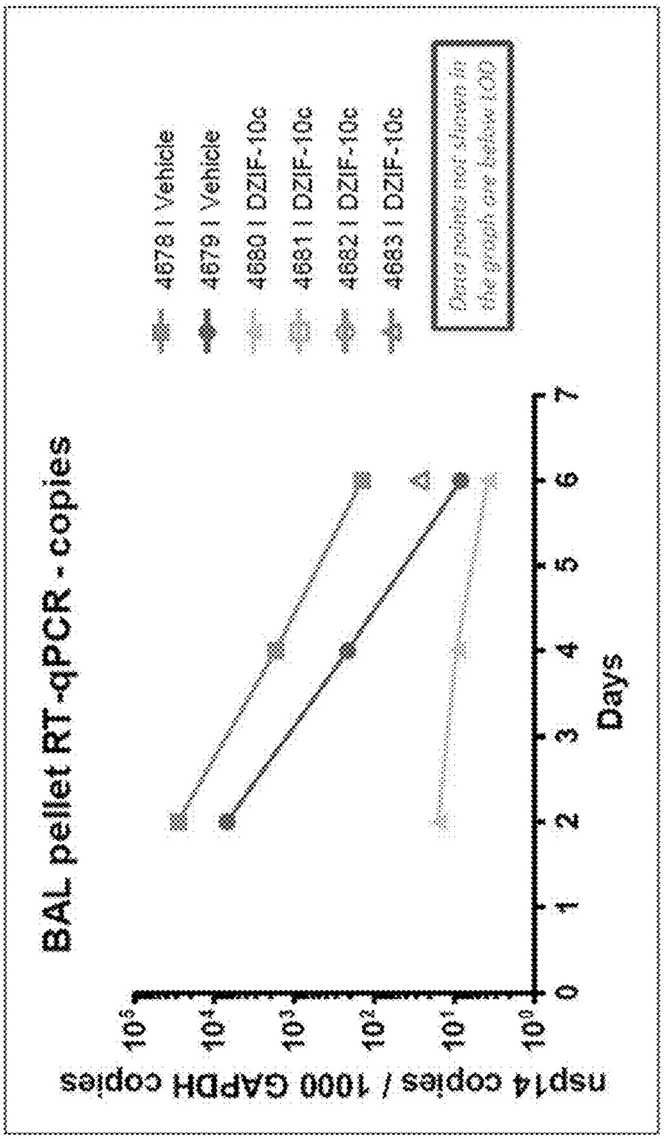
FIG. 13 shows SARS-CoV-2 load in bronchoalveolar lavages (BAL) of animals pretreated with DZIF-10c or vehicle prior to infection; LOD=limit of detection.

In nasopharyngeal swabs and bronchoalveolar lavage (BAL), viral copies could be found in both control animals after infection. By contrast, the treated animals showed either results below the limit of detection (LOD) or at levels several logs below that of control animals. Results of the analysis of nasopharyngeal swabs of all animals are shown in FIG. 12, while results of the analysis of bronchoalveolar lavages are shown in FIG. 13.

Body temperature: Both control animals showed a clear and prolonged hyperthermia following infection with SARS-CoV-2. Prophylactic treatment with DZIF-10c either delayed the occurrence of hyperthermia, shortened its duration and decreased its intensity, or altogether prevented its onset.

Macroscopic and microscopic observation of lungs: Both control animal lungs showed hardened, dark red areas, similar to what has been described as lung consolidations in major publications. The lungs of the four treated animals appeared healthy without any signs of lungs injury. All these observations were confirmed by the microscopic observations: marked, extensive, subacute, bronchointerstitial inflammation in most slides of both control animals, and very limited or no bronchointerstitial inflammation in group 2 animals.

In summary, these results indicate that prophylactic treatment with DZIF-10c by inhalative application decreased the viral load in terms of viral copies and infectious virus, reduced or prevented clinical symptoms (hyperthermia) and prevented lung pathology.

The invention claimed is:

1. A nucleic acid encoding an antibody or antigen-binding fragment thereof which specifically binds to an epitope of the receptor-binding domain (RBD) of the spike(S) protein of SARS-related coronavirus 2 (SARS-COV-2), wherein the antibody or antigen-binding fragment thereof comprises a heavy chain variable region having a heavy chain CDR1, CDR2, and CDR3 and a light chain variable region having a light chain CDR1, CDR2, and CDR3, (a) wherein the heavy chain CDR1, CDR2, and CDR3 comprises SEQ ID NO: 59, SEQ ID NO: 60, and SEQ ID NO: 61, respectively; and wherein the light chain CDR1, CDR2, and CDR3 comprises SEQ ID NO: 62, SEQ ID NO: 63, and SEQ ID NO: 64, respectively; or (b) wherein the heavy chain CDR1, CDR2, and CDR3 comprises SEQ ID NO: 119, SEQ ID NO: 120, and SEQ ID NO: 121, respectively; and wherein the light chain CDR1, CDR2, and CDR3 comprises SEQ ID NO: 122, SEQ ID NO: 123, and SEQ ID NO: 124, respectively.

2. The nucleic acid of claim 1, wherein the antibody or antigen-binding fragment thereof comprises a heavy chain variable region and a light chain variable region, (a) wherein when the heavy chain CDR1, CDR2, and CDR3 comprises SEQ ID NO: 59, SEQ ID NO: 60, and SEQ ID NO: 61, respectively; and the light chain CDR1, CDR2, and CDR3 comprises SEQ ID NO: 62, SEQ ID NO: 63, and SEQ ID NO: 64, respectively, the heavy chain variable region comprises SEQ ID NO: 1 and the light chain variable region comprises SEQ ID NO: 2; or (b) wherein when the heavy chain CDR1, CDR2, and CDR3 comprises SEQ ID NO: 119, SEQ ID NO: 120, and SEQ ID NO: 121, respectively; and the light chain CDR1, CDR2, and CDR3 comprises SEQ ID NO: 122, SEQ ID NO: 123, and SEQ ID NO: 124, respectively, the heavy chain variable region comprises SEQ ID NO: 21 and the light chain variable region comprises SEQ ID NO: 22.

3. The nucleic acid of claim 1, wherein the antibody or antigen-binding fragment thereof exhibits a neutralization potency of less than 10 μg/ml, wherein the neutralization potency is a lowest antibody dose leading to complete absence of cytopathic effects ($IC_{100}$) against a SARS-COV-2 isolate on VeroE6 cells.

4. The nucleic acid of claim 3, wherein the antibody or antigen-binding fragment thereof exhibits a neutralization potency of less than 1 μg/ml.

5. The nucleic acid according to claim 1, wherein the antibody or antigen-binding fragment thereof does not display autoreactivity at concentrations of 100 μg/ml of the antibody or antigen-binding fragment thereof when tested against permeabilized HEp-2 cells using an antinuclear antibody (ANA) testing kit.

6. The nucleic acid of claim 1, wherein when the heavy chain CDR1, CDR2, and CDR3 comprises SEQ ID NO: 119, SEQ ID NO: 120, and SEQ ID NO: 121, respectively; and the light chain CDR1, CDR2, and CDR3 comprises SEQ ID NO: 122, SEQ ID NO: 123, and SEQ ID NO: 124, respectively, the antibody has a heavy chain amino acid sequence of SEQ ID NO: 229 and a light chain amino acid sequence of SEQ ID NO: 230.

7. A pharmaceutical composition comprising the antibody or antigen-binding fragment thereof of claim 1 and at least one pharmaceutically acceptable excipient that is a nonionic surfactant.

8. The pharmaceutical composition of claim 7, wherein the nonionic surfactant is a polyoxyethylensorbitan fatty acid ester or a polysorbate.

9. The pharmaceutical composition of claim 7, wherein the pharmaceutical composition is a vaccination composition for a human and/or animal subject.

10. A kit comprising the pharmaceutical composition of claim 7 and a container.

11. An expression vector comprising the nucleic acid of claim 1.

12. A host cell comprising the nucleic acid according to claim 1, in functional association with an expression control sequence.

13. A method of producing the isolated antibody or antigen binding fragment thereof of claim 1, comprising:

(a) cultivating the host cell of claim 12 under conditions allowing expression of the antibody or antigen binding fragment thereof, and (b) recovering the antibody or antigen binding fragment thereof.

14. A nucleic acid encoding an antibody or antigen-binding fragment thereof which specifically binds to the receptor-binding domain (RBD) of the spike(S) protein of SARS-COV-2 comprising SEQ ID NO: 58, comprising a heavy chain variable region comprising a heavy chain CDR1, CDR2, and CDR3 and light chain variable region comprising a light chain CDR1, CDR2, and CDR3, wherein the heavy chain CDR1, CDR2, and CDR3 comprises GFTFRRYG (SEQ ID NO: 119), ILFDGSNK (SEQ ID NO: 120) and AKGGDYEWELLES (SEQ ID NO: 121), respectively;

and wherein the light chain CDR1, CDR2, and CDR3 comprises QSIDNW (SEQ ID NO: 122), KAS (SEQ ID NO: 123), and QHYHSFPLT (SEQ ID NO: 124), respectively.

15. The nucleic acid of claim 14, wherein the antibody or antigen-binding fragment thereof heavy chain variable region comprises SEQ ID NO: 21 and the light chain variable region comprises SEQ ID NO: 22.

16. The nucleic acid of claim 14, wherein the antibody or antigen-binding fragment thereof comprises a heavy chain and a light chain, wherein the heavy chain comprises SEQ ID NO: 229 and the light chain comprises SEQ ID NO: 230.

17. A pharmaceutical composition comprising the antibody or antigen-binding fragment thereof of claim 14 and at least one pharmaceutically acceptable excipient that is a nonionic surfactant.

18. The pharmaceutical composition of claim 17, wherein the nonionic surfactant is a polyoxyethylensorbitan fatty acid ester or a polysorbate.

19. The pharmaceutical composition of claim 17, wherein the pharmaceutical composition is a vaccination composition for a human and/or animal subject.

20. A kit comprising the pharmaceutical composition of claim 17 and a container.

21. An expression vector comprising the nucleic acid of claim 14.

22. A host cell comprising the nucleic acid according to claim 14, in functional association with an expression control sequence.

23. A nucleic acid encoding an antibody or antigen-binding fragment thereof which specifically binds to the receptor-binding domain (RBD) of the spike(S) protein of SARS-COV-2 comprising SEQ ID NO: 58, comprising a heavy chain variable region comprising a heavy chain CDR1, CDR2, and CDR3 and light chain variable region comprising a light chain CDR1, CDR2, and CDR3, wherein the heavy chain CDR1, CDR2, and CDR3 comprises GFTFTSSA (SEQ ID NO: 59), IVVGSGN (SEQ ID NO: 60) and AAPHCSSTICYDGFDI (SEQ ID NO: 61), respectively;

and wherein the light chain CDR1, CDR2, and CDR3 comprises QSVSSSY (SEQ ID NO: 62), GAS (SEQ ID NO: 63), and QQYGSSPWT (SEQ ID NO: 64), respectively.

24. The nucleic acid of claim 23, wherein the heavy chain variable region comprises SEQ ID NO: 13 and the light chain variable region comprises SEQ ID NO: 14.

25. A pharmaceutical composition comprising the antibody or antigen-binding fragment thereof of claim 23 and at least one pharmaceutically acceptable excipient that is a nonionic surfactant.

26. The pharmaceutical composition of claim 25, wherein the pharmaceutical composition is a vaccination composition for a human and/or animal subject.

27. A kit comprising the pharmaceutical composition of claim 25 and a container.

28. An expression vector comprising the nucleic acid of claim 23.

29. A host cell comprising the nucleic acid according to claim 23, in functional association with an expression control sequence.

* * * * *